United States Patent [19]

Halazy et al.

[11] Patent Number: 5,726,177

[45] Date of Patent: Mar. 10, 1998

[54] INDOLE-DERIVED ARYLPIPERAZINES AS LIGANDS FOR $5HT_1$-LIKE, $5HT_{1B}$ AND $5HT_{1D}$ RECEPTORS

[75] Inventors: Serge Halazy, Lagarrigue; Michel Perez, Castres; Michael Briley, Gaillac; Peter Pauwels, Lautrec, all of France

[73] Assignee: Pierre Fabre Medicament, Boulogne, France

[21] Appl. No.: 648,091

[22] PCT Filed: Nov. 17, 1994

[86] PCT No.: PCT/FR94/01343

§ 371 Date: May 17, 1996

§ 102(e) Date: May 17, 1996

[87] PCT Pub. No.: WO95/14004

PCT Pub. Date: May 26, 1995

[30] Foreign Application Priority Data

Nov. 19, 1993 [FR] France .................... 93 13875

[51] Int. Cl.⁶ .................... A61K 31/495; C07D 403/12; C07D 417/14
[52] U.S. Cl. .................... 514/253; 544/367; 544/373
[58] Field of Search .................... 544/373, 367; 514/253

[56] References Cited

U.S. PATENT DOCUMENTS

| | | | |
|---|---|---|---|
| 4,883,795 | 11/1989 | Lowe, III et al. | 544/373 |
| 5,242,925 | 9/1993 | Boetieher et al. | 544/373 |
| 5,418,237 | 5/1995 | Böttcher et al. | 544/373 |
| 5,532,241 | 7/1996 | Böttcher et al. | 544/373 |

FOREIGN PATENT DOCUMENTS

| | | |
|---|---|---|
| 500086 | 8/1992 | European Pat. Off. . |
| 2191488 | 12/1987 | United Kingdom . |
| 9402460 | 2/1994 | WIPO . |
| 9415916 | 7/1994 | WIPO . |

OTHER PUBLICATIONS

Millan et al, *Journal of Pharmacology and Experimental Therapeutics* , vol.262, pp.451–463 (1992).
Pauwells et al. in Neuropharmacol. 33 (1994), 67.
G. Martin, Naunyn–Schmiedeberg's Arch. Pharmacol. 342 (1990), 111.
Cephalia 15 (1995), 277–280, Buzzi et al.
TIPS 13 (1992), 307–311, Moskowitz.

*Primary Examiner*—Emily Bernhardt
*Attorney, Agent, or Firm*—Gordon W. Hueschen

[57] ABSTRACT

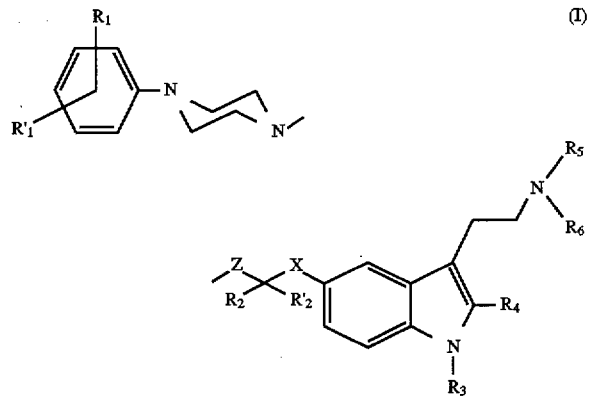

Novel indole-derived azylpiperazines of general formula (I), wherein, inter alia, $R_1$ is $NH_2$ or $NO_2$, $R'_1$, $R_2$, $R'_2$, $R_3$ and $R_4$ are H, Z is —C— and X is O. Methods for preparing such derivatives and the therapeutical uses thereof are also disclosed.

7 Claims, No Drawings

INDOLE-DERIVED ARYLPIPERAZINES AS LIGANDS FOR $5HT_1$-LIKE, $5HT_{1B}$ AND $5HT_{1D}$ RECEPTORS

The present application is a U.S. national application filed under 35 USC 371 of PCT/FR94/01343, filed Nov. 17, 1994, which in turn is based upon the priority of French application 9313875, filed Nov. 19, 1993.

The present invention relates to new indole-derived arylpiperazines, to processes for their preparation and to their therapeutic uses.

The compounds according to the present invention are ligands having a very high affinity and a very good selectivity for the receptors commonly known as $5HT_1$-like receptors and more particularly for the receptors known as $5HT_{1B}$ and $5HT_{1D}$ receptors, according to the new nomenclature recently proposed by P. Humphrey, P. Hartig and D. Hoyer (TIPS, 14, 233–236, 1993).

Medicaments including (alone or in association with other therapeutic agents) the active principles of the present invention are employed in the treatment, both curative and preventive, of diseases related to dysfunctioning of $5HT_{1\text{-like}}$ receptors, including $5HT_{1B}$, $5HT_{1D\alpha}$ and $5HT_{1D\beta}$ receptors, to their deregulation or to modifications in the activity of the endogenous ligand (generally serotonin).

It has moreover been demonstrated that serotonin could play a role in certain diseases such as depression, pain, obsessional convulsive disorders, panic attacks, obesity, schizophrenia, anxiety, certain sexual disfunctionings or alternatively certain forms of degeneration such as Parkinson's or Alzheimer's disease [refer, for example, to: S. Langer, N. Brunello, G. Racagni and J. Mendlecvicz, "Serotonin receptors subtypes: pharmacological significance and clinical implications", edited by Karger (1992), B. E. Leonard, Int. Clin. Psychopharmacology, 7, 13–21 (1992), D. G. Grahame-Smith, Int. Clin. Psychopharmacology, 6, Suppl. 4, 6–13 (1992), E. Zifa and G. Fillion, Pharmacological Reviews, 44, 401–458 (1992), and R. W. Fuller, J. Clin. Psychiatry, 53, 36–45 (1992)].

The compounds of the present invention are powerful and selective ligands of $5HT_{1\text{-like}}$ receptors which can act as agonists, partial agonists or antagonists as regards these receptors and can therefore be applied in the disorders related to serotonin mentioned above.

The majority of the compounds of the present invention are in addition powerful (as regards their affinity and as regards their intrinsic activity or effectiveness) and selective agonists of $5HT_{1B}$ and $5HT_{1D}$ receptors. Agonists of $5HT_{1\text{-like}}$ receptors and more particularly of $5HT_{1D}$ receptors have a selective vasoconstrictive activity and are used in the treatment of migraine and vasospastic disorders [(see, for example, A. Doenicke et al., The Lancet, 1, 1309–1311 (1988), M. D. Ferrari and P. R. Saxena, Cephalalgia, 13, 151–165 (1993), S. J. Peroutka, Headache, 30, 5–11 (1990), M. A. Moskowitz, TIPS, 13, 307–311 (1992), W. Feniuk, P. Humphrey, M. S. Perren, H. E. Connor and E. T. Whalley, J. Neurol., 238, S57–S61 (1991) and A. V. Deligonis and S. J. Peroutka, Headache, 31, 228–231 (1991)].

The compounds of the present invention, which are, for the most part, powerful and selective agonists of $5HT_{1\text{-like}}$ receptors, are therefore more particularly employed in the curative and prophylactic treatment of "classic" (with aura) and "common" (without aura) migraine attacks, facial vascular pain, chronic vascular cephalalgias and vasospastic disorders.

The prior state of the art in this field is illustrated in particular by

French Patent Applications F 9215919 (30/12/92) and F 9307982 (30/6/93), which describe new indole compounds derived respectively from piperazines and from arylamines as ligands of $5HT_{1B}$–$5HT_{1D}$ receptors.

Patent Application FR 2,671,971, which describes 5-O-carboxymethylated derivatives of tryptamine which have a good affinity for $5HT_{1D}$ receptors.

European Patent Applications 0,313,397, 0,486,666, 0,494,774-A1, 0,497,512-A2, 0,501,568-A1, 0,464,558 and 0,548,813-A1 and Patent Application WO 92/13856, which describe heterocyclic derivatives derived from tryptamine as agonists of $5HT_{1\text{-like}}$ receptors.

European Patent Applications 0,533,266, 0,533,267 and 0,533,268, which claim benzamides derived from arylpiperazine as antagonists of the $5HT_{1D}$ receptor.

Nevertheless, these patent applications do not in any case describe or suggest the indolic piperazine derivatives which form part of the present invention: the present invention describes a new class of indole-derived arylpiperazines which is distinguished from the closest derivatives of the prior art (and in particular from French Patent Application F 9215919, filed on 30/12/92) not only by their novel and different chemical structure but also by their biological profile and their therapeutic potential, since many compounds according to the present invention have the advantage of combining, for the first time in the same molecule, a very strong affinity for $5HT_{1B}$ or $5HT_{1D}$ receptors, a high selectivity with respect to $5HT_{1A}$ receptors and a notable agonist effectiveness (intrinsic activity).

The present invention relates to compounds of formula I:

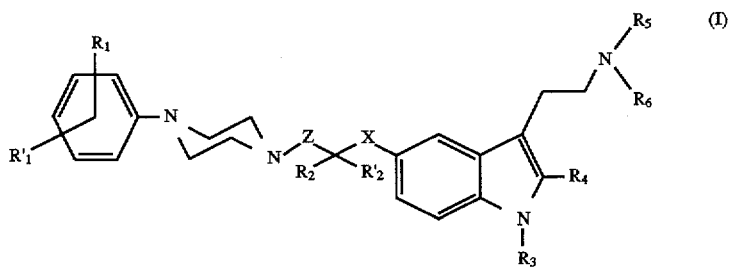

to their preparation and to the medicaments containing them.

In the formula (I), $R_1$ represents an $NH_2$, $NO_2$, $NH-NH_2$, $NH-OH$, $NCOR_7$ (OH), $NR_5R_6$, $NHCOR_7$, $NHCONR_5R_7$, $NHSO_2R_7$, $NHCO_2R_7$, $SO_2R_7$, $SO_2NHR_7$, $NHCH_2SR_7$, $NHCH_2S(O)R_7$, $NHCH_2SO_2R_7$, $CN$, $NHCONH_2$, $SO_2NH_2$, $N(SO_2R_7)_2$, $CH_2NR_5R_6$, $CH_2NHCOR_7$, $CH_2NHCONR_5R_6$, $CH_2NHSO_2R_7$, $CH_2NHCO_2R_7$ or $OSO_2R_7$ radical which can be in the o, m or p position on the aromatic ring.

$R'_1$ represents one or a number of substituents which can be in various positions on the aromatic ring, such as H, methyl, ethyl, propyl, isopropyl, n-buryl, s-butyl, t-butyl, trifluoromethyl, 2,2,2-trifluoroethyl, phenyl, benzyl, phenethyl, cycloalkyl, OH, $SR_5$, $OR_5$ or a halogen (chlorine, fluorine, bromine or iodine), or alternatively $R'_1$ can be identical to $R_1$.

Z represents C=O, C=S, $SO_2$, $(CH_2)_n$ or alternatively —CO$(CH_2)_n$— in which n is between 1 and 5.

$R_2$ and $R'_2$, which are identical or different, each represent a hydrogen atom, a linear or branched alkyl radical or a phenyl, benzyl, cycloalkyl or arylalkyl radical which are optionally substituted by one or a number of substituents chosen from halogen atoms or alkyl, aryl, acycl, alkoxy and alkylthio radicals.

X represents $CH_2$ or O or the $R_1$ $R'_1$ group represents a C—C double bond.

$R_3$ represents a hydrogen atom, a linear or branched alkyl radical or a phenyl, alkyl, aryl, $COR_7$, $CO_2R_7$, $CONHR_7$ or $SO_2R_7$ radical.

$R_4$ represents a hydrogen, chlorine, fluorine or bromine atom or a linear or branched alkyl radical.

$R_5$ and $R_6$, which are identical or different, each represent a hydrogen atom, a linear or branched alkyl radical, such as a methyl, ethyl, n-propyl, isopropyl, n-butyl, s-butyl or t-butyl, or an arylalkyl radical, such as a benzyl or a phenethyl.

$R_7$ represents a linear or branched alkyl radical comprising from 1 to 5 carbon atoms, a trifluoromethyl or 2,2,2-trifluoroethyl, an aryl radical (such as phenyl), a heterocycle (such as a 5-membered heterocycle containing one or a number of sulfur, oxygen or nitrogen atoms) or an arylalkyl (such as a benzyl or a phenethyl) in which the aromatic ring may be variously substituted in various positions by alkyl (methyl, ethyl, propyl or butyl), trifluoromethyl, 2,2,2-trifluoroethyl, hydroxyl, thiol, ether ($OCH_3$, $OC_2H_5$ or $OCH(Me)_2$), thioether ($SCH_3$ or $SC_2H_5$), halogen (chlorine, fluorine, bromine or iodine), nitrile, acetyl, carbonyl ($COR_5$), carboxyl ($CO_2R_5$), nitro ($NO_2$), amine ($NRSR_6$), $NHSO_2R_5$, $NHCO_2R_5$, $NHCOR_5$, $NHCONR_5R_6$ or $NHSO_2NR_5R_6$ residues, their salts, solyates and bioprecursors which are acceptable in therapeutic use.

In the preceding definitions and those which will be cited below, except when otherwise mentioned, the alkyl, alkoxy or alkylthio radicals contain 1 to 6 straight- or branched-chain carbon atoms and the cycloalkyl portions contain 3 to 7 carbon atoms. In the formula (I), the halogen atoms are preferably chlorine, fluorine or bromine atoms.

The compounds of formula (I) containing one or a number of asymmetric centers have isomer forms.

The racemates and the pure enantiomers of these compounds also form part of this invention.

The invention also comprises the salts, solyates (for example hydrates) and bioprecursors of these compounds which are acceptable in therapeutic use.

Mention will be made, among the salts which are acceptable in therapeutic use of the indoles of general formula (I), of the salts formed by addition with organic or inorganic acids and for example the hydrochlorides, the hydrobromides, the sulfates, the fumarates and the maleares. Other salts may be useful in the preparation of the compounds of formula (I), for example adducts with creatinine sulfate.

The expression "bioprecursors" as used in the present invention applies to compounds in which the structure differs from that of the compounds of formula (I) but which, administered to an animal or to a human being, are converted in the body to a compound of formula (I).

A valuable class of compounds according to the invention comprises those which correspond to the general formula (Ia)

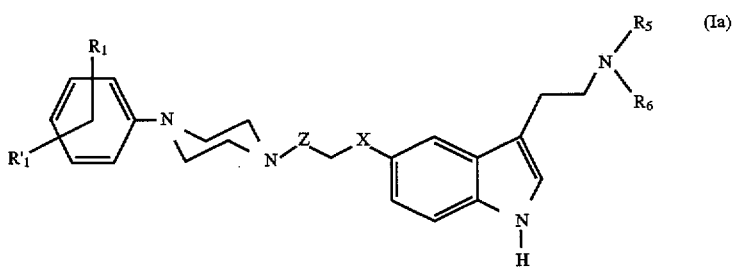

in which $R_1$, $R'_1$, Z, X, $R_5$ and $R_6$ are defined as above in the formula (I), and their salts, solyates (for example hydrates) and bioprecursors which are acceptable in therapeutic use.

The invention also comprises the preparation, by the processes described below, of the compounds of general formula (I) and of their salts, solyates (such as hydrates) or bioprecursors which are acceptable in therapeutic use.

Generally, the compounds of general formula (I) in which $R_6$ represents a hydrogen are prepared from derivatives of formula (II)

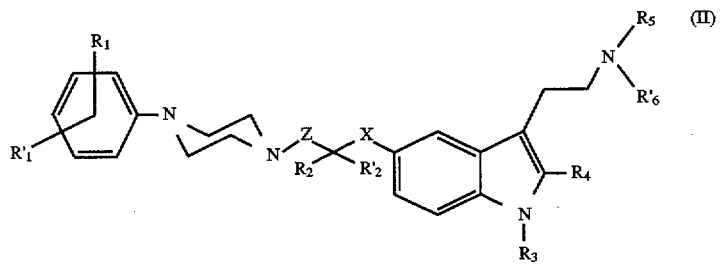

in which $R'_1$, $R_1$, Z, $R_2$, $R'_2$, X, $R_3$, $R_4$ and $R_5$ are described as above and $R'_6$ represents a $COR_8$ or $CO_2R_8$ group, preferably $CO_2R_8$ in which $R_8$ is preferably a t-butyl or benzyl residue. Conversion of the compounds of formula (II) in which $R'_6$ is a $CO_2{}^tBu$ (BOC) group to compounds of formula (I) in which $R_6$ is a hydrogen is preferably carried out using an acid, such as trifluoroacetic acid or hydrochloric acid, in an organic solvent, such as ether, tetrahydrofuran, toluene, dichloromethane, chloroform, methanol, ethanol or isopropanol, at a temperature of between $-15°$ C. and $40°$ C. Conversion of the compounds of formula (II) in which $R'_6$ is a $CO_2CH_2C_6H_5$ (commonly called Z) group to a compound of formula (I) in which $R_6$ is a hydrogen is preferably carried out by catalytic hydrogenation, using for example palladium-on-charcoal as catalyst, under atmospheric hydrogen pressure, in a solvent, such as THF, ethanol, isopropanol or ethyl acetate, which can contain up to 10% of acetic or citric acid, at a temperature of between $0°$ and $60°$ C. In the following definitions, the expression "$R_6$ described as above" should be regarded as implying that $R_6$ can also represent $R'_6$.

The preparation of the derivatives of formula (I) in which $R'_1$, $R_1$, Z, $R_2$, $R'_2$, X, $R_3$, $R_4$, $R_5$ and $R_6$ are described as above and X represents an oxygen atom are prepared, generally, by condensation of a derivative of general formula (III)

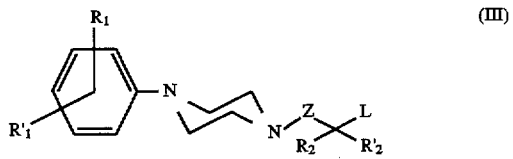

in which $R_1$, $R'_1$, Z, $R_2$ and $R'_2$ are defined as in the formula (I) and L represents a leaving group, such as a halogen (preferably a bromine, iodine or chlorine atom) or an O-mesylate, O-triflate or O-tosylate, with a derivative of serotonin of general formula (IV):

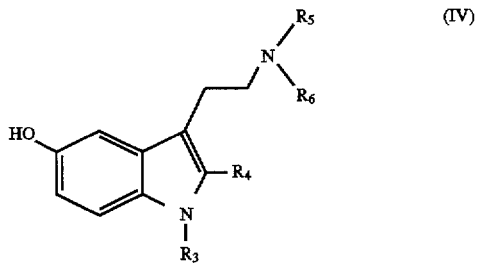

in which the $R_3$, $R_4$, $R_5$ and $R_6$ residues are described as above.

The preparation of the derivatives of formula (I) by condensation of the derivatives of formula (III) with the derivatives of formula (IV) can be carried out, generally, in the presence of an organic base (NaH, KH, $Et_3N$, DBU, DBN, TMP, DIPEA, t-BuOK) or an inorganic base ($K_2CO_3$, $KHCO_3$, $NaHCO_3$, $CS_2CO_3$, KOH, NaOH, $CaCO_3$ and the like), in an anhydrous solvent, such as THF, DMF, DMSO, acetone, diethyl ketone, methyl ethyl ketone, acetonitrile or DME, at a temperature of between $20°$ and $140°$ C., in the present or in the absence of a salt as catalyst which may be KI, $Bu_4NI$, LiI, $AgBF_4$, $AgClO_4$, $Ag_2CO_3$, KF, $Bu_4NF$ or CsF. The choice of the experimental conditions for carrying out the condensation between the derivatives of formula (III) and (IV) in order to obtain the derivatives of formula (I) is very clearly dependent on the nature of the substituents in the reactants (III) and (IV) and more particularly on the nature of the Z, $R_2$ and $R'_2$ groups. By way of example, when Z is a carbonyl (CO) functional group, $R_2$ is a hydrogen atom and X a halogen, condensation between (III) and (IV) to give (I) is preferably carried out at $80°$ C., in methyl ethyl ketone, in the presence of an excess of $K_2CO_3$ and of a catalytic amount of KI. When Z is a carbonyl group and when $R_2$ and $R'_2$ are both other than a hydrogen, the preferred method comprises the reaction of a derivative of formula (IV) with this derivative of formula (III), in the presence of a silver salt such as silver tetrafluoroborate and of an inorganic base such as $K_2CO_3$. When the Z group is defined as $(CH_2)_n$, condensation between the (III) and (IV) derivatives is carried out in a solvent such as DMF or DMSO, in the presence of a base such as DBU or DIPEA, at $100°$ C., in the presence of a catalytic amount of $Bu_4NI$ or of KI. An alternative method comprises the condensation of the (III) and (IV) derivatives, under neutral conditions, in DMF, in the presence of a large excess of a fluoride such as KF, CsF or $Bu_4NF$.

The compounds of general formula (III) in which the $R_1$, $R'_1$, $R_2$, $R'_2$ and L substituents are defined as above are prepared by methods which differ according to the nature of the Z residue. Thus, the derivatives of formula (III) in which Z is a carbonyl group forming part of an amide functional group are obtained by reaction of the piperazines of general formula (V).

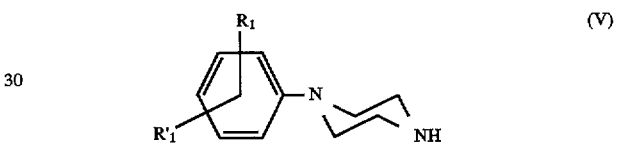

in which the $R_1$ and $R'_1$ residues are defined as in the formula (I), with a derivative of formula (VI)

in which $R_2$ and $R'_2$ are defined as in the formula (I) and Z represents C=O. This reaction, which makes possible the preparation of the derivatives of formula (III) in which Z=CO and X=Cl from the arylamines (V) and the acid chlorides (VI), is a well known reaction for the formation of amides from an amine and from an acid chloride and can be carried out in a solvent such as dichloromethane, THF, chloroform, acetone, methyl ethyl ketone, DME or acetonitrile, at a temperature of between $-20°$ C. and $80°$ C., in the presence of a base, such as a tertiary amine (DBU, $Et_3N$ or DIPEA) or inorganic bases, such as carbonates ($KHCO_3$, $NaHCO_3$, $K_2CO_2$, $Na_2CO_3$ or $Cs_2CO_3$), sodium hydroxide or alternatively potassium hydroxide.

The derivatives of formula (III) in which Z represents a $—(CH_2)_n—$ group are generally prepared by condensation of an arylamine of formula (V) with a derivative of formula (VII)

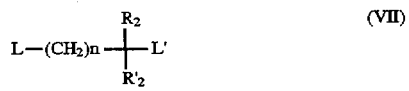

in which L represents a leaving group, such as a chlorine, a bromine, an iodine or a mesylate, tosylate or triflate group, $R_2$ and $R'_2$ are defined as in the formula (I) and L' can be either identical to L or represents an OR' group in which R' is defined as a protective group for an alcohol, such as a silyl ether ($SiMe_3$, $Si^tBuMe_2$ or $SiC_6H_5Me_2$), a tetrahydropyran or alternatively a benzyl or a trityl. It is clearly understood that, in the case where L' is other than L, condensation between the piperazine of formula (V) and the intermediate (VII) is followed by hydrolysis of the OR' protective group in order to give anintermediate alcohol derivative which is converted to a leaving group which results in the compounds (III) in which $R_1$, $R'_1$, $R_2$, $R'_2$ and L are defined as above. In the procedure mentioned above, hydrolysis of the OR' functional group to an alcohol is carried out by the described and appropriate methods according to the nature of R' (with reference to the work by T. W. Greene, "Protective Groups in Organic Synthesis", John Wiley & Sons, 1981) and the conversion of the alcohol thus obtained to the leaving group [(so as to obtain the compounds (III)] is carried out by techniques and methods which are well known for this type of conversion, such as the use of $SOCl_2$ or $POCl_3$ in dichloromethane for the formation of derivatives of formula (III) in which L=Cl, the use of $PBr_3$ or $Br_2PPh_3$ for the formation of derivatives of formula (III) in which L=Br, the use of $PI_3$ or $P_2I_4$ for the formation of derivatives of formula (III) in which L=I, the use of tosyl chloride for the formation of derivatives of formula (III) in which L=OTos, the use of mesyl chloride for the formation of derivatives of formula (III) in which L=OMes and finally the use of triflic anhydride for the formation of derivatives of formula (III) in which L=OTf.

The derivatives of formula (III) in which $Z=SO_2$ are generally prepared by reaction of the piperazine derivatives of general formula (V), in which the $R_1$ and $R'_1$ groups are defined as in the general formula (I), with a derivative of formula (VI) in which $R_2$ and $R'_2$ are defined as in the formula (I) and Z represents $SO_2$.

The compounds of general formula (I) can also be prepared by another process which comprises the treatment of an arylpiperazine of general formula (V) defined as above with a derivative of serotonin of general formula (VIII.

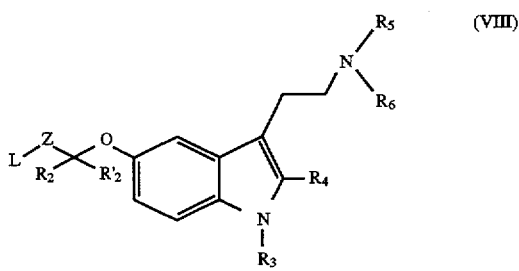

(VIII)

in which the $R_2$, $R'_2$, $R_3$, $R_4$, $R_5$ and $R_6$ residues are defined as described above in the formula (I) and L is defined as a leaving group, such as a halogen (preferably a bromine, iodine or chlorine atom), a mesylate, a rosylate or a triflate, or the precursor of a leaving group, such as a hydroxyl radical.

The preparation of the derivatives of formula (I) in which Z represents a —$(CH_2)_n$— residue by this process is carried out by condensation between a piperazine derivative of formula (V) and an intermediate of general formula (VIII) in the presence of an organic base (NaH, 'BuOK, DBU or DIPEA) or an inorganic base (KOH, $K_2CO_3$, $NaHCO_3$ or $Cs_2CO_3$) in an anhydrous solvent, such as THF, DMF, DMSO, acetonitrile or methylethyl ketone, at a temperature of between 20° and 100° C.

The intermediates of formula (VIII) can be prepared by condensation of a derivative of serotonin of formula (IV)

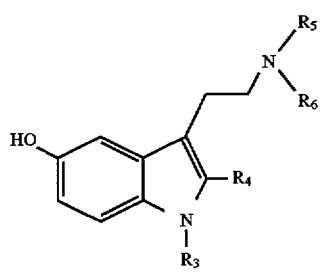

IV in which $R_3$, $R_4$, $R_5$ and $R_6$ are defined as in the formula (I), with a derivative of formula (IX)

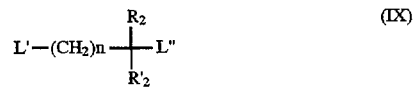

(IX)

in which L' and L" can be simultaneously halogens (chlorine, bromine or iodine) if $R_2$ and $R'_2$ represent a hydrogen atom; in the other cases, L' represents an OR group where R is a conventional protective group, such as a silyl (trimethylsilyl, triethylsilyl or 'butyldimethylsilyl), benzyl, tetrahydropyranyl or trityl group, and in this case L" represents a leaving group, such as a halogen (preferably a chlorine, an iodine or a bromine), an OMes, an OTos or an OTf. In this case, after condensation, L', which represents OR, will be deprotected and converted to the leaving group L as defined in the formula (VIII) by the methods described above.

This condensation reaction between the intermediates (IV) and (IX) as described above is carried out in basic medium (in the present of a base, such as NaH, KH, 'BuOK, $K_2CO_3$, $Cs_2CO_3$, DIPEA or DBU) in an anhydrous solvent, such as DMSO, DMF, THF, acetonitrile, methyl ethyl ketone or DME, at a temperature of between 0° and 100° C.

In the specific case of the derivatives of formula (I) in which $R_1$, $R'_1$, $R_3$, $R_4$, $R_5$ and $R_6$ are described as above but where Z represents —$(CH_2)$—, a preferred method of synthesis comprises the reduction of the corresponding derivatives of formula (I) in which Z represents CO by a reducing agent which makes possible the conversion of an amide to an amine, such as borane ($BH_3.Me_2S$) or $LiAlH_4$, use being made of the methods and techniques which are well known for this type of reduction.

In the case of the derivatives of formula (I) in which $R_1$, $R'_1$, Z, $R_2$, $R'_2$, $R_3$, $R_4$, $R_5$ and $R_6$ are described as above and in which $X=CH_2$, a general method of synthesis comprises the condensation of an intermediate of general formula (X)

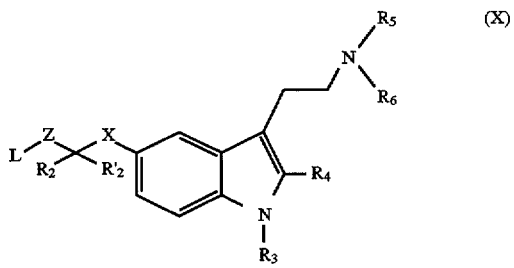

(X)

in which L is a leaving group defined as above and Z, $R_2$, $R'_2$, $R_3$, $R_4$, $R_5$ and $R_6$ are described as above, with an arylpiperazine of general formula (V) in which $R_1$ and $R'_1$ are defined as above. The methods used for obtaining the products of general formula (I) in which $X=CH_2$ by condensation of the intermediates (X) and (V) vary according to the nature of the Z residue and may be comparable, according to the variation in Z, to the methods described previously for the synthesis of the products (III) by condensation of the intermediates (V) and (VI).

The indole derivatives of general formula (X) in which Z=CO, L is a leaving group such as a halogen, $R_2$, $R_3$, $R_4$, $R_5$ and $R_6$ are described as above and $R'_2$ is a hydrogen can be obtained by condensation of a 5-bromoindole derivative of formula (XI)

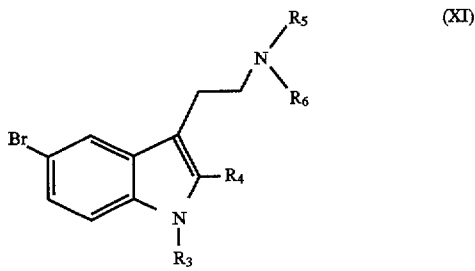

in which $R_3$, $R_4$, $R_5$ and $R_6$ are defined as above, with an acid or an ester derived from this unsaturated acid of general formula (XII)

in which the $R_2$ residue is defined as above, use being made of a palladium (o) catalysis according to the method for the alkylation of aromatics well known as the Heck reaction, followed by reduction of the double bond by catalytic hydrogenation (atmospheric $H_2$, Pd/C, methanol) and by conversion of the acid or of the ester thus formed to the derivative X by methods and techniques which are well known to the person skilled in the art for the conversion of a carboxylic acid or of a corresponding ester to the acid chloride X (L=Cl, Z=CO) or to an activated ester capable of being condensed with an amine in order to form an amide (in particular by intermediate formation of a mixed anhydride with ethyl chloroformate).

The derivatives of general formula (I) in which $R_1$, $R'_1$, $R_2$, $R_3$, $R_4$, $R_5$ and $R_6$ are described as above, Z=X=$CH_2$ and $R'_2$=H are prepared from the products of general formula (I) in which $R_1$, $R'_1$, $R_2$, $R_3$, $R_4$, $R_5$ and $R_6$ are described as above, Z=CO, X=$CH_2$ and $R'_2$=H by reduction of the amide functional group with a reducing agent well known for this type of reaction, such as lithium aluminum hydride, in an aprotic solvent, such as ether or THF.

The derivatives of general formula (I) in which $R_1$, $R'_1$, $R_2$, $R_3$, $R_4$, $R_5$ and $R_6$ are described as above, Z=$SO_2$, X=$CH_2$ and $R'_2$=H are prepared by the Heck condensation from an intermediate of formula (XI) with an unsaturated sulfonamide of formula (XIII)

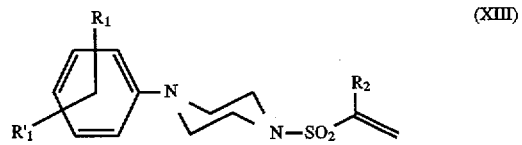

in a solvent such as triethylamine in the presence of a phosphine such as tri(O-tolylphosphine) at a temperature of between 60° and 100° C.

The methods for the preparation of derivatives of formula (I) from other derivatives of formula (I) in which at least one of the $R_1$, $R'_1$, Z, $R_2$, $R'_2$, X, $R_3$, $R_4$, $R_5$ or $R_6$ substituents are different, by techniques and methods well known to the person skilled in the art, must also be regarded as an integral part of this invention.

In particular, the present invention also claims a method for the preparation of numerous compounds of general formula (I), in which $R_1$ is an $NH_2$, NH—$NH_2$, NHOH, $NR_5R_6$, $NHCOR_7$, $NHCONR_5R_7$, $NHSO_2R_7$ or $NHCO_2R_7$ radical in the ortho, meta or para position, from compounds of general formula (Ib) prepared as described above and in which $R_1$, Z, $R_2$, $R'_2$, X, $R_3$, $R_4$, $R_5$ and $R_6$ are described as above.

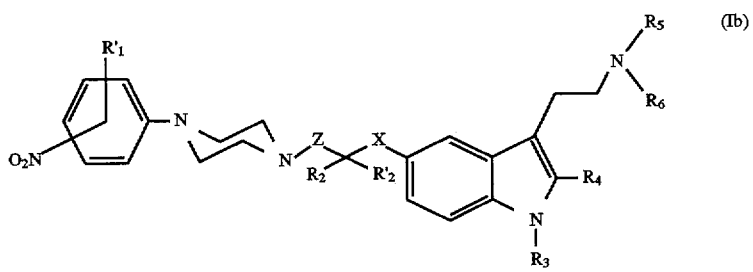

Thus, the compounds of general formula (Ic), in which $R'_1$, Z, $R_2$, $R'_2$, X, $R_3$, $R_4$, $R_5$ and $R_6$ are described as above

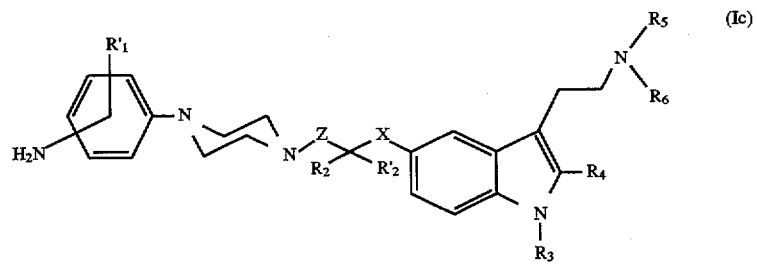

are prepared by reduction of the nitro group by methods and techniques well known for this type of reduction (with reference, for example, to: R. C. Larouk "Comprehensive Organic Transformation", p. 412 (1989), VCH.), such as atmospheric hydrogenation catalyzed by paladium-on-charcoal, the use of $SnCl_2$ or of zinc or alternatively of rhodium catalyst in the presence of hydrazine.

This last method additionally makes it possible to control the reduction of the nitro group and also to isolate the intermediate hydroxylamine of general formula (Id), which also forms part of this invention.

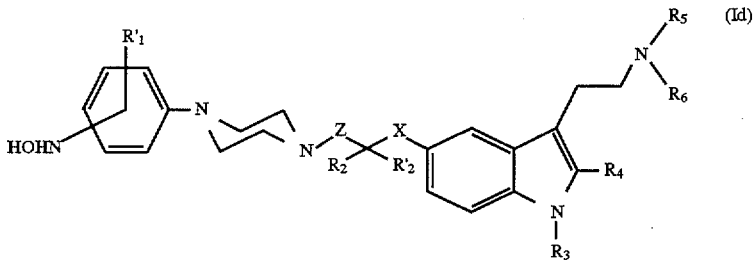

The synthetic intermediates of general formula (Ie), in which $R_1$, Z, $R_2$, $R'_2$, X, $R_3$, $R_4$, $R_5$ and $R_6$ are described as above

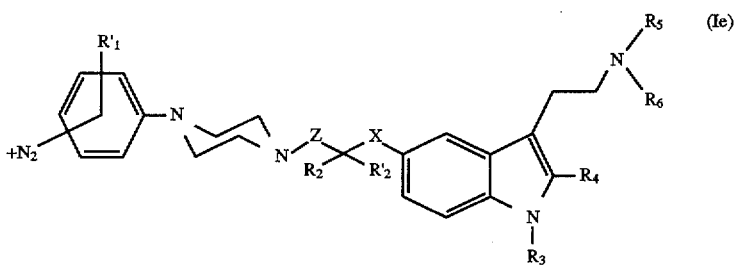

can also be prepared from the anilines of structure Ic, after reaction with nitrous acid ($HNO_2$), by using methods and techniques well known for this type of conversion (cf. Patai, "The Chemistry of Diazonium and Diazo Groups", Wiley, N.Y., 1978).

These intermediates (Ie) make it possible to prepare the products of general formula (Ia), in which $R'_1$, Z, $R_2$, $R'_2$, X, $R_3$, $R_4$, $R_5$ and $R_6$ are described as above but in which $R_1=SO_2NHR_7$, after reaction with $SO_2$ in the presence of cupric chloride (Gilbert, Synthesis, 1–10, 1969), followed by condensation of the intermediate sulfonyl chloride with an amine ($R_7NH_2$) in the presence of a base, such as pyridine, triethylamine or DMAP.

The intermediates (Ie) also make it possible to prepare the products of general formula (Ia), in which $R'_1$, Z, $R_2$, $R'_2$, X, $R_3$, $R_4$, $R_5$ and $R_6$ are described as above but in which $R_1=NH-NH_2$, after reduction of the diazonium group, in particular by using sodium sulfite ($Na_2SO_3$) (Huisgen and Lux, Chem. Bet. 93, 540, 1960).

The compounds of general formula (I), in which the $R_1$ group represents $NR_5R_6$, $NHCOR_7$, $NHCONR_5R_7$, $NHSO_2R_7$, $NHCO_2R_7$ in the ortho, meta or para position, can also be obtained from the compounds of formula (Ic) in which $R'_1$, Z, $R_2$, $R'_2$, X, $R_3$, $R_4$, $R_5$ and $R_6$ are described as above by various reactants and methods which depend on the nature of the $R_1$ group. Thus, the compounds of formula (I) in which $R_1$ represents an $NR_5R_6$ group (in which $R_6=H$ or $R_5$) are prepared by reaction in a basic medium (in the presence of an organic base, such as DBU, $^tBuOK$, DMAP or DIPEA, or an inorganic base, such as $CS_2CO_3$, HaH or KH) of the intermediate (Ic) with corresponding alkylating agents ($R_5$—L in which L represents a chlorine, bromine or iodine atom or an O-mesyl, O-toxyl or O-trifluorasulfonyl radical). Control of the reaction (time, solvent, temperature or number of equivalents of $R_5$—L) makes it possible to obtain the mono- or dialkylated aniline.

The compounds of general formula (I) in which $R_1$ represents $NHCOR_7$ are also prepared by reaction of the corresponding anilines of formula (Ic) after reaction with an acylating agent, such as an acid chloride ($ClCOR_7$) or an anhydride [$(R_7CO)_2O$], in the presence of a base, such as triethylamine, pyridine or DMAP, in a polar aprotic solvent, such as DMF or dichloromethane.

The compounds of formula (I) in which $R_1$ represents $NHCOOR_7$ are also accessible by a similar reaction in which the amine of formula (Ic) is condensed with a chloroformate of structure $ClCOOR_7$.

The compounds of formula (I) in which $R_1$ represents $NHSO_2R_7$ are themselves also accessible by a similar reaction which comprises the condensation of the aniline of formula (Ic) with a sulfonyl chloride of formula $ClSO_2R_7$.

The compounds of formula (I) in which $R_1$ represents $NHCONR_5R_7$ can also be obtained from the corresponding aniline (Ic) by different methods. Thus, the amines of general formula (Ic) can be converted beforehand to isocyanates of formula (I) in which $R_1$ represents N=C=O (cf. Patai, "The Chemistry of Cyanates and Their Thio Derivatives, pt. 2, Wiley, N.Y., 1977; pp 619–818 and 1003–1221), followed by the addition reaction of an amine of formula $HNR_5$—$R_7$ in the presence of a base such as $Et_3N$. Alternatively, the compounds of formula (I) in which $R_1=NHCONR_5R_7$ can also be prepared by condensation of the aniline of formula (Ic) with an intermediate of formula $ClCONR_5R_7$ in the presence of a base, such as $ET_3N$ or DMAP, in a polar aprotic solvent, such as $CH_2CL_2$ or DMF.

The derivatives of general formula (I) in which $R_1$, $R'_1$, $R_2$, $R'_2$, X, $R_3$, $R_4$, $R_5$ and $R_6$ are described as above and Z represents C=S are obtained by reaction of the compounds of general formula (I), in which $R_1$, $R'_1$, $R_2$, $R'_2$, X, $R_3$, $R_4$, $R_5$ and $R_6$ are described as above and Z represents C=O, with Lawesson's reagent [2,4-bis-(4-methoxyphenyl)-1,3-dithia-2,4-diphosphetane-2,4-disulfide]in toluene.

The derivatives of general formula (I) in which $R_1$, $R'_1$, Z, $R_2$, $R'_2$, X, $R_3$, $R_4$, $R_5$ and $R_6$ are described as above and in which $R_3$ represents a hydrogen can be converted to derivatives of formula (I) in which $R_3$ represents an alkyl, benzyl, $COR_7$, $CO_2R_7$, $CONHR_7$ or $SO_2R_7$ radical by reaction in basic medium with, respectively, an alkyl halide, a benzyl halide, an acid chloride, a chloroformate, a chloroformamide or a sulfonyl chloride by methods and techniques well known for this type of reaction and which, by way of example, are described in "The Chemistry of Indoles", edited by R. S. Sundberg, vol. 18 of "Organic Chemistry, A Series of Monographs", Academic Press, NY, 1970.

It will be understood that, in some of the above conversions, it may be necessary or desirable to protect possible sensitive groups of the molecule in question in order to avoid undesirable side reactions. This can be carried out by the use of conventional protective groups such as those described in "Protective Groups in Organic Synthesis", edited by J. F. McOwie, Plenum Press, 1973 and in T. W. Greene, "Protective Groups in Organic Synthesis", John Wiley & Sons, 1981. The protective groups can be removed during any suitable subsequent stage, by using methods and techniques also described in the references cited above. Thus, in some specific cases, it may be necessary to protect the indole nitrogen during the preparation of compounds of formula (I) in which $R_3$ represents a hydrogen.

When it is desired to isolate a compound according to the invention in the salt form, for example in the form of a salt formed by addition with an acid, this can be done by treating the free base of general formula (I) with an appropriate acid, preferably in an equivalent amount, or with creatinine sulfate, in an appropriate solvent.

When the processes described above for preparing the compounds of the invention give mixtures of stereoisomers, these isomers can be separated by conventional methods, such as preparative chromatography.

When the new compounds of general formula (I) have one or a number of asymmetric centers, it can be prepared in the form of a racemic mixture or in the form of enantiomers, whether by enantioselective synthesis or by resolution. The compounds of formula (I) having at least one asymmetric center can, for example, be separated into their enantiomers by the usual techniques, such as the formation of diastereomeric pairs by formation of a salt with an optically active acid, such as (−)-di-p-toluoyl-1-tartaric acid, (+)-di-p-toluoyl-1-tartaric acid, (+)-camphorsulfonic acid, (−)-camphorsulfonic acid, (+)-phenylpropionic acid or (−)-phenylpropionic acid, followed by fractional crystallization and regeneration of the free base. The compounds of formula (I) in which $R_6$ is a hydrogen comprising at least one asymmetric center can also be resolved by formation of diastereomeric amides which are separated by chromatography and hydrolyzed in order to release the chiral auxiliary.

Generally, the compounds of formula (I) can be purified by the usual methods, for example by crystallization (in particular when the compounds of formula (I) are isolated in the salt form), chromatography or extraction.

The examples which follow illustrate the invention without, however, limiting the scope thereof.

EXAMPLE 1

2-[3-(2-Aminoethyl)-1-H-indol-5-yloxy]-1-([4-nitrophenyl)piperazin-1-yl]ethanone hydrochloride

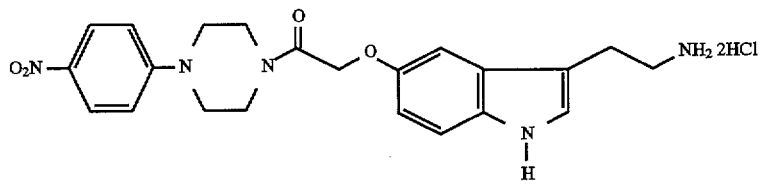

1

1A: 3-(2-N-tert-butoxycarbonyl)aminoethyl)-1-H-indol-5-ol

The creatine sulfate monohydrate salt of serotonin (102 g, 252 mmol) is treated with di-tert-butyl dicarbonate (82.6 g, 378 mmol) in water (2.1 l) in the presence of 2N sodium hydroxide (420 ml) at room temperature. After 1 hour, the reaction mixture is diluted with ethyl acetate (3 l) and stirred for 10 minutes. The two phases formed are separated by settling; the organic phase is washed with water, dried over sodium sulfate, filtered and then evaporated to dryness. The syrup obtained is chromatographed on a column of silica gel eluted with a dichloromethane/methanol (20/1, v/v) mixture. The pure compound is isolated in the form of a brown syrup (65.9 g, 95%). Elemental analysis ($C_{15}H_{20}N_2O_3$), % calculated: C 65.20, H 7.30, N 10.14, % found: C 64.15, H 7.47, N 9.77.

Proton nuclear magnetic resonance spectrum, $CDCl_3$ (ppm): 1.44 s, 9H (t-Bu); 2.86 t, 2H ($CH_2$); 3.45 m, 2H ($CH_2$); 4.68 s, 1H (NH); 5.59 s, 1H (O—H); 6.77–7.26 m, 4H (Ar+ethylenic); 7.99 s, 1H (NH).

1B: 2-chloro-1-[4-nitrophenyl)piperazin-1-yl]ethanone (4-Nitrophenyl)piperazine (7 g, 33.8 mmol) in solution in methyl ethyl ketone (223 ml), in the presence of calcium carbonate (10.1 g; 101.4 mmol), is treated at 0° C. and dropwise with chloroacetyl chloride (3.2 ml; 40.5 mmol). After 1 hour at 0° C., the reaction mixture is diluted with ethyl acetate, filtered through celite and washed with water and then with a sodium chloride solution. The organic phase is dried over sodium sulfate, filtered and evaporated. The brown solid obtained (7.8 g, 82%) is used without additional purification in the following stage.

1C: 2-[3-(2-N-(tert-butoxycarbonyl)aminoethyl)-1-H-indol-5-yloxy]-1-[4-(4-nitrophenyl)piperazin-1-yl]ethanone.

A mixture of the compound 1A (9.67 g, 35.01 mmol) and of the compound 1B (24.8 g, 87.5 mmol) in methyl ethyl ketone (400 ml), in the presence of potassium carbonate (12.1 g, 87.5 mmol) and of potassium iodide (581 mg; 3.5 mmol), is heated at reflux for 5 hours. The compound 1A (2.0 g, 7.2 mmol) is again added and the reaction mixture is stirred at reflux for an additional 1 hour. The mixture is then diluted with dichloromethane, filtered through celite and washed with water and then with a sodium chloride solution. The organic phase is dried over sodium sulfate, filtered and then evaporated to dryness. The syrup obtained is chromatographed on a column of silica gel eluted with a dichloromethane/acetone (3/1, v/v) mixture. The pure product is obtained in the form of an orange powder (18.2 g, 83%).

Elemental analysis ($C_{27}H_{33}N_5O_6$), % calculated: C 61.94, H 6.35, N 13.38, % found: C 61.19, H 6.22, N 13.02.

Proton nuclear magnetic resonance spectrum, $CDCl_3$ (ppm):

1.44 s, 9H (t-Bu); 3.86 t, 4H ($CH_2$); 3.83 m, 4H ($CH_2$); 4.65 s, 1H (NH); 4.79 s, 2H ($COCH_2O$); 6.79–7.30 m, 6H (Ar+ethylenic); 8.11–8.16 m, 3H (Ar+NH). Melting point: 198° C.

1: 2-[3-(2-Aminoethyl)-1H-indol-5-yloxy]-1-[4-(4-nitrophenyl)piperazin-1-yl]ethanone hydrochloride.

The product 1C (930 mg, 1.77 mmol) in solution in toluene (46 ml) is treated with trifluoroacetic acid (10 ml). After 1 h 30 at room temperature, the mixture is diluted with dichloromethane and washed with 2N sodium hydroxide and then with water. The organic phase is dried over sodium sulfate, filtered and evaporated to dryness. The syrup obtained is chromatoraphed on a column of silica gel eluted with a chloroform/methanol/aqueous ammonia (80/18.5/1.5, v/v) mixture. The pure product is obtained in the form of a yellow syrup (317 mg, 45%). This compound is diluted in methanol and the bishydrochloride is formed by addition of the necessary amount of hydrochloric acid in methanol.

Elemental analysis ($C_{22}H_{27}N_5O_4Cl_2$), % calculated: C 53.23, H 5.48, N 14.11, % found: C 53.83, H 5.77, N 13.80. 1H nuclear magnetic resonance spectrum, d6-DMSO (ppm):

2.99 s, 4H ($CH_2$); 3.54–3.71 m, 8H ($CH_2$), 4.84 s, 2H ($COCH_2O$); 6.77–6.83 dd, 1H (ethylenic); 7.01–7.29 m, 5H (Ar); 8.06–8.11 m, 5H (Ar+$NH_3^+$); 10.85 d, 1H (NH). Melting point: 206° C.

EXAMPLE 2

2-[3-(2-Aminoethyl)-1H-indol-5-yloxy]-1-[4-(aminopheryl)piperazin-1-yl]ethanone hydrochloride

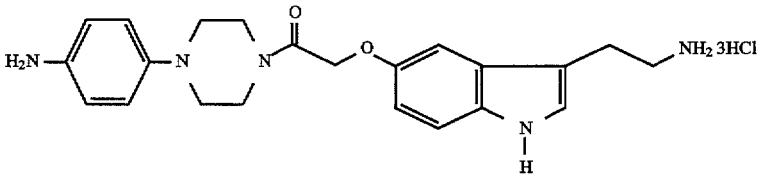

2

The product 1 (5 g, 9.5 mmol), in suspension in methanol (250 ml) in the presence of a catalytic amount of palladium-on-charcoal (505 mg, 0.47 mmol), is hydrogenated in a Parr apparatus, under a pressure of 40 psi. After 12 hours, the mixture is filtered through celite and the latter is washed a number of times with methanol, which makes it possible to obtain the virtually pure reduction product in the filtrate. The celite is then washed with dichloromethane, which makes it possible to recover the unreacted starting material.

The filtrate containing the product formed is evaporated to dryness and the syrup obtained is chromatographed on a column of silica gel eluted with a dichloromethane acetone (3/1, v/v) mixture. The pure product is obtained in the form of a yellow syrup (2.8 g, 60%).

1H nuclear magnetic resonance spectrum, $CDCl_3$ (ppm):

1.44s, 9H (t-Bu); 2.18 s, 2H ($NH_2$); 2.87–3.80 m, 12H ($CH_2$); 4.66 s, 1H (NH); 4.77 s, 2H ($COCH_2O$); 6.63–7.28 m, 8H (Ar+ethylenic); 8.16 s, 1H (NH).

2: 2-[3-(2-Aminoethyl)-1H-indol-5-yloxy]-1-[4-(4-aminophenyl)piperazin-1-yl]ethanone hydrochloride The product 2A (252 mg, 0.51 mmol), in solution in toluene (13 ml) is treated with trifluoroacetic acid (3 ml) at room temperature. After 1 hour, the mixture is diluted with ethyl acetate and washed with 2N sodium hydroxide, with water and then with a saturated sodium chloride solution. The organic phase is dried over sodium sulfate, filtered and evaporated. The syrup obtained is chromatographed on a column of silica gel eluted with a chloroform/methanol/aqueous ammonia (80/18.5/1.5, v/v) mixture. The pure product is isolated in the form of a yellow syrup (174 mg, 87%). The compound obtained is dissolved in methanol and the hydrochloride is formed by addition of the necessary amount of hydrochloric acid in methanol.

Elemental analysis ($C_{22}H_{30}N_5O_2Cl_3.2H_2O$), % calculated: C 49.03, H 6.36, N 12.99, % found: C 49.37, H 6.18, N 12.67.

1H nuclear magnetic resonance spectrum, d6-DMSO (ppm):

2.99–3.70 m, 12H ($CH_2$); 4.83 s, 2H ($COCH_2O$); 6.76–6.82 dd, 1H (ethylenic); 7.05–7.28 m, 7H (Ar); 8.13 s, 3H ($NH_3^+$); 10.86 s, 1H (NH). Melting point: 196° C.

EXAMPLE 3

N-[4-(4-{2-[3-(2-Aminoethyl)-1H-indol-5-yloxy]acetyl}piperazin-1-yl)phenyl]acetamide hydrochloride

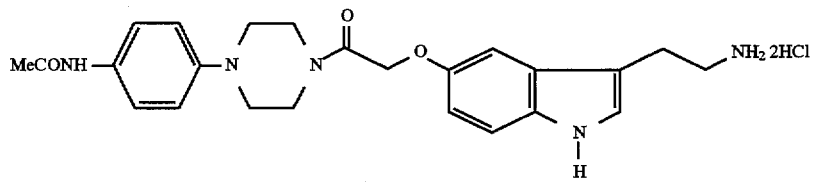

3

The product 2A (300 mg, 0.61 mmol), in solution in pyridine (7.5 ml), is treated at 0° C. with acetic anhydride (60 ml, 0.61 mmol). After stirring for 2 hours at room temperature, the mixture is diluted with ethyl acetate and washed successively with a saturated copper sulfate solution, water and finally with a saturated sodium chloride solution. The organic phase is dried over sodium sulfate, filtered and evaporated to dryness. The syrup obtained is chromatographed on a column of silica gel eluted with a dichloromethane/acetone (2/1, v/v) mixture. The pure product is obtained in the form of a yellow syrup (249 mg; 77%).

This compound is then deprotected according to the method described for the preparation of Example 2.

Purification of the product in the base form is carried out by chromatography on a column of silica gel eluted with a chloroform/methanol/aqueous ammonia (80/18.5/1.5, v/v) mixture. The pure product is isolated in the form of a colorless syrup which results, after treatment with hydrochloric acid in methanol, in the compound 3 (113 mg, 36%).

Elemental analysis ($C_{24}H_{31}N_5O_3Cl_2.0.5H_2O$), % calculated: C 55.71, H 6.23, N 13.53, % found: C 55.70%, H 6.40, N 13.46.

1H nuclear magnetic resonance spectrum, d6-DMSO (ppm): 2.00 s, 3H ($CH_3$); 2.76–3.16 m, 8H ($CH_2$); 3.68 m, 6H ($CH_2+H_2O$); 4.82 s, 2H (CO$\underline{CH_2}$O); 6.77–6.82 dd, 1H (ethylenic); 6.97–7.50 m, 7H (Ar); 8.01 s, 3H ($NH_3^+$); 9.85 s, 1H (NH); 10.86 s, 1H (NH). Melting point: 169° C.

EXAMPLE 4

N-[4-(4-{2-[3-(2-Aminoethyl)-1H-indol-5-yloxy]acetyl}piperazin-1-yl)phenyl]benzamide hydrochloride

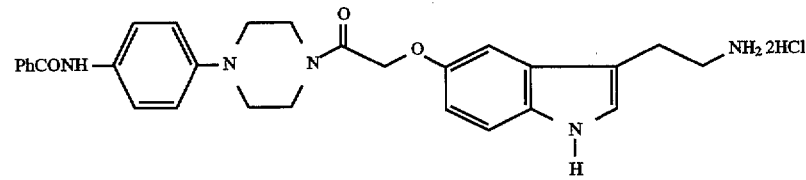

4

The compound 4 is obtained from the product 2A (700 mg, 1.42 mmol) and benzoyl chloride (0.16 ml, 1.42 mmol) according to the procedure described for the preparation of Example 3.

Purification of the product in the base form is carried out by chromatography on a column of silica gel eluted with a chloroform/methanol/aqueous ammonia (80/18.5/1.5, v/v) mixture. The pure product is isolated in the form of a yellow syrup which results, after treatment with hydrochloric acid in methanol, in the compound 4 (560 mg, 66%).

Elemental analysis ($C_{29}H_{33}N_5O_3Cl_2.2H_2O$), % calculated: C 57.43, H 6.15, N 11.55; % found: C 57.32, H 5.97, N 11.53.

1H NMR, d6-DMSO (ppm): 3.00 s, 4H ($CH_2$); 3.35–3.42 d, 4H ($CH_2$); 3.89 s, 4H ($CH_2$); 4.87 s, 2H (CO$\underline{CH_2}$O); 6.78–6.84 dd, 1H (ethylenic); 7.21–7.99 m, 12H (Ar); 8.10 s, 3H ($NH_3^+$); 10.35 s, 1H (NH); 10.86 s, 1H (NH). Melting point: 184°–185° C.

EXAMPLE 5

N-[4-(4-{2-[3-(2-Aminoethyl)-1H-indol-5-yloxy]acetyl}piperazin-1-yl)phenyl]methanesulfonamide hydrochloride

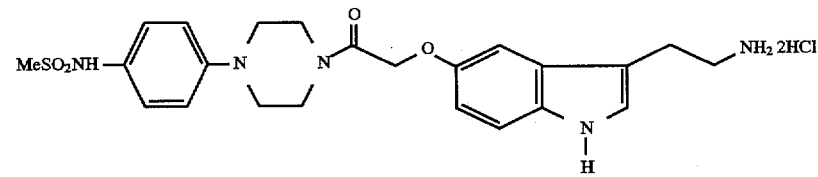

5

The compound 5 is obtained from the product 2A (201 mg, 0.407 mmol) and mehanesulfonic chloride (31 μl; 0.407 mmol) according to the procedure described for the preparation of Example 3.

Purification of the product in the base form is carried out by chromatography on a column of silica gel eluted with a chloroform/methanol/aqueous ammonia (80/18.5/1.5, v/v) mixture. The pure product is isolated in the form of a colorless syrup which results, after treatment with hydrochloric acid in methanol, in the compound 5 (151 mg, 66%).

Elemental analysis ($C_{23}H_{31}N_5O_5SCl_2.2H_2O$), % calculated: C 49.11, H 5.91, N 12.45; % found: C 49.88, H 5.73, N 11.97.

1H NMR, d6-DMSO (ppm): 2.89 s, 3H ($\underline{Me}SO_2$); 2.99–3.19 m, 8H ($CH_2$); 3.68 s, 4H ($CH_2$); 4.82 s, 2H (CO$\underline{CH_2}$O); 6.77–6.82 dd, 1H (ethylenic); 7.01–7.29 m, 7H (Ar); 8.02 s, 3H ($NH_3^+$); 9.41 s, 1H (NH); 10.85 s, 1H (NH). Melting point: 150° C.

EXAMPLE 6

N-[4-(4-{2-[3-(2-Aminoethyl)-1H-indol-5-yloxy]acetyl}piperazin-1-yl)phenyl](methanesulfonyl)methanesulfonamide hydrochloride

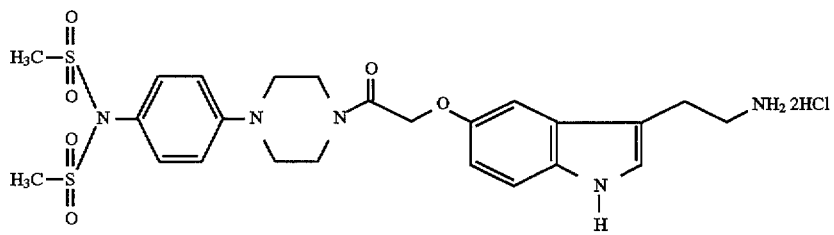

6

The product 2A (500 mg, 1.01 mmol), in solution in dichloromethane (12.5 ml) in the presence of triethylamine (0.56 ml, 4.04 mmol), is treated with mesyl chloride (0.17 ml, 2.03 mmol) at 0° C. After leaving overnight at room temperature, the mixture is diluted with dichloromethane and washed with water. The organic phase is dried over sodium sulfate, filtered and evaporated to dryness. The syrup obtained is chromatographed on a column of silica gel eluted with an ethyl acetate/dichloromethane (2/1, v/v) mixture. The pure product is obtained in the form of a colorless syrup (127 mg, 20%).

This compound is then deprotected according to the method described for the preparation of Example 2.

Purification of the product in the base form is carried out by chromatoraphy on a column of silica gel eluted with a chloroform/methanol/aqueous ammonia (80/18.5/15, v/v) mixture. The pure product is isolated in the form of a colorless syrup which results, after treatment with hydrochloric acid in mathenol, in the compound 6 (109 mg, 90%).

Elemental analysis ($C_{24}H_{33}N_5O_6S_2Cl_2$), % calculated: C 46.30, H 5.34, N 11.25; % found: C 46.47, H 5.47, N 10.96.

1HNMR, d6-DMSO (ppm): 2.99–3.90 m, 18H ($MeSO_2$—+$CH_2$); 4.83 s, 2H ($CO\underline{CH_2}O$); 6.78–6.83 dd, 1H (ethylenic); 6.97–7.33 m, 7H (Ar); 7.96 s, 3H ($NH_3^+$); 10.85 s, 1H (NH). Melting point: 202° C.

EXAMPLE 7

N-[4-(4-{2-[3-(2-Aminoethyl)-1H-indol-5-yloxy]acetyl}piperazin-1-yl)phenyl]ethanesulfonamide hydrochloride

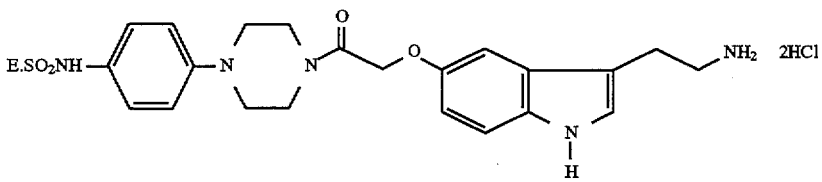

The compound 7 is obtained from product 2A (800 mg; 1.6 mmol) and ethanesulfonic chloride (0.15 ml, 1.6 mmol) according to the procedure described for the preparation of Example 3.

Purification of the product in the base form is carried out by chromatoraphy on a column of silica gel eluted with a chloroform/methanol/aqueous ammonia (80/18.5/15, v/v) mixture. The pure product is isolated in the form of an orange syrup which results, after treatment with hydrochloric acid in methanol, in the compound 7 (730 mg, 78%).

Elemental analysis ($C_{24}H_{33}N_5O_4S_1Cl_2.H_2O$), % calculated: C 50.00, H 5.95, N 12.54; % found: C 50.00, H 5.75, N 12.54.

1H NMR, d6-DMSO (ppm): 1.15–1.22 t, 3H ($CH_3$); 2.94–3.16 m, 10H ($CH_2$); 3.73 m, 4H ($CH_2$); 4.82 s, 2H ($CO\underline{CH_2}O$); 6.77–6.82 dd, 1H (ethylenic); 7.13–7.28 m, 7H (Ar); 7.99 s, 3H ($NH_3^+$); 9.55 s, 1H (NH); 10.84 s 1H (NH). Melting point: 222° C.

EXAMPLE 8

Thiophene-2-{N-[4-(4-{2-[3-(2-aminoethyl)-1H-indol-5-yloxy]acetyl}piperazin-1-yl)phenyl]sulfonamide hydrochloride

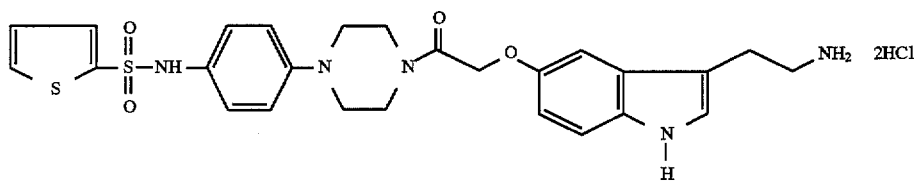

The compound 8 is obtained from the product 2A (800 mg, 1.62 =mmol) and thiophene sulfonic chloride (296 mg, 1.62 mmol) according to the procedure described for the preparation of Example 3.

Purification of the product in the base form is carried out by chromatoraphy on a column of silica gel eluted with a chloroform/methanol/aqueous ammonia (80/18.5/15, v/v) mixture. The pure product is isolated in the form of a yellow powder which results, after treatment with hydrochloric acid in methanol, in the compound 8 (575 mg, 57%).

Elemental analysis ($C_{26}H_{31}N_5O_4S_2Cl_2.H_2O$), % calculated: C 49.52, H 5.27, N 11.11; % found: C 50.44, H 5.49, N 10.86.

1H NMR, d6-DMSO (ppm): 2.99–3.16 m, 8H ($CH_2$); 3.67 s, 4H ($CH_2$), 4.81 s, 2H ($CO\underline{CH_2}O$); 6.76–6.81 dd, 1H (ethylenic indole); 7.00–7.28 m, 8H (Ar +ethylenic thiophene); 7.48 dd, 1H (ethylenic thiophene); 7.88 dd, 1H (ethylenic thiophene); 8.06 s, 3H (NH$_3^+$); 10.13 s, 1H (NH); 10.86 s, 1H (NH).

Melting point: 185° C.

EXAMPLE 9

N-[4-(4-{2-[3-(2-Aminoethyl)-1H-indol-5-yl-oxy]acetyl}piperazin-1-yl)phenyl](thiophene-2-sulfonyl)-thiophene-2-sulfonamide hydrochloride

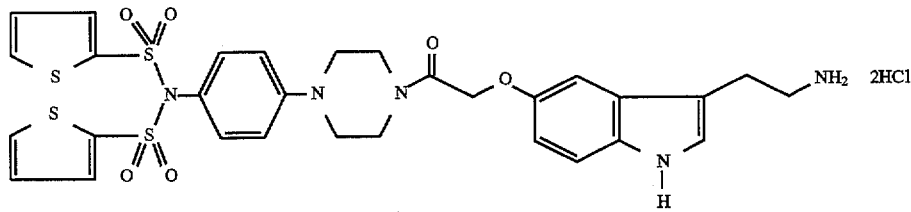

The compound 9 is obtained from the product 2A (800 mg, 1.62 mmol) and thiophene sulfonic chloride (335 mg, 1.94 mmol) according to the procedure described for the preparation of Example 6.

Purification of the product in the base form is carried out by chromatography on a column of silica gel eluted with a chloroform/methanol/aqueous ammonia (80/6.5/15, v/v) mixture. The pure product is isolated in the form of a yellow syrup which results, after treatment with hydrochloric acid in methanol, in the compound 2 (380 mg, 32%).

Elemental analysis (C$_{30}$H$_{33}$N$_5$O$_6$S$_4$Cl$_2$), % calculated: C 7.49, H 4.35, N 9.23; % found: C 47.62 H 4.40, N 9.20 H NMR, d6-DMSO (ppm): 3.00 s, 4H (CH$_2$); 3.27 s, 4H (CH$_2$), 3.63 s, 4H (CH$_2$); 4.82 s, 2H (COCH$_2$O); 6.77–7.30 m, 10H, (Ar+ethylenic); 7.70 d, 2H (ethylenic); 8.05 s, 3H (NH$_3^+$); 8.20 d, 2H (ethylenic); 10.85 s, 1H (NH).

Melting point: 180° C.

EXAMPLE 10

3,5-Dimethylisoxazole-4-{N-[4-(4-{2-[3-(2-aminoethyl)-1H-indol-5-yloxy]acetyl}-piperazin-1-yl)phenyl]sulfonamide hydrochloride

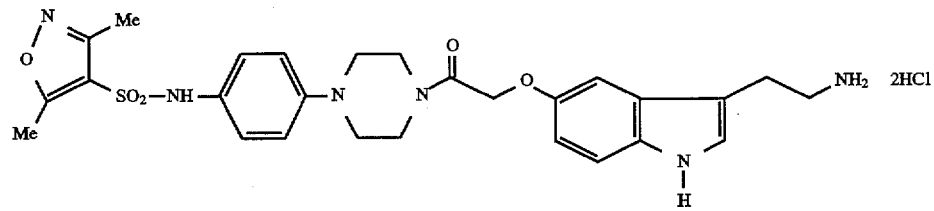

The compound 10 is obtained from the product 2A (800 mg, 1.62 mmol) and 3,5-dimmethylisoxazole-4-sulfonic chloride (317 mg, 1.62 mmol) according to the procedure described for the preparation of Example 3.

Purification of the product in the base form is carried out by chromatoraphy on a column of silica gel eluted with a chloroform/methanol/aqueous ammonia (80/18.5/1.5, v/v) mixture. The pure product is isolated in the form of a yellow syrup which results, after treatment with hydrochloric acid in ether, in the compound 10 (576 mg, 55%).

Elemental analysis (C$_{27}$H$_{34}$N$_6$O$_5$S$_1$Cl$_2$; H$_2$O), % calculated: C 50.11, H 5.67, N 12.99; % found: C 50.21, H 5.22, N 12.52.

1H NMR, d6-DMSO (ppm): 2.15 s, 3H (Me); 2.33 s, 3H (Me), 2.92–3.07 m, 8H (CH$_2$); 3.64 s, 4H (CH$_2$); 4.80 s, 3H (COCH$_2$O); 6.77–6.82 dd, 1H (ethylchic); 6.95–7.28 m, 7H (Ar); 7.88 s, 3H (NH$_3^+$); 9.98 s, 1H (NH); 10.84 s, 1H (NH).

Melting point: 193° C.

EXAMPLE 11

2-[3-(2-Aminoethyl)-1H-indol-5-yloxy]-1-[4-(4-N-{ethoxycarbonyl}aminophenyl)piperazin-1-yl]-ethanone hydrochloride

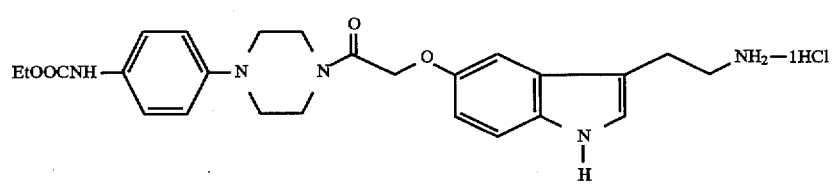

The compound 11 is obtained from the product 2A (600 mg, 1.21 mmol) and ethyl chloroformate (0.13 ml, 1.33 mmol) according to the procedure described for the preparation of Example 6.

Purification of the product in the base form is carried out by chromatoraphy on a column of silica gel eluted with a chloroform/methanol/aqueous ammonia (80/18.5/1.5, v/v) mixture. The pure product is isolated in the form of a colorless syrup which results, after treatment with hydrochloric acid in ether, in the compound 11 (230 mg, 38%).

Elemental analysis ($C_{25}H_{32}N_5O_4Cl$), % calculated: C 59.81; H 6.42, N 13.95; % found: C 60.26, H 6.52, N 13.49.

1H NMR, d6-DMSO (ppm): 1.22 t, 3H ($CH_3$); 2.81–3.03 m, 8H ($CH_2$); 3.64 s, 4H ($CH_2$); 4.03–4.14 q, 2H ($CH_2$); 4.80 s, 2H (CO$\underline{CH_2}$O); 6.75–6.80 dd, 1H (ethylchic); 6.80–7.33 m, 7H (Ar); 9.34 s, 1H (NH); 10.74 s, 1H (NH).

Melting point: 153° C.

EXAMPLE 12

2,2,2-Trifluoroethane [4-(4-{2-[3-(2-aminoethyl)-1H-indol-5-yloxy]acetyl}piperazin-1-yl)phenyl]-sulfonamide hydrochloride The compound 13 is obtained from the product 2A (800 mg, 1.62 mmol) and isopropylsulfonic chloride (0.18 ml, 1.62 mmol) according to the procedure described for the preparation of Example 3.

Purification of the product in the base form is carried out by chromatoraphy on a column of silica gel eluted with a chloroform/methanol/aqueous ammonia (80/18.5/1.5, v/v) mixture. The pure product is isolated in the form of a syrup which results, after treatment with hydrochloric acid in ether, in the compound 13 (381 mg, 41%).

1H NMR, d6-DMSO (ppm): 11.22 d, 6H (Me); 2.99–3.17 m, 9H ($CH_2$+CH); 3.73 m, 4H ($CH_2$); 4.83 s, 2H (CO$\underline{CH_2}$O); 6.78–7.03 dd, 1H (ethylenic); 7.16–7.28 m, 7H (Ar); 8.07 s, 3H ($NH_3^+$); 9.59 s, 1H (NH); 10.86 s, 1H (NH).

EXAMPLE 14

2-[3-(2-Aminoethyl)-1H-indol-5-yloxy]-1-[4-(2-nitrophenyl)piperazin-1-yl)ethanone hydrochloride

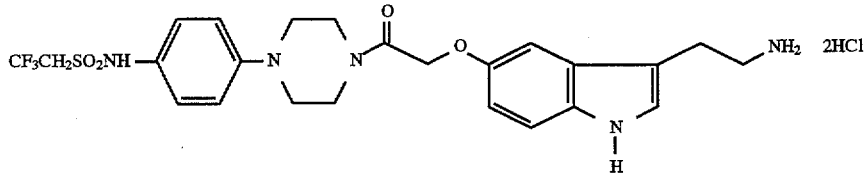

The compound 12 is obtained from the product 2A (800 mg, 1.62 mmol) and trifluoroethane sulfonic chloride (0.36 ml, 3.24 mmol) according to the procedure described for the preparation of Example 3.

Purification of the product in the base form is carried out by chromatoraphy on a column of silica gel eluted with a chloroform/methanol/aqueous ammonia (80/18.5/1.5, v/v) mixture. The pure product is obtained in the form of a green-yellow syrup which results, after treatment with hydrochloric acid in methanol, in the compound 12 (643 mg, 65%).

1H NMR, d6-DMSO (ppm): 2.99–3.16 m, 8H ($CH_2$); 3.67 s, 4H ($CH_2$), 4.82 s, 2H (COC$H_2$O); 6.76–6.82 dd, 1H (ethylenic); 6.99–7.55 m, 7H (Ar); 7.55 s, 2H ($CF_3CH_2SO_2$); 8.07 s, 3H ($NH_3^+$); 10.12 s, 1H (NH); 10.85 s, 1H (NH).

EXAMPLE 13

N-[4-(4-{2-[3-(2-Aminoethyl)-1H-indol-5-yloxy]acetyl}piperazin-1-yl)phenyl]isopropanesulfonamide hydrochloride

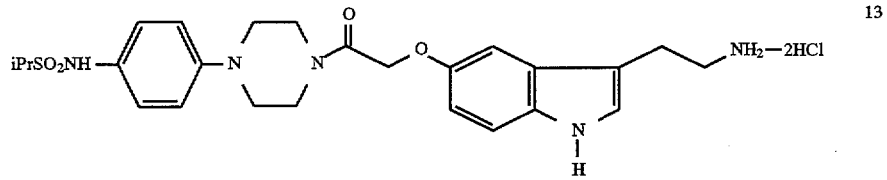

14

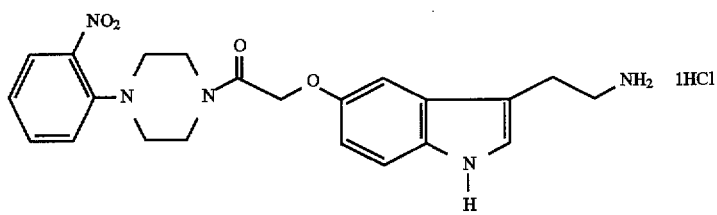

The compound 14 is obtained from (2-nitrophenyl) piperazine (15 g, 72.5 mmol), chloroacetyl chloride (5.78 ml, 72.56 mmol) and the compound 1A (10.9 g, 39.6 mmol) according to the procedure described for the preparation of Example 1.

Purification of the product in the base form is carried out by chromatoraphy on a column of silica gel eluted with a chloroform/methanol/aqueous ammonia (80/19/1, v/v) mixture. The pure product is isolated in the form of a yellow syrup which results, after treatment with hydrochloric acid in ether, in the compound 14 (22 g, 67%).

Elemental analysis ($C_{22}H_{26}N_5O_4Cl.13H_2O$), % calculated: C 54.67, H 5.96, N 14.49, Cl 7.33; % found: C 54.63, H 5.74, N 14.25, Cl 7.65.

1H NMR, d6-DMSO. (ppm): 3.00 m, 8H ($CH_2$); 3.63 s, 4H ($CH_2$), 4.81 s, 2H ($COCH_2O$); 6.78–6.83 dd, 1H (ethylenic); 7.15–7.87 m, 7H ($\overline{Ar}$); 8.00 s, 3H ($NH_3^+$); 10.85 s, 1H (NH).

Melting point: 130° C.

EXAMPLE 15

2-[3-(2-Aminoethyl)-1H-indol-5-yloxy]-1-[4-(4-nitrophenyl)piperazin-1-yl)ethanethione hydrochloride

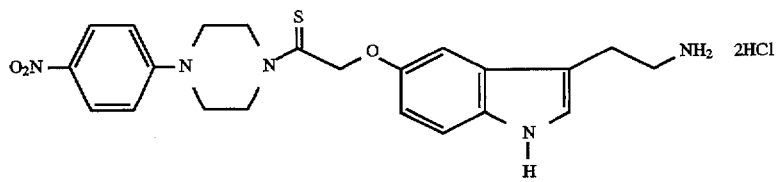

The compound 1, in the base form (600 mg, 1.42 mmol), in solution in toluene (12 ml) in the presence of Lawesson's reagent (401 mg, 0.99 mmol), is heated at reflux for 3 hours. The mixture is brought back to room temperature, diluted with dichloromethane and washed with water (twice). The organic phase is dried over sodium sulfate, filtered and evaporated to dryness. The syrup obtained is chromatoraphed on a column of silica gel eluted with a chloroform/methanol/aqueous ammonia (80/18.5/1.5, v/v) mixture. The pure product is isolated in the form of a syrup which results, after treatment with hydrochloric acid in ether, in the compound 15 (378 mg, 52%).

EXAMPLE 16

2-[3-(2-Aminoethyl)-1H-indol-5-yloxy]-1-[4-(4-(hydroxyamino)phenyl)piperazin-1-yl)ethanone hydrochloride

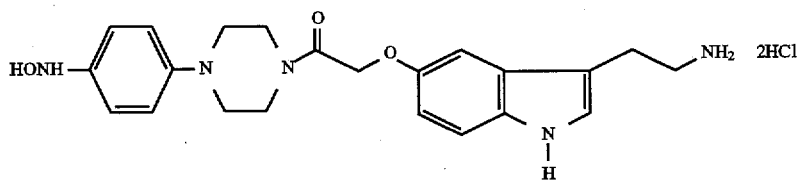

The compound 1C, (5 g, 9.54 mmol), in solution in THF (120 ml) in the presence of a catalytic amount of Rhodium-on-alumina (490 mg, 0.48 mmol), is treated at 0° C. with hydrazine hydrate (1.16 ml, 23.8 mmol). The mixture is stirred at room temperature for 4 hours and the catalyst is then filtered off on celite; the mixture is diluted with dichloromethane and washed with water. The organic phase is dried with sodium sulfate, filtered and evaporated to dryness. The syrup obtained is chromatographed on a column of silica gel eluted with a dichloromethane/ethyl acetate (5/1 and then 2/1, v/v) mixture. The pure product is obtained in the form of a green-yellow syrup.

This product is then deprotected according to the method described for the preparation of Example 2.

Purification of the product in the base form is carried out by chromatography on a column of silica gel eluted with a chloroform/methanol/aqueous ammonia (90/9.5/0.5, v/v) mixture. The pure product is isolated in the form of a syrup which results, after treatment with hydrochloric acid in ether, in the compound 16 (780 mg, 21%).

EXAMPLE 17

2-{5-[4-(4-Nitrophenylpiperazine-1-sulfonylmethoxy]-1H-indol-3-yl}ethylamine hydrochloride

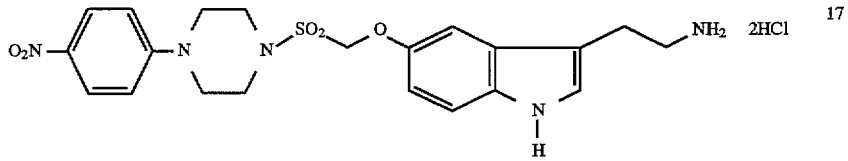

The compound 17 is obtained from (4-nitrophenyl) piperazine (1 g, 4.82 mmol), chloromethanesulfonyl chloride (719 mg, 4.82 mmol) and the compound 1A (739 mg, 2.63 mmol) according to the procedure described for the preparation of Example 1. The pure product is isolated in the form of a syrup which results, after treatment with hydrochloric acid in ether, in the compound 17 (420 mg, 30%).

EXAMPLE 18

2-[3-(2-Aminoethyl)-1H-indol-5-yloxy]-1-[4-(4-nitrophenyl)piperazin-1-yl]propane-1-one hydrochloride

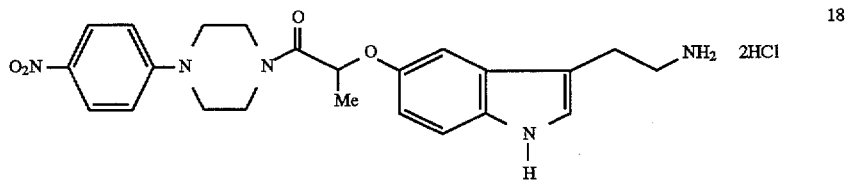

The compound 18 is obtained from (4-nitrophenyl) piperazine (1 g, 4.82 mmol), α-methylchloroacetyl chloride (0.46 ml, 4.82 mmol) and the compound 1A (739 mg, 2.63 mmol) according to the procedure described for the preparation of Example 1. The pure product is isolated in the form of a syrup which results, after treatment with hydrochloric acid in ether, in the compound 18 (470 mg, 35%).

EXAMPLE 19

2-[3-(2-(Dimethylamino)ethyl)-1H-indol-5-yloxy]-1-[4-(4-nitrophenyl)piperazin-1-yl]ethanone hydrochloride

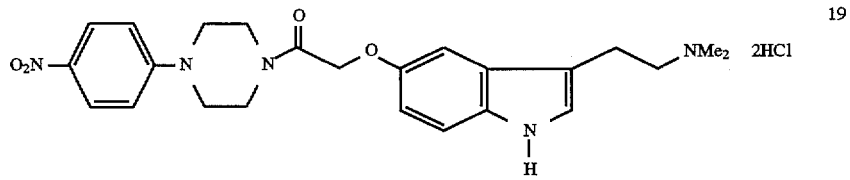

The compound 19 is obtained from (4-nitrophenyl) piperazine (200 mg, 0.96 mmol), chloroacetyl chloride (76 ml, 0.96 mmol) and bufotenine (108 mg, 0.53 mmol) according to the procedure described for the preparation of Example 1. The pure product is isolated in the form of a syrup which results, after treatment with hydrochloric acid in ether, in the compound 19 (69 mg, 25%).

EXAMPLE 20

2-[3-(2-Aminoethyl)-1H-indol-5-yloxy]-1-[4-(4-(dimethylamino)phenyl)piperazin-1-yl]ethanone hydrochloride

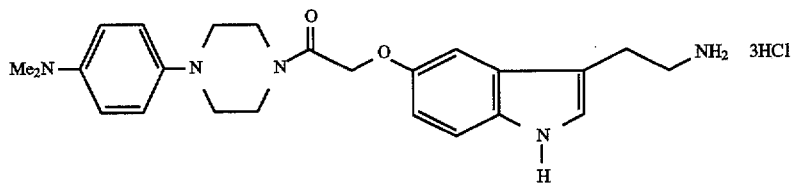

The product 2A (800 mg, 1.62 mmol), in solution in tetrahydrofuran (27 ml) in the presence of tetrabutylammonium bromide (157 mg, 0.486 mmol) and of sodium hydroxide solution (6N) (2.7 ml, 16.2 mmol), is treated with dimethyl sulfate (0.61 ml, 6.48 mmol). After stirring for 2 h 30 at room temperature, the mixture is diluted with dichloromethane and washed with water. The organic phase is dried over sodium sulfate, filtered and evaporated to dryness.

The syrup obtained is chromatoraphed on a column of silica gel eluted with a dichloromethane/acetone (4/1, v/v) mixture.

This product is then deprotected according to the method described for the preparation of Example 2.

The pure product is isolated in the form of a syrup which results, after treatment with hydrochloric acid in ether, in the compound 20 (344 mg, 40%).

Elemental analysis: ($C_{28}H_{32}N_5O_4SCl.1.2H_2O$), % calculated: C 56.83, H 5.86, N 11.84; % found: C 56.66, H 5.56, N 11.67.

1H NMR, d6-DMSO (ppm): 2.98–3.02 m, 8H ($CH_2$); 3.60 m, 4H ($CH_2$); 4.79s, 2H ($COCH_2O$); 6.75–7.72 m, 13 H (Ar+ethylenic); 7.99 s, 3H ($NH_3^+$); 9.90 s, 1H (NH); 10.84 s, 1H (NH).

Melting point: 263° C.

EXAMPLE 22

2-[3-(2-Aminoethyl)-1H-indol-5-yloxy]-1-[4-(2-methoxy-4-nitrophenyl)piperazin-1-yl]ethanone hydrochloride

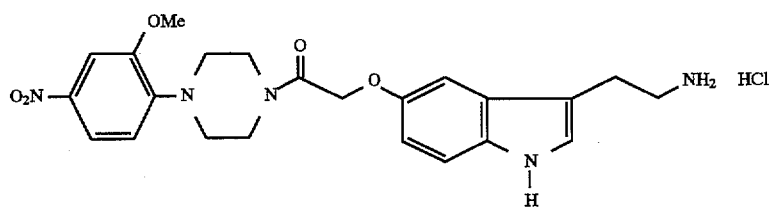

EXAMPLE 21

N-[4-(4-{2-[3-(2-Aminoethyl)-1H-indol-5-yl-oxy]acetyl}piperazin-1-yl)phenyl]benzenesulfonamide hydrochloride The compound 22 is obtained from (2-methoxy-4-nitrophenyl)piperazine (1.64 g, 6.92 mmol), chloroacetyl chloride (0.55 ml, 6.92 mmol) and the compound 1A (1.06 g, 3.8 mmol) according to the procedure described for the preparation of Example 1. Purification of the product in the base form is carried out by chromatoraphy on a column of silica gel eluted with a chloroform/methanol/aqueous

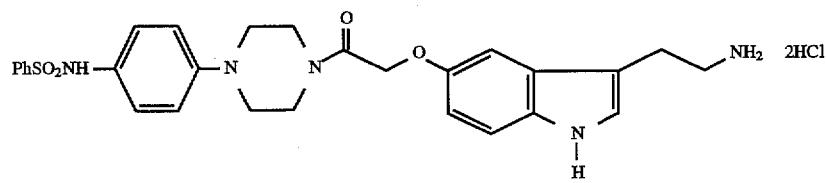

The compound 21 is obtained from the product 2A (800 mg, 1.62 mmol) and benzenesulfonic chloride (0.21 ml, 1.62 mmol) according to the procedure described for the preparation of Example 3.

Purification of the product in the base form is carried out by chromatoraphy on a column of silica gel eluted with a chloroform/methanol/aqueous ammonia (80/18.5/1.5, v/v) mixture. The pure product is isolated in the form of a syrup which results, after treatment with hydrochloric acid in ether, in the compound 21 (450 mg, 47%).

ammonia (80/19/1, v/v) mixture. The pure product is isolated in the form of a yellow syrup which results, after treatment with hydrochloric acid in ether, in the compound 22 (747 mg, 71%).

Elemental analysis 1H NMR, d6-DMSO (ppm):

EXAMPLE 23

2-(5-{2-[4-(4-Nitrophenyl)piperazin-1-yl]-ethoxy}-1H-indol-3-yl)ethylamine hydrochloride

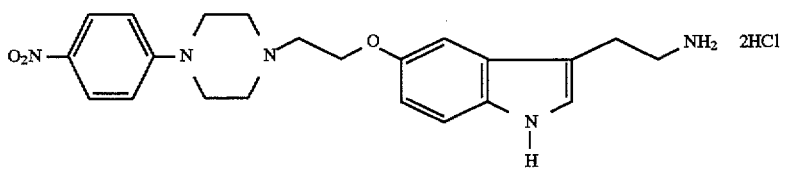

EXAMPLE 23A

2-[5-(2-Chloroethoxy)-1H-indol-3-yl]-N-(tert-butoxycarbonyl)aminoethyl

The product 1A (5 g, 18.09 mmol), in solution in methyl ethyl ketone (25 ml) in the presence of potassium carbonate (15 g, 108.5 mmol), is treated with 1-bromo-2-chloroethane. After 24 hours at reflux, the mixture is diluted with dichloromethane, filtered through celite and evaporated to dryness. The brown syrup obtained is chromatographed on a column of silica gel eluted with a dichloromethane/acetone (30/1, v/v) mixture. The pure product is obtained in the form of white crystals (5.2 g, 84%).

Elemental analysis ($C_{17}H_{23}N_2O_3Cl$), % calculated: C 60.26, H 6.84, N 8.27; % found: C 60.37, H 6.98, N 8.21.

1H NMR, $CDCl_3$ (ppm): 1.46 s, 9H (t-Bu); 2.88–2.95 t, 2H ($CH_2$); 3.45 m, 2H ($CH_2$); 3.81–3.87 t, 2H ($CH_2$); 4.26–4.32 t, 2H ($CH_2$); 4.65 s, 1H (NH); 6.87–6.93 dd, 1H (ethylenic); 7.01–7.29 m, 3H (Ar); 8.16 s, 1H (NH).

Melting point: 129° C.

EXAMPLE 23B 2-(5-{2-[4-(4-Aminophenyl)piperazin-1-yl]-ethox}-1H-indol-3-yl)ethylamine hydrochloride A mixture of the product 23A (1.03 g, 3.07 mmol) and (4-nitrophenyl)piperazine (636 mg, 3.07 mmol) in dimethylformamide (1.5 ml) in the presence of potassium carbonate (1.27 g, 9.3 mmol) and potassium iodide (166 mg, 0.3 mmol) is heated at 80° C. for 31 hours. The mixture is then diluted with ethyl acetate and washed with water and then with a saturated sodium chloride solution. The organic phase is dried over sodium sulfate, filtered and evaporated to dryness. The yellow solid obtained is purified on a column of silica gel eluted with a dichloromethane/methanol (30/1, v/v) mixture. The pure product is isolated in the form of a yellow solid (1.46 g, 94%).

This product is deprotected according to the method described for the preparation of Example 2. The product is chromatographed on a column of silica gel eluted with a dichloromethane/methanol/aqueous ammonia (80/18.5/1.5, v/v) mixture.

The pure product is isolated in the form of a yellow syrup which results, after treatment with hydrochloric acid in ether, in the compound 23 (1.17 g, 78%).

Elemental analysis ($C_{22}H_{29}N_5O_3Cl_2 \cdot 1.5H_2O$), % calculated: C 51.87, H 6.33, N 13.75; % found: C 52.41, H 6.18, N 13.68.

1H NMR, d6-DMSO (ppm): 3.01–3.58 m, 12H ($CH_2$); 4.19 m, 2H ($CH_2$); 4.48 m, 2H ($CH_2$); 6.79–6.84 dd, 1H (ethylenic); 7.11–7.31 m, 5H (Ar); 8.09–8.13 m, 5H (Ar+ $NH_3^+$); 10.91 s, 1H (NH); 11.74 s, 1H ($NH^+$).

Melting point: 148° C.

EXAMPLE 24

3-[3-(2-aminoethyl)-1H-indol-5-yl]-1-[4-(4-nitrophenyl)piperazin-1-yl]prop-2-en-1-one hydrochloride

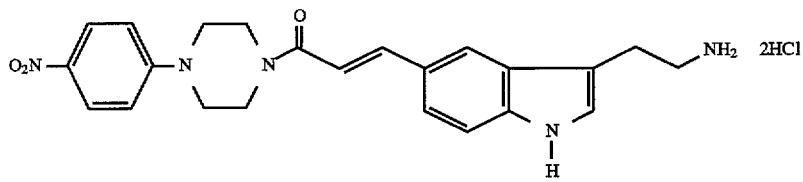

EXAMPLE 24A 2-(5-bromo-1H-indol-3-yl)-N-(tert-butoxycarbonyl) ethylamine

5-Bromotryptamine (43 g, 180 mmol), in solution in tetrahydrofuran (500 ml) in the presence of sodium hydroxide solution (2N) (260 ml), is treated with di-tert-butyl dicarbonate (60 g, 275 mmol) at room temperature.

After stirring overnight at room temperature, the mixture is diluted with ethyl acetate and washed with water and then with a saturated sodium chloride solution. The organic phase is dried over sodium sulfate, filtered and evaporated to dryness. The syrup obtained is chromatographed on a column of silica gel eluted with a toluene/ethyl acetate (80/20, v/v) mixture. The pure product is obtained in the form of a syrup which crystallizes from petroleum ether to give a beige powder (27 g, 44%).

Melting point: 103° C.

EXAMPLE 24B

Methyl 3-[3-(2-(N-tert-butoxycarbonylamino)ethyl)-1H-indol-5-yl]acrylate

The product 24A (5 g, 14.7 mmol) is heated in the presence of methyl acrylate (2 ml, 22.1 mmol), trethylamine (10 ml), tri-o-tolylphosphine (90 mg, 0.29 mmol) and palladium acetate (33 mg, 1.47 mmol) at 100° C. in a long narrow cylindrical bottle with a screw top. After stirring overnight, the same amounts of tri-o-tolylphosphine and palladium acetate are added. After 5 hours, the mixture is diluted with ethyl acetate and the precipitate formed is filtered off on celite. The filtrate is washed with water and then with a saturated sodium chloride solution. The organic phase is dried over sodium sulfate, filtered and evaporated to dryness. The syrup obtained is chromatographed on a column of silica gel eluted with a dichloromethane/ethyl acetate (15/1 then 10/1, v/v) mixture. The pure product is obtained in the form of a pale yellow syrup (4.36 g, 86%).

Elemental analysis ($C_{19}H_{24}N_2O_4$), % calculated: C 66.26, H 7.02, N 8.13; % found: C 65.40, H 6.74, N 7.79.

1H NMR, $CDCl_3$ (ppm): 1.44 s, 9H (t-Bu); 2.92–2.99 m, 2H ($CH_2$); 3.45–3.48 m, 2H ($CH_2$); 3.82 s, 3H (COO$\underline{Me}$); 4.64 s, 1H (NH); 6.39–6.47 d, 1H (ethylenic); 7.05–7.89 m, 5H (Ar+ethylenics); 8.31 s, 1H (NH).

EXAMPLE 24C

3-[3-(2-N-{tert-butoxycarbonyl}aminoethyl)-1H-indol-5-yl]acrylic acid

The product 24B (2 g, 5.80 mmol), in solution in ethanol (20 ml) and water (0.2 ml), is treated with potassium hydroxide pellets (650 mg, 11.6 mmol). After 3 hours at reflux, the mixture is diluted with ethyl acetate and washed with a normal hydrochloric acid solution, with water and then with a saturated sodium chloride solution. The organic phase is dried over sodium sulfate, filtered and evaporated to dryness. The product 24C is obtained pure in the form of a white powder (1.85 g, 97%).

Melting point: 179°–181° C.

EXAMPLE 24

3-[3-(2-Aminoethyl)-1H-indol-5-yl]-1-[4-(4-nitrophenyl)piperazin-1-yl]prop-2-en-1-one hydrochloride The product 24C (500 mg, 1.51 mmol), in solution in anhydrous dichloromethane (18 ml) in the presence of N-methylmorpholine ([illegible] ml, 1.66 mmol), is treated at –15° C., under nitrogen, with ethyl chloroformate (0.16 ml, 1.66 mmol). After stirring for 15 minutes at –10° C., (4-nitrophenyl)piperazine (781 mg, 3.77 mmol) is added and the mixture is stirred from –10° C. to room temperature for 1 hour. The mixture is then diluted with dichloromethane and washed with a saturated sodium bicarbonate solution, with water and then with a saturated sodium chloride solution. The organic phase is dried over sodium sulfate, filtered and evaporated to dryness. The syrup obtained is chromatographed on a column of silica gel eluted with a dichloromethane/methanol (40/1, v/v) mixture. The pure product is isolated in the form of a syrup (564 mg, 72%). This product is then deprotected according to the method described for the preparation of Example 2.

The pure product is isolated in the form of a syrup which results, after treatment with hydrochloric acid in ether, in the compound 24 (277 mg, 50%).

EXAMPLE 25

3-[3-(2-Aminoethyl)-1H-indol-5-yl]-1-[4-(4-nitrophenyl)piperazin-1-yl]propan-1-one hydrochloride

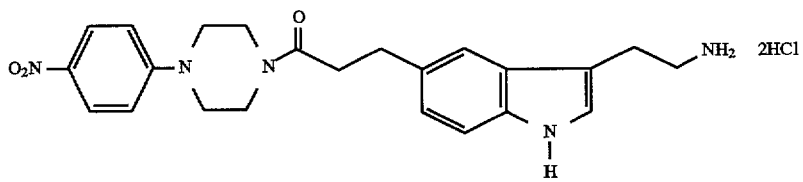

EXAMPLE 25A

3-[3-(2-N-{tert-butoxycarbonyl}aminoethyl)-1H-indol-5-yl]proplonic acid

The product 24C (500 mg, 1.51 mmol), in solution in methanol (4 ml) in the presence of a catalytic amount of palladium-on-charcoal (30 mg), is hydrogenated by hydrogen gas. After 1 h 30 at room temperature, the mixture is diluted with dichloromethane, filtered through celite and evaporated to dryness. The pure product is obtained by recrystallization from ether to give a beige powder (483 mg, 96%).

Elemental analysis ($C_{18}H_{24}N_2O_4$), % calculated: C 65.04, H 7.28, N 8.43: % found: C 64.57, H 7.35, N 8.25.

1H NMR, d6-DMSO (ppm): 1.38 s, 9H (t-Bu); 2.50–3.40 m, 8H ($CH_2$); 6.87–7.32 m, 4H (Ar +ethylenic); 10.68 s, 1H (NH); 12.05 s, 1H (NH).

EXAMPLE 25

3-[3-(2-Aminoethyl)-1H-indol-5-yl]-1-[4-(4-nitrophenyl)piperazin-1-yl]propan-1-one hydrochloride The compound 25 is obtained from the compound 25A (640 mg, 1.92 mmol) and 4-nitrophenylpiperazine (981 mg, 4.73 mmol) according to the method described for the preparation of Example 24 from 24C. The pure product is obtained in the form of a syrup which results, after treatment with hydrochloric acid in ether, in the compound 25 (531 mg, 56%).

Elemental analysis ($C_{23}H_{29}Cl_2N_5O_3 \cdot 1.7H_2O$), % calculated: C 52.62, H 6.22, N 13.34, Cl 13.50; % found: C 52.56, H 5.93, N 13.16, Cl 14.72.

1H NMR, d6-DMSO (ppm): 2.69 m, 2H; 2.88–3.00 m, 6H; 3.42 m, 4H; 3.60 broad s, 4H; 6.94–7.42 m, 6H; 8.05 d, 2H; 8.14 s, 3H; 10.88 s, 1H.

Melting point: 145° C.

EXAMPLE 26

N-[4-(4-{2-[3-(2-Aminoethyl)-1H-indol-5-yloxy]acetyl}piperazin-1-yl)phenyl]-4-nitrophenylsulfonamide hydrochloride

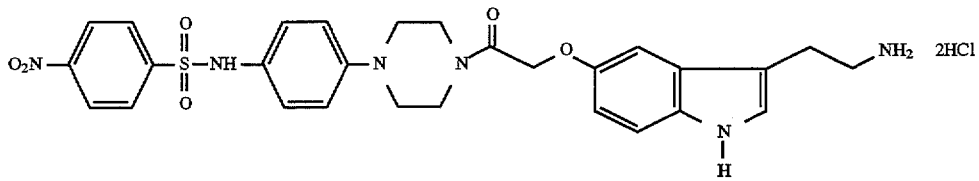

Method A

The compound 26 is obtained from the product 2A (768 mg, 1.55 mmol) and 4-nitrobenzenesulfonyl chloride (689 mg, 3.10 mmol) according to the procedure described for the preparation of Example 3.

Purification of the product, in the base form, is carried out by chromatography on a column of silica gel eluted with a dichloromethane/methanol/aqueous ammonia (80/18.5/1.5, v/v) mixture. The pure product is isolated in the form of a pale yellow syrup which results, after treatment with hydrochloric acid in ether, in the compound 26 (391 mg, 44%).

Elemental analysis ($C_{28}H_{32}N_6O_6S_1$—2.5$H_2O$), % calculated: C 48.28, H 5.35, N 12.06, Cl 10.18, % found: C 48.09, H 5.05, N 11.84, Cl 9.85.

1H NMR, d6-DMSO (ppm): 2.96–3.14 m, 8H; 3.62 m, 4H; 4.78 s, 2H; 6.73–6.79 dd, 1H; 6.95–7.26 m, 7H; 7.89–7.94 m, 5H; 8.33–8.37 d, 2H; 10.31 s, 1H; 10.83 s, 1H.

Melting point: 190° C.

Mass spectrum (DCI/NH$_3$): m/z 579 (M+H).

Method B 26A-4-(4-(tert-Butoxycarbonyl)piperazin-1-yl)phenylamine 1-(4-Nitrophenyl)piperazine (50 g, 241.2 mmol), in solution in dichloromethane (1 l) in the presence of triethylamine (50.3 ml, 361.8 mmol), is treated with di-tert-butyl dicarbonate (63.2 g, 289.4 mmol) at room temperature for 1 hour. The mixture is then diluted with dichloromethane and washed with water. The organic phase is dried over sodium sulfate, filtered and evaporated to dryness.

The crude product obtained is taken up in methanol and is hydrogenated at atmospheric pressure in the presence of a catalytic amount of (5%) palladium-on-charcoal (2 g, 0.94 mmol).

After stirring for 28 h at room temperature, the mixture is filtered through celite and evaporated to dryness. The syrup obtained is chromatographed on a column of silica gel eluted with a hexane/ethyl acetate (1/1, v/v) mixture. The pure product is isolated in the form of a pale pink powder (57 g, 85%).

Elemental analysis ($C_{15}H_{25}N_3O_2$), % calculated: C 64.95, H 8.35, N 15.14; % found: C 64.95, H 8.31, N 14.89.

1H NMR, d6-DMSO (ppm): 1.42 s, 9H; 2.83 t, 4H; 3.42 t, 4H; 4.62 s, 2H; 6.49 d, 2H; 6.70 d, 2H.

Melting point: 96° C.

26B—N-[4-(4-(tert-Butoxycarbonyl)piperazin-1-ylphenyl)-4-nitrobenzenesulfonamide The compound 26A (37.6 g, 135.5 mmol), in a solution of dichloromethane (1 l) in the presence of triethylamine (20.7 ml, 149.1 mmol), is treated at 0° C. with 4-nitrobenzenesulfonyl chloride (30.04 g, 135.5 mmol).

After stirring for 3h 30 from 0° C. to room temperature, 4-nitrobenzenesulfonyl chloride (9.1 g; 40.6 mmol) is again added. After 2 h 30, the reaction mixture is diluted with dichloromethane, washed with water, dried over sodium sulfate, filtered and evaporated to dryness. The dark green syrup obtained is taken up in methanol while hot and then cooled in order to obtain crystallization of the expected product, which is isolated by filtration on a büchner and washing with ether. A yellow powder (50 g, 80%) is obtained, which powder is used straight away in the following reaction.

26C—4-Nitro-N-(4-(piperazin-1-yl)phenyl)benzenesulfonamide

The above product (50 g, 108.1 mmol), in solution in toluene (1.3 l), is treated at room temperature with trifluoroacetic acid (180 ml). After 3 h 30, the mixture is evaporated to dryness and coevaporated 5 times with toluene. The syrup obtained is purified on a silica column eluted with a dichloromethane/methanol/aqueous ammonia (90/9.5/0.5, v/v) and then (85/14/1, v/v) mixture. The product 26C and isolated in the form of a pale yellow powder (29 g, 75%).

1H NMR, d6-DMSO (ppm): 3.20 m, 8H; 6.88 m, 4H; 7.93 d, 2H; 8.37 d, 2H; 9.29 s, 1H.

Melting point: 240° C.

26D—N-[4-(4-{2-[3-(2-{N-tert-Butoxycarbonyl}aminoethyl)-1H-indol-5-yloxy]acetyl}piperazin-1-yl)phenyl]-4-nitrophenylsulfonamide

[3-(2-{N-tert-Butoxycarbonyl}aminoethyl)-1H-indol-5-yloxy]acetic acid (1 g, 2.99 mmol), prepared according to a method described above (Patent Application FR 2699918-A), in solution in anhydrous dichloromethane (50 ml) in the presence of N-methylmorpholine (0.45 ml, 4.5 mmol), is treated at −15° C. and under nitrogen with ethyl chloroformate (0.37 ml, 3.9 mmol).

After stirring for 30 minutes, the compound 26C (2.2 g, 6.0 mmol) is added and the mixture is stirred from −15° C. to room temperature for 4 hours. The mixture is diluted with ethyl acetate and washed with a saturated sodium bicarbonate solution, then with water and finally with a saturated sodium chloride solution. The organic phase is dried over sodium sulfate, filtered and evaporated to dryness.

The syrup obtained is chromatographed on a column of silica gel eluted with a dichloromethane/ethyl acetate (2/1 then 1/1, v/v) mixture. The product 26D is isolated in the form of a pale yellow powder (1.3 g, 65%).

Elemental analysis ($C_{33}H_{38}N_6O_8$), % calculated: C 58.39, H 5.64, N 12.38; % found: C 58.49, H 5.61, N 12.03.

1H NMR, d6-DMSO (ppm): 1.34 s, 9H; 2.70 t, 2H; 3.09 m, 6H; 3.57 s, 4H; 4.74 s, 2H; 6.71–7.21 m, 9H; 7.89 d, 2H; 8.34 d, 2H; 10.16 s, 1H; 10.63 s, 1H.

Melting point: 237° C.

26—N-[4-(4-{2-[3-(2-Aminoethyl)-1H-indol-5-yloxy]-acetyl}piperazin-1-yl)phenyl]-4-nitrophenylsulfonamide hydrochloride The compound 26D (2.76 g, 4.06 mmol), in suspension in toluene (82 ml), is treated at room temperature with trifluoroacetic acid (11 ml). After stirring for 3 h, the mixture is evaporated to dryness and coevaporated 4 times with toluene. The syrup obtained is chromatographed on a column of silica gel eluted with a dichloromethane/methanol/aqueous ammonia (85/14/1, v/v) mixture. The pure product is isolated in the form of an orangey-yellow syrup which results, after treatment with hydrochloric acid in ether, in the compound 26 (2.38 g, 90%).

The examples 27 to 34 are prepared according to the method described for the preparation of Example 3 from 2A.

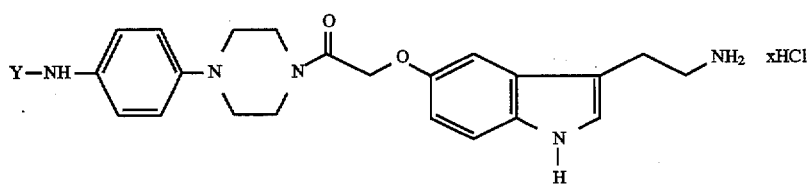

| Examples | Y | Reactants | Base/solvents/T °C. | Yd (%) | M.p. (°C.) | Empirical formulae |
|---|---|---|---|---|---|---|
| 27 | CH₃O-C(=O)-CH₂- | CH₃O-C(=O)-CH₂-Cl | Et₃N/CH₂Cl₂/50° C. | 16 | 244 | $C_{24}H_{29}N_5O_4 \cdot 2HCl$ |
| 28 | PhCH₂-C(=O)- | PhCH₂-C(=O)-Cl | Et₃N/CH₂Cl₂/25° C. | 31 | 176 | $C_{30}H_{33}N_5O_3 \cdot 2HCl$ |
| 29 | 2-MeO-C₆H₄-C(=O)- | 2-MeO-C₆H₄-C(=O)-Cl | pyridine/25° C. | 46 | 192 | $C_{30}H_{33}N_5O_4 \cdot 2HCl$ |
| 30 | F₃C-C(=O)- | (CF₃CO)₂O | Et₃N/CH₂Cl₂/25° C. | 20 | 183 | $C_{24}H_{26}N_5O_3F_3 \cdot 2HCl$ |
| 31 | Me₂N-SO₂- | Me₂N-SO₂Cl | pyridine/25° C. | 47 | 170 | $C_{24}H_{32}N_6O_4S_1 \cdot 2HCl$ |
| 32 | 2-thienyl-C(=O)- | 2-thienyl-C(=O)-Cl | pyridine/25° C. | 51 | 234 | $C_{27}H_{29}N_5O_3S_1 \cdot 2HCl$ |
| 33 | PhO-C(=O)- | PhO-C(=O)-Cl | Et₃N/CH₂Cl₂/25° C. | 28 | 167 | $C_{29}H_{31}N_5O_4 \cdot 2HCl$ |
| 34 | 4-O₂N-C₆H₄-C(=O)- | 4-O₂N-C₆H₄-C(=O)-Cl | pyridine/25° C. | 45 | 190 | $C_{29}H_{30}N_6O_5 \cdot 2HCl$ |

EXAMPLE 35

3-[3-(2-Aminoethyl)-1H-indol-5-yl]-1-[4-(4-aminophenyl)piperazin-1-yl]propan-1-one hydrochloride

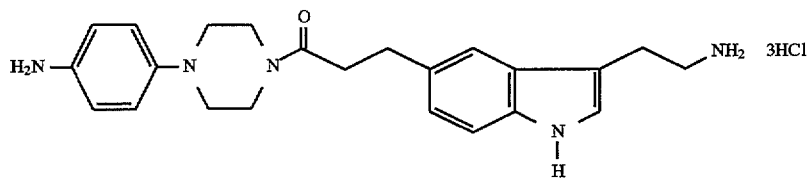

35

35A—3-[3-(2-{N-tert-Butoxycarbonyl}aminoethyl)-1H-indol-5-yl]-1-[4-(4-aminophenyl)piperazin-1-yl]propan-1-one The compound 35A is prepared from the compound 25 (5.8 g, 11.1 mmol) under the conditions described for the preparation of Example 2 from 1C. The pink foam obtained (5.24 g, 96%) is used in the crude state in the following reaction.

35—3-[3-(2-Aminoethyl)-1H-indol-5-yl]-1-[4-(4-aminophenyl)piperazin-1-yl]propan-1-one hydrochloride The product 35A (575 mg, 1.17 mmol) is then deprotected according to the method described for the preparation of Example 2 from 2A.

Purification of the product, in the base form, is carried out by chromatography on a column of silica gel eluted with a chloroform/methanol/aqueous ammonia (80/18/2, v/v) mixture. The pure product is isolated in the form of a colorless syrup which results, after treatment with hydrochloric acid in ether, in the compound 35 in the form of a pinkish powder (330 mg, 72%).

Elemental analysis ($C_{23}H_{32}Cl_3N_5O.H_2O$), % calculated: C 53.24, H 6.60, N 13.50, Cl 20.50; % found: C 53.40; H 6. [illegible], N 13.53; Cl 18.84.

1H NMR d6-DMSO (ppm): 2.70 t, 2H; 2.88–3.13 m, 10H; 3.63 s, 4H; 4.70 broad s, 3H; 6.97–7.42 m, 8H; 8.15 s, 3H; 10.90 s, 1H.

Melting point: 189° C.

EXAMPLE 36

N-[4-(4-{3-[3-(2-Aminoethyl)-1H-indol-5-yl]-propionyl}piperazin-1-yl)phenyl]methanesulfonamide hydrochloride

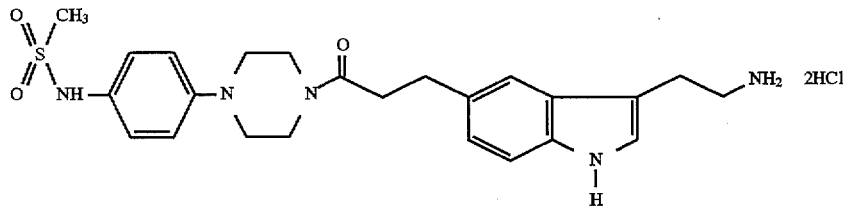

36

The compound 36 is prepared from the compound 35A (1.2 g, 2.43 mmol) and mesyl chloride (0.188 ml, 2.43 mmol) according to the method described for the preparation of Example 3.

Purification of the product in the base form is carried out by chromatography on a column of silica gel eluted with a chloroform/methanol/aqueous ammonia (80/18/2, v/v) mixture. The pure product is isolated in the form of a pale yellow syrup which results, after treatment with hydrochloric acid in ether, in the compound 36 in the form of a beige powder (1.06 g, 77%).

Elemental analysis ($C_{24}H_{33}Cl_2N_5O_3S_1.H_2O$), % calculated: C 51.43, H 6.29, N 12.49, Cl 12.65; % found: C 51.66, H 6.29, N 12.38, Cl 10.59.

1HNMR, d6-DMSO (ppm): 2.70 t, 2H; 2.87–3.15 m, 13H; 3.73 s, 4H; 6.99 d, 1H; 7.18–7.42 m, 7H; 8.13 s, 3H; 9.70 s, 1H; 10.89 s, 1H.

Melting point: 179° C.

Mass spectrum (DCI/NH$_3$): m/z 470 (M+H)

EXAMPLE 37

N-[4-(4-{3-[3-(2-Aminoethyl)-1H-indol-5-yl]propionyl}piperazin-1-yl)phenyl]-N-dimethylsulfonurea hydrochloride

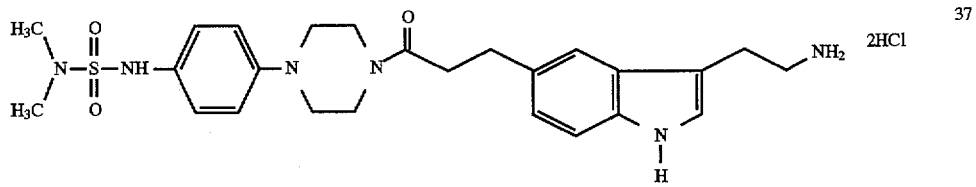

The compound 37 is prepared from the compound 35A (1.2 g, 2.43 mmol) and dimethylsulfamoyl chloride (0.39 ml, 3.64 mmol) according to the method described for the preparation of Example 3.

Purification of the product in the base form is carried out by chromatography on a column of silica gel eluted with a dichloromethane/methanol/aqueous ammonia (85/14/1, v/v) mixture. The pure product is isolated in the form of a colorless syrup which results, after treatment with hydrochloric acid in ether, in the compound 37 in the form of a beige powder (580 mg, 60%).

Elemental analysis ($C_{25}H_{36}Cl_2N_6O_3S_1.1.1H_2O$), % calculated: C 50.77, H 6.51, N 14.21, Cl 11.99; % found: C 50.74, H 6.60, N 13.89, Cl 10.61.

1H NMR, d6-DMSO (ppm): 2.66–2.75 m, 8H; 2.88–3.16 m, 10H; 3.76 broad s, 4H; 7.00 d, 1H; 7.15–7.29 m, 6H; 7.43 s, 1H; 8.11 s, 3H; 9.91 s, 1H; 10.89 s, 1H.

Melting point: 166° C.

EXAMPLE 38

N-[4-(4-{3-[3-(2-Aminoethyl)-1H-indol-5-yl]-propionyl}piperazin-1-yl)phenyl]-4-nitrobenzenesulfonamide hydrochloride

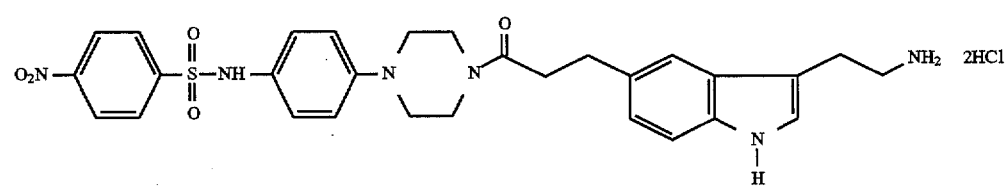

The compound 38 is prepared from the compound 35A (906 mg, 1.84 mmol) and 4-nitrobenzenesulfonyl chloride (613 mg, 2.76 mmol) according to the method described for the preparation of Example 3.

Purification of the product in the base form is carried out by chromatography on a column of silica gel eluted with a dichloromethane/methanol/aqueous ammonia (85/14/1, v/v) mixture. The pure product is isolated in the form of an orange syrup which results, after treatment with hydrochloric acid in ether, in the compound 38 in the form of an orange powder (896 mg, 71%).

Elemental analysis ($C_{29}H_{34}Cl_2N_6O_5S.2H_2O$), % calculated: C 50.80, H 5.59, N 12.26, Cl 10.34; % found: C 50.83, H 5.50, N 12.11, Cl 10.33.

1H NMR, d6-DMSO (ppm): 2.78 t, 2H; 2.90 t, 2H; 3.00–3.16 m, 8H; 3.66 broad s, 4H; 6.96–7.41 m, 8H; 7.97 d, 2H; 8.09 broad s, 3H; 8.37 d, 2H; 10.56 s, 1H; 10.88 s, 1H.

Melting point: 184° C.

EXAMPLE 39

N-[4-(4-{3-[3-(2-Aminoethyl)-1H-indol-5-yl]propionyl}piperazin-1-yl)phenyl]benzamide hydrochloride

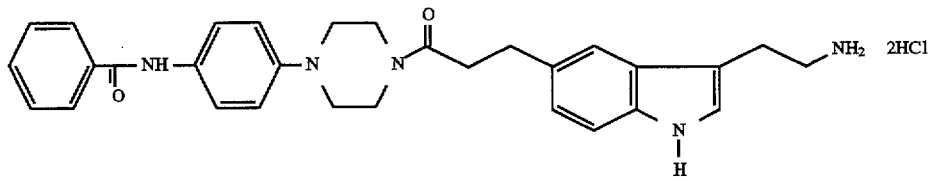

The compound 39 is prepared from the compound 35A (1.08 g, 2.18 mmol) and benzoyl chloride (0.25 ml, 2.18 mmol) according to the method described for the preparation of Example 3.

Purification of the product in the base form is carried out by chromatography on a column of silica gel eluted with a dichloromethane/methanol/aqueous ammonia (85/14/1, v/v) mixture. The pure product is isolated in the form of a colorless syrup which results, after treatment with hydrochloric acid in ether, in the compound 39 in the form of a white powder (869 mg, 68%).

Elemental analysis ($C_{30}H_{35}Cl_2N_5O_2 \cdot H_2O$), % calculated: C 61.43; H 6.36; N 11.94, Cl 12.09; % found: C 61.54, H 6.17, N 11.84, Cl 11.79.

1H NMR, d6-DMSO (ppm): 2.72 t, 2H; 2.93–3.01 m, 6H; 3.21 m, 4H; 3.81 broad s, 4H; 7.00 d, 1H; 7.19–7.55 m, 8H; 7.81 d, 2H; 7.97 d, 2H; 8.14 broad s, 3H; 10.39 s, 1H; 10.90 s, 1H.

Melting point: 209° C.

EXAMPLE 40

4-(4-{2-[3-(2-Aminoethyl)-1H-indol-5-yloxy]-ethyl}piperazin-1-yl)phenylamine hydrochloride

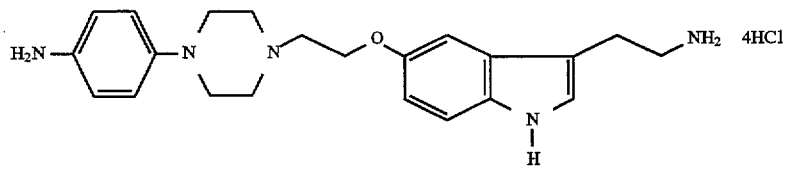

40A: 4-(4-{2-[3-(2-{N-tert-butoxycarbonyl] aminoethyl)-1H-indol-5-yloxy]ethyl}piperazin-1-yl) phenylamine The compound 40A is prepared from the compound 23A (7.1 g, 13.9 mmol) according to the conditions described for the preparation of Example 2 from 1C.

The brown syrup obtained is chromatographed on a column of silica gel eluted with a dichloromethane/acetone (1/1, v/v) mixture. The pure product is isolated in the form of a pink foam (6.45 g, 97%).

1H NMR, d6-DMSO (ppm): 1.38 s, 9H; 2.07 d, 2H; 2.65 m, 4H; 2.75 m, 4H; 2.93 m, 2H; 3.09–3.17 m, 4H; 4.11 t, 2H; 4.56 s, 1H; 6.47–6.58 m, 2H; 6.68–6.75 m, 2H; 6.86–6.90 m, 2H; 7.06–7.08 m, 2H; 7.21 d, 1H; 10.64 s, 1H.

40: 4-(4-{2-[3-(2-Aminoethyl)-1H-indol-5-yloxy] ethyl}-piperazin-1-yl)phenylamine hydrochloride The product 40A (700 mg, 1.46 mmol), in solution in dichloromethane (12 ml), is treated with a solution (~1.5M) of hydrochloric acid in ether (16 ml). After stirring for 1 hour, the mixture is evaporated to dryness and the product formed is desalified. The syrup obtained is chromatographed on a column of silica gel eluted with a dichloromethane/ ethyl acetate (80/18.5/1.5, v/v) mixture. The pure product is isolated in the form of a colorless syrup which results, after treatment with hydrochloric acid in ether, in the compound 40 in the form of a pale pink powder (669 mg, 87%).

Elemental analysis ($C_{22}H_{33}Cl_4N_5O \cdot 2H_2O$), % calculated: C 48.31, H 6.52, N 12.80, Cl 25.93; % found: C 48.31, H 6.65, N 12.55, Cl 24.95.

1H NMR, d6-DMSO (ppm): 3.02 m, 4H; 3.30 m, 4H; 3.65 m, 4H; 3.88 d, 2H; 4.51 broad s, 2H; 6.83 dd, 1H; 7.09–7.33 m, 7H; 8.21 broad s, 3H; 10.35 broad s, 3H; 10.95 s, 1H; 11.59 s, 1H.

Melting point: 200° C. (decomposition).

EXAMPLE 41

N-[4-(4-{2-[3-(2-Aminoethyl)-1H-indol-5-yloxy] ethyl}piperazin-1-yl)phenyl]methanesulfonamide hydrochloride

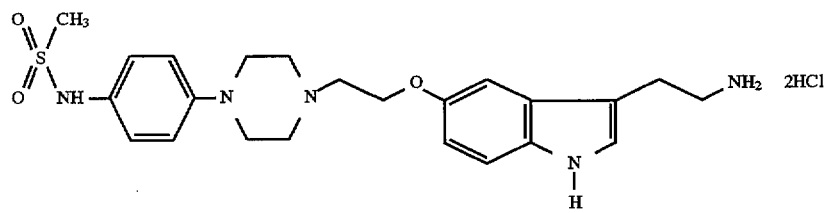

The compound 41 is prepared from product 40A (1 g, 2.08 mmol) and methanesulfonyl chloride (0.194 ml, 2.50 mmol) according to the method described for the preparation of Example 3.

Purification of the product in the base form is carried out by chromatography on a column of silica gel eluted with a dichloromethane/methanol/aqueous ammonia (80/19/1, v/v) mixture. The pure product is isolated in the form of a pale yellow syrup which results, after treatment with hydrochloric acid in ether, in the compound 41 in the form of a white powder (1.01 g, 92%).

Elemental analysis ($C_{23}H_{33}Cl_2N_5O_3s \cdot H_2O$), % calculated: C 50.36, H 6.43, N 12.77, Cl 12.93; % found: C 50.34, H 6.16, N 12.46, Cl 14.31.

1H NMR, d6-DMSO (ppm): 2.86 s, 3H; 3.00 broad s, 4H; 3.15–3.38 m, 4H; 3.60–3.80 m, 6H; 4.48 t, 2H; 6.80 dd, 1H; 6.97 d, 2H; 7.12 d, 2H; 7.20–7.30 m, 3H; 8.17 broad s, 3H; 9.36 s, 1H; 10.91 s, 1H; 11.49 s, 1H Melting point: 230° C. (decomposition).

EXAMPLE 42

N-[4-(4-{2-[3-(2-Aminoethyl)-1H-indol-5-yloxy] acetyl}piperazin-1-yl)phenyl]methylcarbamate hydrochloride

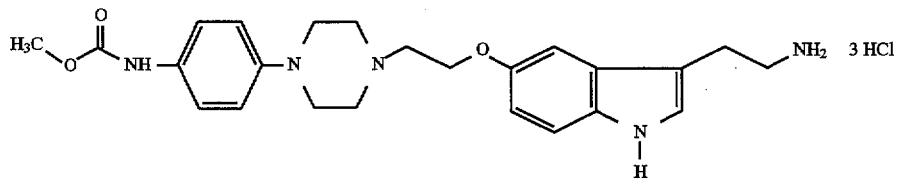

The compound 42 is prepared from the product 40A (1.5 g, 3.13 mmol) and ethyl chloroformate (0.27 ml; 3.44 mmol) according to the method described for the preparation of Example 6.

Purification of the product in the base form is carried out by chromatography on a column of silica gel eluted with a dichloromethane/methanol/aqueous ammonia (80/18.5/1.5, v/v) mixture. The pure product is isolated in the form of a purple syrup which results, after treatment with hydrochloric acid in ether, in the compound 42 in the form of a mauve powder (612 mg, 36%).

Elemental analysis: ($C_{24}H_{34}Cl_3N_5O_3.0.8H_2O$), % calculated: C 51.35, H 6.35, N 12.48, Cl 18.95; % found: C 51.30; H 6.37; N 12.13; Cl 19.02

1HNMR, d6-DMSO (ppm): 3.00–3.30 m, 6H; 3.61 s, 3H; 3.68–3.90 m, 8H; 4.48 t 2H; 6.80 dd, 1H; 6.94 d, 2H; 7.21–7.35 m, 5H; 8.17 broad s, 3H; 9.44 s, 1H; 10.91 s, 1H; 11.41 s, 1H.

Melting point: 166° C. (decomposition).

EXAMPLE 43

2-(5-{2-[4-(2-Methoxy-4-nitrophenyl)piperazin-1-yl)ethoxy}-1-H-indol-3-yl)ethylamine hydrochloride

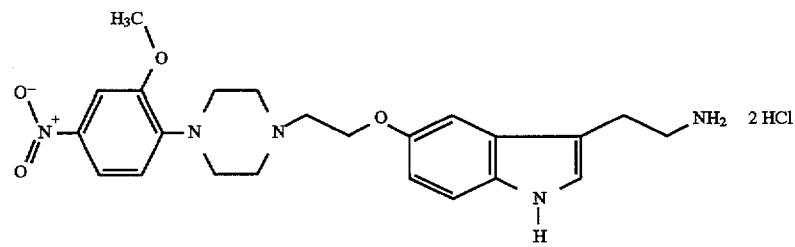

The compound 43 is prepared from the compound 23A (650 mg, 1.92 mmol) and (2-methoxy-4-nitrophenyl)piperazine (545 mg; 2.3 mmol) according to the conditions described for the preparation of Example 23.

Purification of the product in the base form is carried out by chromatography on a column of silica gel eluted with a dichloromethane/methanol/aqueous ammonia (85/14/1, v/v) mixture. The pure product is isolated in the form of a yellow syrup which results, after treatment with hydrochloric acid in ether, in the compound 43 in the form of a yellow powder (777 mg, 79%).

Elemental analysis: ($C_{23}H_{31}Cl_2N_5O_4.1H_2O$), % calculated: C 52.08, H [illegible].27, N 13.20, Cl 13.37; % found: C 52.14; H 6.14; N 13.05; Cl 13.43

1H NMR, d6-DMSO (ppm): 3.03 s, 4H; 3.36 m, 4H; 3.63 m, 4H; 3.83 m, 2H; 3.94 s, 3H; 4.50 t, 2H; 6.84 dd, 1H; 7.13 d, 1H; 7.24–7.32 m, 3H; 7.74 d, 1H; 7.86 dd, 1H; 8.15 broad s, 3H; 10.93 s, 1H; 11.60 s, 1H.

Melting point: 210° C. (decomposition).

EXAMPLE 44

4-(4-{2-[3-(2-Aminoethyl)-1H-indol-5-yloxy]ethyl} piperazin-1-yl)benzonitrile hydrochloride

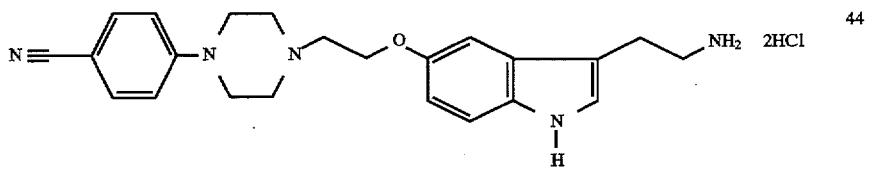

44A: 4-(4-{2-[3-(2-{N-tert-butoxylcarbonyl}aminoethyl)-1H-indol-5-yloxy] ethyl]piperazin-1-yl)benzonitrile The compound 44A is prepared from the product 23A (2.8 g, 8.19 mmol) and (4-cyanophenyl)piperazine (3.06 g, 8.19 mmol) according to the method described for the preparation of Example 23.

The syrup obtained is chromatographed on a column of silica gel eluted with a dichloromethane/ethyl acetate (5/1, v/v) mixture. The pure product is isolated in the form of a colorless syrup (2.03 g, 50%).

1H NMR, CDCl₃ (ppm): 1.42 s, 9H; 2.74–2.94 m, 8H; 3.36 m, 6H; 4.20 t, 2H; 4.62 broad s, 1H; 6.83 m, 3H; 7.04 dd, 2H; 7.24 m, 1H; 7.50 m, 2H; 8.11 s, 1H.

44: 4-(4-{2-[3-(2-Aminoethyl)-1H-indol-5-yloxy]ethyl]-piperazin-1yl)benzonitrile hydrochloride The product 44A (707 mg, 1.44 mmol) is then deprotected according to the method described for the preparation of Example 2 from 2A.

Purification of the product in the base form is carried out by chromatography on a column of silica gel eluted with a dichloromethane/methanol/aqueous ammonia (80/19/1, v/v) mixture. The pure product is isolated in the form of a colorless syrup which results, after treatment with hydrochloric acid in ether, in the compound 44 in the form of a white powder (496 mg; 76%).

Elemental analysis ($C_{23}H_{27}N_5O_1 \cdot 2.3HCl \cdot H_2O$), % calculated: C 56.22, H 6.42, N 14.25, Cl 16.59; % found: C 56.84, H 6.40, N 14.04, Cl 16.72.

1H NMR, d6-DMSO (ppm): 3.02 s, 4H; 3.37 m, 4H; 3.62 m, 4H; 4.11 m, 2H; 4.49 t, 2H; 6.84 dd, 1H; 7.13 d, 2H; 7.23–7.32 m, 3H; 7.67 d, 2H; 8.14 broad s, 3H; 10.93 s, 1H; 11.58 broad s, 1H.

Melting point: 160° C.

EXAMPLE 45

[2-(5-{2-[4-(4-(Aminomethyl)phenyl)piperazin-1-yl]ethoxy}-1H-indol-3-yl)ethyl]methylamine hydrochloride

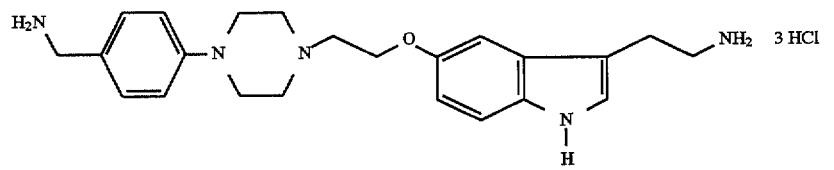

The compound 44A (600 mg, 1.23 mmol), in solution in anhydrous tetrahydrofuran (10 ml), is treated under nitrogen and at 0° C. with a molar solution of lithium aluminum hydride in tetrahydrofuran (2.5 ml, 2.46 mmol). The mixture is then stirred at 80° C. for 12 h. The mixture is then treated with sodium sulfate/water and then filtered through celite.

Purification of the product in the base form is carried out by chromatography on a column of silica gel eluted with a dichloromethane/methanol/aqueous ammonia (80/18/2, v/v) mixture. The pure product is isolated in the form of a pale yellow syrup which results, after treatment with hydrochloric acid in ether, in the compound 45 in the form of a yellow powder (281 mg, 44%).

Elemental analysis: ($C_{24}H_{36}Cl_3N_5O_1 \cdot 1.3H_2O$), % calculated: C 53.35, H 7.20, N 12.96, Cl 19.68; % found: C 53.37, H 7.19, N 12.70; Cl 19.66.

1H NMR, d6-DMSO (ppm): 3.09–3.28 m, 8H; 3.49–3.93 m, 8H; 4.53 s, 2H; 6.84 dd, 1H; 7.05 d, 2H; 7.23–7.42 m, 5H; 8.39 broad s, 3H; 9.16 broad s, 2H; 10.94 s, 1H; 11.55 broad s, 1H.

Melting point: 84° C. (decomposition).

EXAMPLE 46

2-(4-{2-[3-(2-Aminoethyl)-1H-indol-5-yloxy]acetyl}piperazin-1-yl)benzonitrile hydrochloride

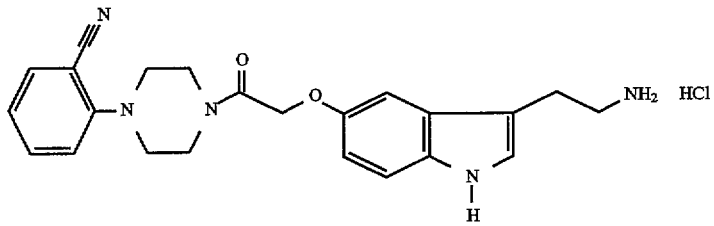

46A: 2-(4-{2-[3-(2-{N-tert-Butoxycarbonyl}aminoethyl)-1H-indol-5-yloxy]acetyl}piperazin-1-yl)benzonitrile The compound 46A is prepared from (2-cyanophenyl)piperazine (1 g; 5.34 mmol), chloroacetyl chloride (0.43 ml, 5.34 mmol) and the compound 1A (660 mg, 2.39 mmol) according to the procedure described for the preparation of the compound 1B.

The syrup obtained is chromatographed on a column of silica gel eluted with a dichloromethane/acetone (5/1, v/v) mixture. The pure product is isolated in the form of a colorless syrup (1.01 g, 84%).

1H NMR CDCl$_3$(ppm): 1.40 s, 9H; 2.88 t, 2H; 3.16 m, 4H; 3.41 t, 2H; 3.84 t, 2H; 4.60 broad s, 1H; 4.75 s, 2H; 6.86 dd, 1H; 6.94–7.09 m, 4H; 7.23 m, 1H; 7.43–7.58 m, H; 8.10 broad s, 1H.

46: 2-(4-{2-[3-(2-Aminoethyl)-1H-indol-5-yloxy]acetyl}piperazin-1-yl)benzonitrile hydrochloride The product 46A (741 mg, 1.47 mmol) is then deprotected according to the method described in the preparation of Example 2 from 2A.

Purification of the product in the base form is carried out by chromatography on a column of silica gel eluted with a dichloromethane/methanol/aqueous ammonia (80/19/1, v/v) mixture. The pure product is isolated in the form of a colorless syrup which results, after treatment with hydrochloric acid in ether, in the compound 46 in the form of a white powder (388 mg; 60%).

Elemental analysis ($C_{23}H_{26}ClN_5O_2 \cdot 1.4H_2O$), % calculated: C 59.39, H 6.24; N 15.06; Cl 7.62; % found: C 59.72, H 5.85, N 14.79, Cl 8.14.

1HNMR, d6-DMSO (ppm): 3.00–3.20 m, 8H; 3.69 m, 4H; 4.83 s, 2H; 6.79 dd, 1H; 7.10–7.29 m, 5H; 7.58–7.76 m, 2H; 8.08 broad s, 3H; 10.88 s, 1H.

Melting point: 107° C. (decomposition).

EXAMPLE 47

2-[3-(2-Aminoethyl)-1H-indol-5-yloxy]-1-[4-(2-aminomethylphenyl)piperazin-1-yl)ethanone hydrochloride

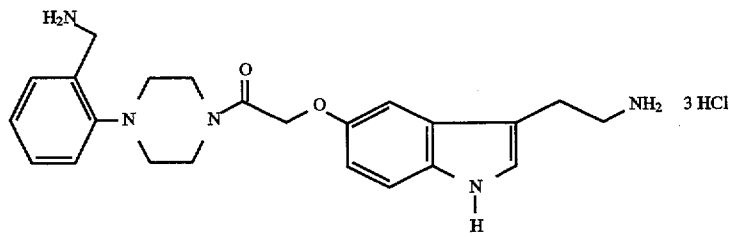

47A: 2-[3-(2-{N-tert-Butoxycarbonyl}aminoethyl)-1H-indol-5-yloxy]-1-[4-(2-(aminomethyl)phenyl) piperazin1-yl)ethanone The compound 46A (3.4 g; 6.8 mmol), in solution in tetrahydrofuran (114 ml) in the presence of Raney Nickel (~200 mg, catalytic), is subjected to an atmospheric pressure of hydrogen for 48 hours at room temperature. The mixture is filtered through celite and evaporated to dryness.

The syrup obtained is chromatographed on a column of silica gel eluted with a dichloromethane/methanol/aqueous ammonia (90/9/1, v/v) mixture. The pure product is isolated in the form of a colorless syrup (2.97 g; 86%).

1H NMR, d6-DMSO (ppm): 1.36 s, 9H; 2.70–2.88 m, 6H; 3.17 m, 4H; 3.62 broad s, 4H; 3.77 s, 2H; 4.77 s, 2H; 6.75 dd, 1H; 6.87 t, 1H; 7.00–7.24 m, 6H; 7.43 dd, 1H; 10.65 s, 1H.

47: 2-[3-(2-Aminoethyl)-1H-indol-5-yloxy]-1-[4-(2-(aminomethyl)phenyl)piperazinlyl]ethanone hydrochloride The compound 47A (600 mg; 1.18 mmol) is then deprotected according to the method described for the preparation of Example 40.

Purification of the product in the base form is carried out by chromatography on a column of silica gel eluted with a dichloromethane/methanol/aqueous ammonia (80/18/2, v/v) mixture. The pure product is isolated in the form of a colorless syrup which results, after treatment with hydrochloric acid in ether, in the compound 47 in the form of a white powder (506 mg, 83%).

Elemental analysis: ($C_{23}H_{32}Cl_3N_5O_2 \cdot 1.6H_2O$), % calculated: C 50.62, H 6.50, N 12.83, Cl 19.49; % found: C 50.85, H 6.36, N 12.64, Cl 18.00.

1HNMR, d6-DMSO (ppm): 2.80–2.99 m, 8H; 3.69 broad s, 4H; 4.11 s, 6H; 4.82 s, 2H; 6.77 dd, 1H; 7.15–7.54 m, 7H; 8.16 broad s, 3H; 8.45 broad s, 3H; 10.86 s, 1H.

Melting point: 198° C. (decomposition).

EXAMPLE 48

N-[2-[4-{2-[3-(2-Aminoethyl)-1H-indol-5-yloxy] acetyl}piperazin-1-yl)benzylmethanesulfonamide hydrochloride

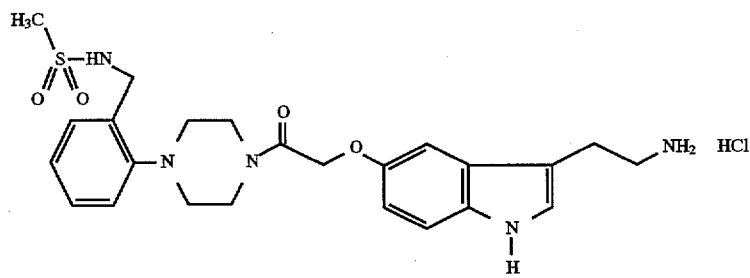

The compound 48 is prepared from the compound 47A (800 mg; 1.58 mmol) and mesyl chloride (0.27 ml; 3.16 mmol) according to the method described for the preparation of Example 3.

Purification of the product in the base form is carried out by chromatography on a column of silica gel eluted with a dichloromethane/methanol/aqueous ammonia (83/16/1, v/v) mixture. The pure product is isolated in the form of a colorless syrup which results, after treatment with hydrochloric acid in ether, in the compound 48 in the form of a white powder (585 mg, 71%).

Elemental analysis: ($C_{24}H_{31}N_5O_4S \cdot 1.5HCl \cdot 1H_2O$), % calculated: C 51.63, H 6.23, N 12.54, Cl 9.52; % found: C 51.98, H 6.11, N 12.45, Cl 8.94.

1H NMR, d6-DMSO (ppm): 2.80–3.00 m, 11H; 3.67 broad s, 4H; 4.26 d, 2H; 4.82 s, 2H; 6.79 dd, 1H; 7.09–7.47 m, 7H; 8.01 broad s, 3H; 10.85 s, 1H.

Melting point: 250° C.

EXAMPLE 49

N-[2-(4-{2-[3-(2-Aminoethyl)-1H-indol-5-yloxy]
acetyl}piperazin-1-yl]benzenesulfonamide
hydrochloride

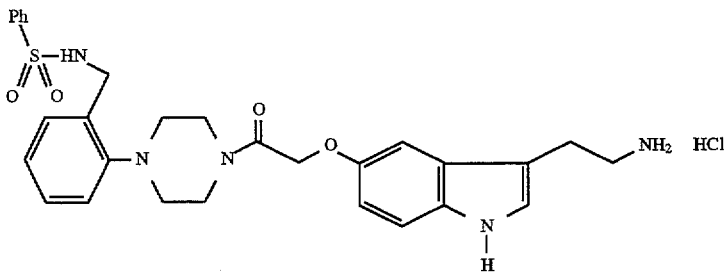

49

The compound 49 is prepared from the compound 47A (800 mg; 1.58 mmol) and benzenesulfonyl chloride (0.22 ml; 1.70 mmol) according to the method described for the preparation of Example 3.

Purification of the product in the base form is carried out by chromatography on a column of silica gel eluted with a dichloromethane/methanol/aqueous ammonia (80/19.5/0.5, v/v) mixture. The pure product is isolated in the form of a colorless syrup which results, after treatment with hydrochloric acid in ether, in the compound 49 in the form of a white powder (674 mg, 73%).

Elemental analysis: ($C_{29}H_{34}ClN_5O_4S$), % calculated: C 59.63, H 5.87, N 11.99, Cl 6.07; % found: C 59.34, H 5.85, N 11.81, Cl 6.21.

1H NMR, d6-DMSO (ppm): 2.75 m, 4H; 3.00 m, 4H; 3.50 broad s, 4H; 4.04 s, 2H; 4.78 s, 2H; 6.77 dd, 1H; 7.01–7.33 m, 7H; 7.55 m, 3H; 7.80 m, 2H; 7.99 broad s, 4H; 10.84 s, 1H.

Melting point: 240° C.

EXAMPLE 50

4-(4-{2-[3-(2-Aminoethyl)-1H-indol-5-yloxy]-
acetyl}piperazin-1-yl)benzonitrile hydrochloride

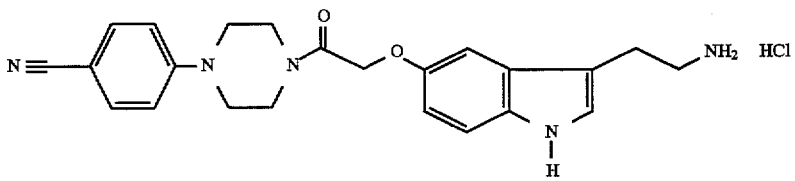

50A—4-(4-{2-[3-(2-{N-tert-
Butoxycarbonyl}aminoethyl)-1H-indol-5-yloxy]
acetyl}piperazin-1-yl)benzonitrile The compound 50A is prepared from (4-cyanophenyl) piperazine (30.1 g, 160.9 mmol), chloroacetyl chloride (12.8 ml, 160.9 mmol) and the compound 1A (7.2 g, 26.06 mmol) according to the procedure described for the preparation of the compound 1B.

The syrup obtained is chromatographed on a column of silica gel eluted with an ethyl acetate/dichloromethane (2/1, v/v) mixture. The pure product is isolated in the form of a white powder (10.9 g, 83%).

Elemental analysis ($C_{28}H_{33}N_5O_4$), % calculated: C 66.78, H 6.61, N 13.91, % found: C 66.92, H 6.73, N 13.64.

1H NMR, CDCl3 (ppm): 1.36 s, 9H; 2.83 t, 2H; 3.25–3.40 m, 6H; 3.75 m, 4H; 4.71 s, 2H; 6.83 m, 3H; 6.97 s, 1H; 7.03 d, 1H; 7.22 d, 1H; 7.45 m, 2H; 8.75 broad s, 1H.

50—4-(4-{2-[3-(2-Aminoethyl)-1H-indol-5-yloxy]
acetyl}-piperazin-1-yl)benzonitrile hydrochloride The product 50A (1 g, 1.98 mmol) is then deprotected according to the method described for the preparation of Example 1 from 2A.

Purification of the product in the base form is carried out by chromatography on a column of silica gel eluted with a dichloromethane/methanol/aqueous ammonia (80/19/1, v/v) mixture. The pure product is isolated in the form of a colorless syrup which results, after treatment with hydrochloric acid in ether, in the compound 50 in the form of a white powder (728 mg, 88%).

Elemental analysis ($C_{23}H_{25}N_5O_2 \cdot 1.3HCl \cdot 0.8H_2O$), % calculated: C 59.37, H 6.04, N 15.05, Cl 9.91; % found: C 59.46, H 5.92, N 14.87, Cl 9.77.

1H NMR, d6-DMSO (ppm): 2.99 m, 4H; 3.45 m, 4H; 3.68 m, 4H; 4.83 s, 2H; 6.78 dd, 1H; 7.03 d, 2H; 7.19 dd, 2H; 7.26 d, 1H; 7.61 d, 2H; 8.03 broad s, 3H; 10.86 s, 1H.

Melting point: 224°–226° C.

EXAMPLE 51

2-[3-(2-Aminoethyl)-1H-indol-5-yloxy]-1-[4-(4-
(aminomethyl)phenyl)piperazin-1-yl]ethanone
hydrochloride

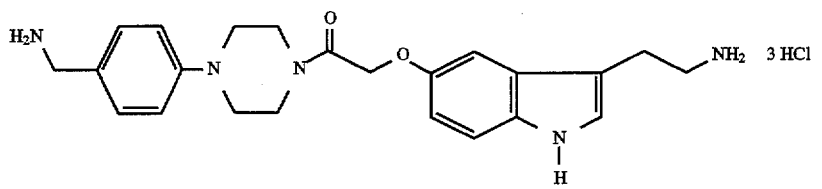

51

51A: 2-[3-(2-{N-tert-Butoxycarbonyl}aminoethyl)-1H-indol-5-yloxy]-1-[4-(4-(aminomethyl)phenyl)piperazin-1-yl]-ethanone The compound 50A (800 mg, 1.59 mmol) is hydrogenated under the conditions described for the preparation of the product 47A from 46A.

The syrup obtained is chromatographed on a column of silica gel eluted with a dichloromethane/methanol/aqueous ammonia (80/19/1, v/v) mixture. The pure product is isolated in the form of a colorless syrup (800 mg, 99%).

1H NMR, CDCl$_3$ (ppm): 1.44 s, 9H; 2.91 t, 2H; 3.17 m, 4H; 3.46 m, 2H; 3.80 m, 6H; 4.66 broad s, 1H; 4.78 s, 2H; 6.90 m, 3H; 7.02 d, 1H; 7.11 d, 1H; 7.21–7.29 m, 4H; 8.14 broad s, 1H.

51: 2-[3-(2-Aminoethyl)-1H-indol-5-yloxy]-1-[4-(4-(aminomethyl)phenyl)piperazin-1-yl]ethanone hydrochloride The compound 51A (500 mg, 0.98 mmol) is then deprotected under the conditions described for the preparation of Example 2 from 2A.

Purification of the product in the base form is carried out by chromatography on a column of silica gel eluted with a dichloromethane/methanol/aqueous ammonia (75/20/5, v/v) mixture. The pure product is isolated in the form of a beige solid which results, after treatment with hydrochloric acid in ether in the compound 51 in the form of a pale yellow powder (304 mg, 60%).

Elemental analysis ($C_{23}H_{32}Cl_3N_5O_2.1.5H_2O$), % calculated: C 50.79, H 6.49, N 12.88, Cl 19.55; % found: C 50.68, H 6.46, N 12.71, Cl 20.09.

1HNMR, d6-DMSO (ppm): 2.98 broad s, 4H; 3.20–3.37 m, 4H; 3.69 m, 4H; 3.90 m, 2H; 4.82 s, 2H; 6.77 dd, 1H; 7.10 d, 2H; 7.18 d, 2H; 7.25 d, 1H; 7.38 d, 2H; 8.13 broad s, 3H; 8.35 broad s, 3H; 10.85 s, 1H.

Melting point: 185° C. (decomposition).

EXAMPLE 52

N-[4-(4-(2-[3-(2-Aminoethyl)-1H-indol-5-yloxy]acetyl}piperazin-1-yl)benzyl]methanesulfonamide hydrochloride The compound 52 is prepared from the product 51A (900 mg, 1.77 mmol) and mesyl chloride (0.14 ml, 1.77 mmol) under the conditions described for the preparation of Example 3.

Purification of the product in the base form is carried out by chromatography on a column of silica gel eluted with a dichloromethane/methanol/aqueous ammonia (80/19/1, v/v) mixture. The pure product is isolated in the form of a beige solid which results, after treatment with hydrochloric acid in ether, in the compound 52 in the form of a white powder (277 mg, 28%).

Elemental analysis ($C_{24}H_{33}Cl_2N_5O_4S.0.3H_2O$), % calculated: C 51.12, H 6.01, N 12.42, Cl 12.57; % found: C 51.12, H 6.15, N 12.26, Cl 11.78.

1HNMR, d6-DMSO (ppm): 2.80 s, 3H; 2.97 broad s, 4H; 3.25 m, 4H; 3.74 m, 4H; 4.05 s, 2H; 4.81 s, 2H; 6.75 dd, 1H; 7.17–7.29 m, 7H; 7.49 broad s, 1H; 8.05 broad s, 3H; 10.83 s, 1H.

Melting point: 154° C. (decomposition).

EXAMPLE 53

2-[3-(2-Aminoethyl)-1H-indol-5-yloxy]-1-[4-(4-amino-2-methoxyphenyl)piperazin-1-yl]ethanone hydrochloride

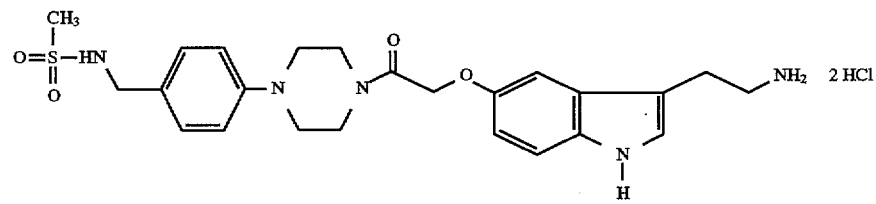

52

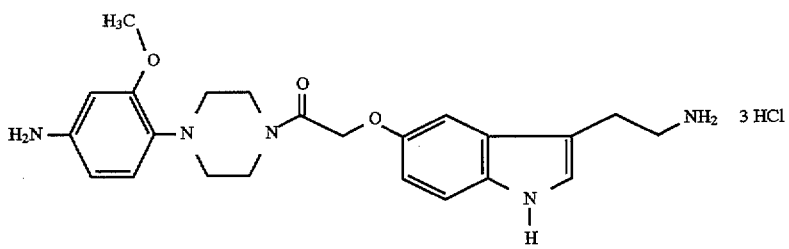

53A: 2-[3-(2-{N-tert-Butoxycarbonyl}aminoethyl)-1H-indol-5-yloxy]-1-[4-(4-amino-2-methoxyphenyl)piperazin-1-yl]ethanone The compound 22 in its protected form (NHBOC) (3.06 g, 5.53 mmol) is treated under the conditions described for the preparation of Example 2 from 1C.

The syrup obtained is chromatographed on a column of silica gel eluted with a dichloromethane/acetone (2/1, v/v) mixture. The pure product is isolated in the form of a beige foam (2.3 g, 81%).

1H NMR, d6-DMSO (ppm): 1.38 s, 9H; 2.72 m, 6H; 3.18 m, 2H; 3.60–3.75 m, 7H; 4.77 s, 2H; 6.05–6.31 m, 2H; 6.75–6.89 m, 2H; 7.07 dd, 2H; 7.23 d, 1H; 10.67 s, 1H.

53: 2-[3-(2-Aminoethyl)-1H-indol-5-yloxy]-1-[4-(4-amino-2-methoxyphenyl)piperazin-1-yl]ethanone hydrochloride The compound 53A (600 mg, 1.14 mmol) is then deprotected according to the method described for the preparation of Example 40 from 40A.

Purification of the product in the base form is carried out by chromatography on a column of silica gel eluted with a dichloromethane/methanol/aqueous ammonia (80/18/2, v/v) mixture. The pure product is isolated in the form of a colorless syrup which results, after treatment with hydrochloric acid in ether, in the compound 53 in the form of a white powder (441 mg, 73%).

Elemental analysis ($C_{23}H_{32}Cl_3N_5O_3.2H_2O$), % calculated: C 48.25, H 6.41, N 12.23, Cl 18.58; % found: C 48.03, H 6.19, N 12.06, Cl 18.72.

1H NMR, d6-DMSO (ppm): 3.00–3.16 m, 8H; 3.71 m, 4H; 3.81 s, 3H; 4.83 s, 2H; 6.77–6.96 m, 3H; 7.10–7.29 m, 4H; 8.14 broad s, 3H; 10.87 s, 1H.

Melting point: ~190° C.

EXAMPLE 54

N-[4-(4-{2-[3-(2-Aminoethyl)-1H-indol-5-yloxy]acetyl}piperazin-1-yl)-3-methoxyphenyl]methanesulfonamide hydrochloride The compound 54 is prepared from the product 53A (1.0 g, 1.91 mmol) and mesyl chloride (0.16 ml, 2.10 mmol) according to the method described for the preparation of Example 3.

Purification of the product in the base form is carried out by chromatography on a column of silica gel eluted with a dichloromethane/methanol/aqueous ammonia (80/18/2, v/v) mixture. The pure product is isolated in the form of a beige solid which results, after treatment with hydrochloric acid in ether, in the compound 54 in the form of a beige powder (745 mg; 68%).

Elemental analysis ($C_{24}H_{33}Cl_2N_5O_5S.2H_2O$). % calculated: C 47.21, H 6.11, N 11.47, Cl 11.61; % found: C 47.49; H 5.82; N 11.29, Cl 11.76.

1HNMR, d6-DMSO (ppm): 2.97–3.16 m, 11H; 3.79 m, 7H; 4.82 s, 2H; 6.80 dd, 1H; 6.85 d, 2H; 7.10–7.28 m, 4H; 8.04 broad s, 3H; 9.68 s, 1H; 10.85 s, 1H.

Melting point: 195° C. (decomposition).

EXAMPLE 55

2-[3-(2-Aminoethyl)-1H-indol-5-yloxy]-1-[4-(4-nitronaphth-1-yl)piperazin-1-yl]ethanone hydrochloride

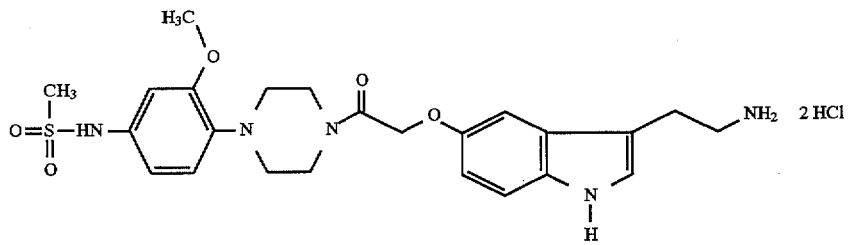

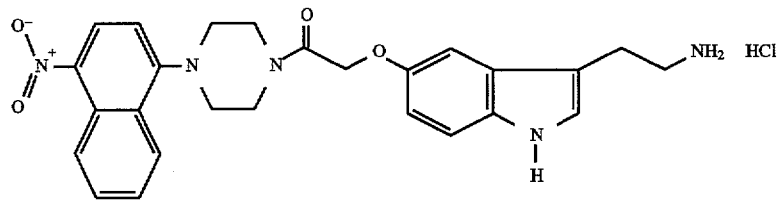
55

The compound 55 is prepared from (4-nitronaphthyl) piperazine (2.47 g, 9.56 mmol), chloroacetyl chloride (1.37 ml, 17.2 mmol) and the compound 1A (350 mg, 1.26 mmol) according to the method described for the preparation of Example 1.

Purification of the product in the base form is carried out by chromatography on a column of silica gel eluted with a dichloromethane/methanol/aqueous ammonia (85/14/1, v/v) mixture. The pure product is isolated in the form of yellow crystals which results, after treatment with hydrochloric acid in ether, in the compound 55 in the form of an orange powder (340 mg, 49%).

Elemental analysis ($C_{26}H_{28}ClN_5O_4.2H_2O$), % calculated: C 57.19, H 5.91, N 12.83, Cl 6.49; % found: C 57.59, H 5.52, N 12.69, Cl 7.02.

1H NMR, d6-DMSO (ppm): 2.97 m, 4H; 3.13–3.21 m, 4H; 3.82 m, 4H; 4.84 s, 2H; 6.78 dd, 1H; 7.17–7.27 m, 4H; [illegible]65-7.82 m, 2H; 8.01 large s, 3H; 8.26–8.35 m, 2H; 8.51 d, 1H; 10.84 s, 1[illegible].

Melting point: 183° C.

EXAMPLE 56

4-(4-{2-[3-(2-Aminoethyl)-1H-indol-5-yloxy]-acetyl}piperazin-1-yl)phenyl methanesulfonate hydrochloride

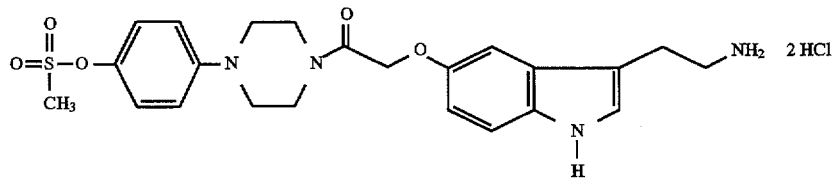
56

The compound 56 is prepared from 4-(piperazin-1-yl) phenyl methanesulfonate (1.62 g, 6.3 mmol), chloroacetyl chloride (0.60 ml, 7.54 mmol) and the compound 1A (1.16 g, 4.2 mmol) according to the method described for the preparation of Example 1.

Purification of the product in the base form is carried out by chromatography on a column of silica gel eluted with a dichloromethane/methanol/aqueous ammonia (85/14/1, v/v) mixture. The pure product is isolated in the form of a colorless syrup which results, after treatment with hydrochloric acid in ether, in the compound 56 in the form of a beige powder (504 mg, 22%).

Elemental analysis ($C_{23}H_{30}Cl_2N_4O_5S.1H_2O$), % calculated: C 49.18, H 5.71, N 9.97, Cl 12.62; % found: C 49.13, H 5.67, N 9.82, Cl 11.39.

1H NMR, d6-DMSO (ppm): 2.97 m, 4H; 3.22 s, 4H; 3.29 s, 3H; 3.65 m, 4H; 4.80 s, 2H; 6.77 dd, 1H; 7.02–7.26 m, 7H; 8.00 broad s, 3H; 10.84 s, 1H.

Melting point: 238°–240° C. (decomposition).

EXAMPLE 57

6-[3-(2-Aminoethyl)-1H-indol-5-yloxy]-1-[4-(4-nitrophenyl)piperazin-1-yl]hexan-1-one hydrochloride

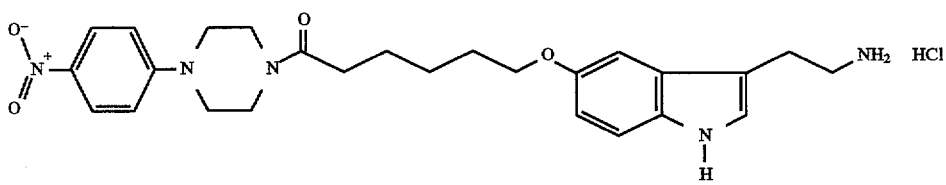
57

57A: 6-Chloro-1-[4-(4-nitrophenyl)piperazin-1-yl]hexan-1-one (4-Nitrophenyl)piperazine (3.0 g, 14.48 mmol) in solution in methyl ethyl ketone (105 ml) in the presence of potassium carbonate (6 g, 43.4 mmol), is treated under nitrogen and at 0° C. with 6-chlorohexanoic chloride (10.2 g, 15mmol). After stirring for 2 hours from 0° C. to room temperature, the mixture is diluted with ethyl acetate and washed with sodium hydroxide solution (2N) and then with water. The organic phase is dried over sodium sulfate, filtered and evaporated to dryness.

The syrup obtained is chromatographed on a column of silica gel eluted with a dichloromethane/acetone (30/1 then 10/1, v/v) mixture. The product 57A is obtained in the form of yellow crystals (4.1 g, 84%).

57B: 6-[3-(2-{N-tert-Butoxycarbonyl}aminoethyl)-1H-indol-5-yloxy]-1-[4-(4-nitrophenyl)piperazin-1-yl]hexan-1-one A mixture of the compound 1A (1.87 g, 6.77 mmol) and the compound 57A (4.1 g, 12.2 mmol) in dimethylformamide (11 ml) in the presence of cesium carbonate (3.3 g, 10.1 mmol) is heated at 70° C. for 24 h. The mixture is diluted with ethyl acetate and washed with water. The organic phase is dried over sodium sulfate, filtered and evaporated to dryness.

The syrup obtained is chromatographed on a column of silica gel eluted with a dichloromethane/ethyl acetate (2/1 then 1/1, v/v) mixture. The pure product is isolated in the form of a yellow syrup (2.5 g, 63%).

1H NMR, d6-DMSO (ppm): 1.34 s, 9H; 1.44–1.72 m, 6H; 2.36 t, 2H; 2.70 t, 2H; 3.12 m, 2H; 3.46 m, 4H; 3.56 m, 4H; 3.92 t, 2H; 6.66 dd, 1H; 6.84 t, 1H; 6.96 m, 3H; 7.04 d, 1H; 7.17 d, 1H; 8.04 d, 2H; 10.58 s, 1H.

57: 6-[3-(2-Aminoethyl)-1H-indol-B-yloxy]-1-[4-(4-nitrophenyl)piperazin-1-yl]hexan-1-one hydrochloride The compound 57B (500 mg; 0.86 mmol) is then deprotected according to the method described for the preparation of Example 1 from 1C.

Purification of the product in the base form is carried out by chromatography on a column of silica gel eluted with a dichloromethane/methanol/aqueous ammonia (85/14/1, v/v) mixture. The pure product is isolated in the form of a yellow syrup which results, after treatment with hydrochloric acid in ether, in the compound 57 in the form of a yellow powder (315 mg, 71%).

Elemental analysis ($C_{26}H_{34}ClN_5O_4 \cdot 1H_2O$), % calculated: C 58.08, H 6.77, N 13.02, Cl 7.25; % found: C 57.96, H 6.47, N 12.73, Cl 7.48.

1H NMR, d6-DMSO (ppm): 1.44–1.76 m, 6H; 2.37 t, 2H; 2.96 m, 4H; 3.54 m, 8H; 3.94 t, 2H; 6.70 dd, 1H; 6.95–7.04 m, 3H; 7.15–7.23 m, 2H; 8.02 m, 5H; 10.77 s, 1H.

Melting point: 100° C.

EXAMPLE 58

6-[3-(2-Aminoethyl)-1H-indol-5-yloxy]-1-[4-(4-aminophenyl)piperazin-1-yl]hexan-1-one hydrochloride 58A: 6-(3-(2-{N-tert-Butoxycarbonyl}aminoethyl)-1H-indol -5-yloxy]-1-[4-(4-aminophenyl)piperazin-1-yl]hexan-1-one The compound 57B (2.01 g, 3.46 mmol) is hydrogenated under the conditions described for the preparation of Example 2A.

The syrup obtained is chromatographed on a column of silica gel eluted with a dichloromethane/acetone (3/1, v/v) mixture. The pure product is isolated in the form of a beige syrup (1.89 g, 99%).

1H NMR, d6-DMSO (ppm): 1.35 s, 9H; 1.40–1.72 m, 6H; 2.34 t, 2H; 2.68–2.86 m, 6H; 3.12 m, 2H; 3.52 broad s, 4H; 3.92 t, 2H; 4.59 s, 2H; 6.46 d, 2H; 6.67 m, 3H; 6.84 t, 1H; 7.00 dd, 2H; 7.17 d, 1H.

58: 6-[3-(2-Aminoethyl)-1H-indol-5-yloxy]-1-[4-(4-aminophenyl)piperazin-1-yl]hexan-1-one hydrochloride The compound 58A (500 mg, 0.91 mmol) is then deprotected under the conditions described for the preparation of Example 1 from 1C.

Purification of the product in the base form is carried out by chromatography on a column of silica gel eluted with a dichloromethane/methanol/aqueous ammonia (80/18/2, v/v) mixture. The pure product is isolated in the form of a pale yellow syrup which results, after treatment with hydrochloric acid in ether, in the compound 58 in the form of a pale pink powder (270 mg, 60%).

Elemental analysis ($C_{26}H_{38}Cl_3N_5O_2 \cdot 1.4H_2O$), % calculated: C 53.46, H 7.04; N 11.99, Cl 18.21; % found: C 53.44, H 6.96, N 11.80, Cl 17.13.

1H NMR, d6-DMSO (ppm): 1.40–1.80 m, 6H; 2.40 t, 2H; 2.99 broad s, 4H; 3.18 broad s, 4H; 3.64 m, 4H; 3.97 t, 2H; 6.70 dd, 1H; 7.07–7.28 m, 7H; 8.09 broad s, 3H; 10.82 s, 1H.

Melting point: 150° C.

EXAMPLE 59

N-[4-(4-{6-[3-(2-Aminoethyl)-1H-indol-5-yloxy] hexanoyl}piperazin-1-yl)phenyl]methane sulfonamide hydrochloride

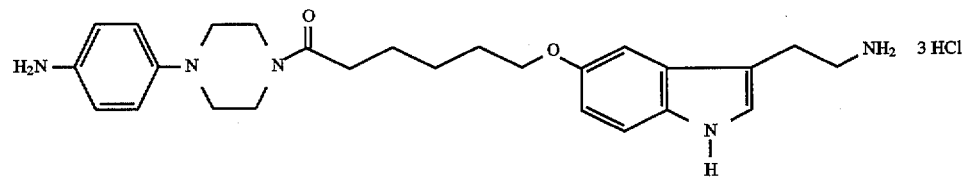

58

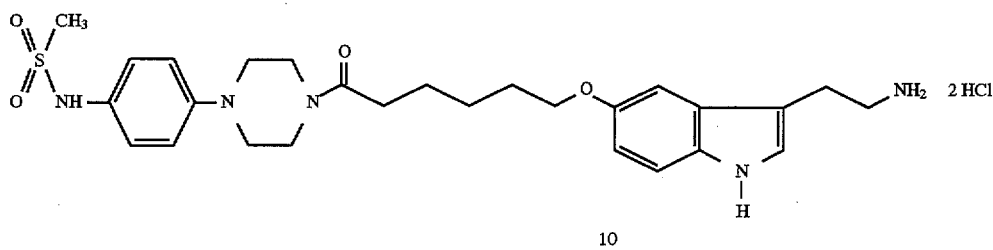

The compound 59 is prepared from the product 58A (690 mg, 1.25 mmol) and mesyl chloride (107 µl, 1.37 mmol) under the conditions described for the preparation of Example 3.

Purification of the product in the base form is carried out by chromatography on a column of silica gel eluted with a dichloromethane/methanol/aqueous ammonia (80/19/1, v/v) mixture. The pure product is isolated in the form of a pale yellow syrup which results, after treatment with hydrochloric acid in ether, in the compound 59 in the form of a beige powder (658 mg, 92%).

Elemental analysis ($C_{27}H_{39}Cl_2N_5O_4S.0.5H_2O.0.3EtOH$), % calculated: C 53.20, H 6.61, N 11.49, Cl 11.63; % found: C 53.24, H 6.96, N 11.10, Cl 10.12.

1H NMR, d6-DMSO (ppm): 1.53–1.75 m, 6H; 2.41 t, 2H; 2.93 s, 3H; 2.99 broad s, 4H; 3.23 broad s, 4H; 3.72 broad s, 4H; 3.97 t, 2H; 6.75 d, 1H; 7.07–7.25 m, 7H; 8.04 broad s, 3H; 9.62 s, 1H; 10.81 s, 1H.

Melting point: 141° C.

EXAMPLE 60

N-[4-(4-{6-[3-(2-Aminoethyl)-1H-indol-5-yloxy]hexanol}piperazin-1-yl)benzyl]benzenesulfonamide hydrochloride

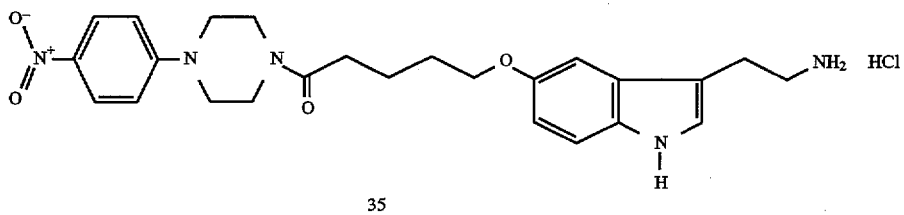

The compound 60 is prepared from the product 58A (690 mg, 1.25 mmol) and benzenesulfonyl chloride (176 µl, 1.37 mmol) under the conditions described for the preparation of Example 3.

Purification of the product in the base form is carried out by chromatography on a column of silica gel eluted with a dichloromethane/methanol/aqueous ammonia (80/19/1, v/v) mixture. The pure product is isolated in the form of a beige syrup which results, after treatment with hydrochloric acid in ether, in the compound 60 in the form of a beige powder (550 mg, 67%).

Elemental analysis ($C_{32}H_{41}Cl_2N_5O_4S.0.5H_2O$) % calculated: C 57.22, H 6.30, N 10.43, Cl 10.56; % found: C 57.31, H 6.20, N 10.18, Cl 9.41.

1HNMR, d6-DMSO (ppm): 1.52–1.75 m, 6H; 2.34 t, 2H; 2.99–3.08 m, 8H; 3.61 broad s, 4H; 3.96 t, 2H; 6.73 dd, 1H; 6.97–7.26 m, 7H; 7.53–7.74 m, 5H; 8.05 broad s, 3H; 10.05 s, 1H; 10.82 s, 1H.

Melting point: 132° C.

EXAMPLE 61

5-[3-(2-Aminoethyl)-1H-indol-5-yloxy]-1-[4-(4-nitrophenyl)piperazin-1-yl]pentan-1-one hydrochloride

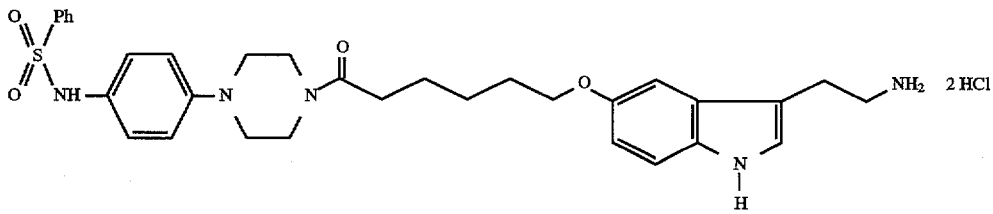

61A: 5-[3-(2-{N-tert-Butoxycarbonyl}aminoethyl)-1H-indol-5-yloxy]-1-[4-(4-nitrophenyl)piperazin-1-yl]pentan-1-one The compound 61A is prepared from (4-nitrophenyl)piperazine (1.1 g, 5.20 mmol), 5-chloropentanoyl chloride (2.6 ml, 20.8 mmol) and the compound 1A (800 mg, 2.89 mmol) under the conditions described for the preparation of the compound 57B.

The syrup obtained is chromatographed on a column of silica gel eluted with a dichloromethane/acetone (10/1, v/v) mixture. The pure product is isolated in the form of a yellow syrup (685 mg, 42%).

1H NMR, d6-DMSO (ppm): 1.35 s, 9H; 1.71 m, 4H; 2.46 t, 2H; 2.70 t, 2H; 3.13 m, 2H; 3.47 m, 4H; 3.58 broad s, 4H; 3.95 t, 2H; 6.69 dd, 1H; 6.84 t, 1H; 6.95–7.19 m, 5H; 8.05 d, 2H; 10.58 s, 1H.

61: 5-[3-(2-Aminoethyl)-1H-indol-5-yloxyl-1-[4-(4-nitrophenyl)piperazin-1-yl]pentan-1-one hydrochloride The product 61A (300 mg, 0.530 mmol) is then deprotected under the conditions described for the preparation of Example 1 from 1C.

Purification of the product in the base form is carried out by chromatography on a column of silica gel eluted with a dichloromethane/methanol/aqueous ammonia (80/18/2, v/v) mixture. The pure product is isolated in the form of a yellow syrup which results, after treatment with hydrochloric acid in ether, in the compound 61 in the form of a yellow powder (211 mg, 75%).

Elemental analysis ($C_{25}H_{32}ClN_5O_4 \cdot 1.7H_2O$), % calculated: C 56.38, H 6.70, N 13.15, Cl 6.66; % found: C 56.33, H 6.58, N 12.88, Cl 7.34.

1H NMR, d6-DMSO (ppm): 1.75 m, 4H; 2.46 t, 2H; 2.99 m, 4H; 3.51 m, 4H; 3.62 broad s, 4H; 4.00 t, 2H; 6.73 dd, 1H; 6.99–7.27 m, 5H; 7.99 broad s, 3H; 8.08 d, 2H; 10.80 s, 1H.

Melting point: 120° C.

EXAMPLE 62
5-[3-(2-Aminoethyl)-1H-indol-5-yloxy]-1-[4-(aminophenyl)piperazin-1-yl]pentan-1-one hydrochloride

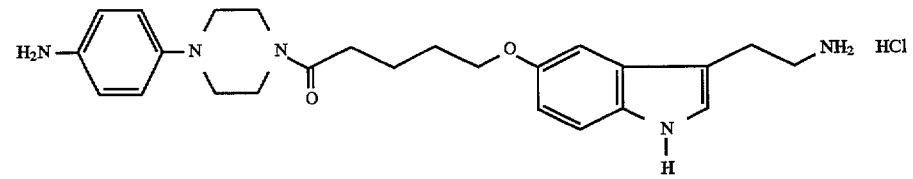

The compound 62 is prepared from the product 61A (560 mg, 0.99 mmol) under the conditions described for the preparation of Example 2.

Purification of the product in the base form is carried out by chromatography on a column of silica gel eluted with a dichloromethane/methanol/aqueous ammonia (80/18.5/1.5, v/v) mixture. The pure product is isolated in the form of a colorless syrup which results, after treatment with hydrochloric acid in ether, in the compound 62 in the form of a pink powder (270 mg, 50%).

Elemental analysis ($C_{25}H_{36}Cl_3N_5O_2 \cdot 1.5H_2O$), % calculated: C 52.50, H 6.87, N 12.24, Cl 18.59; % found: C 52.42, H 6.94, N 12.01, Cl 17.36.

1H NMR d6-DMSO (ppm): 1.72 broad s, 4H; 2.43 t, 2H; 2.97 broad s, 4H; 3.14 m, 4H; 3.62 broad s, 4H; 3.97 t, 2H; 6.71 dd, 1H; 7.06–7.24 m, 7H; 8.03 broad s, 3H; 10.79 s, 1H.

Melting point: 170° C.

EXAMPLE 63
4-[3-(2-Aminoethyl)-1H-indol-5-yloxy]-1-[4-(4-nitrophenyl)piperazin-1-yl]butan-1-one hydrochloride

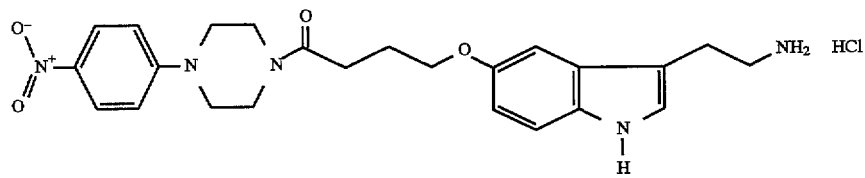

The compound 63 is prepared from (4-nitrophenyl)piperazine (2.0 g, 9.65 mmol), 4-chlorobutanoyl chloride (4.3 ml, 38.6 mmol) and the compound 1A (1.48 g, 5.36 mmol) under the conditions described for the preparation of Example 57.

Purification of the product in the base form is carried out by chromatography on a column of silica gel eluted with a dichloromethane/methanol/aqueous ammonia (80/19/1, v/v) mixture. The pure product is isolated in the form of a yellow syrup which results, after treatment with hydrochloric acid in ether, in the compound 63 in the form of a yellow powder (919 mg, 35%).

Elemental analysis ($C_{24}H_{30}ClN_5O_4 \cdot H_2O$), % calculated: C 56.97, H 6.37, N 13.84, Cl 7.01; % found: C 56.88, H 6.12, N 13.68, Cl 8.89.

1HNMR, d6-DMSO (ppm): 1.96 t, 2H; 2.54 t, 2H; 2.97 broad s, 4H; 3.49 m, 4H; 3.61 m, 4H; 4.00 t, 2H; 6.72 dd, 1H; 6.95–7.25 m, 5H; 8.05 m, 5H; 10.82 s, 1H.

Melting point: 120° C.

EXAMPLE 64
N-[4-(4-{2-[3-(2-Amino)-1H-indol-5-yloxy]acetyl}piperazin-1-yl)phenyl]-4-cyanophenylsulfonamide hydrochloride

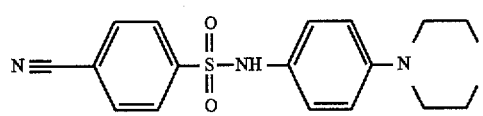

64A: N-[4-(4-(tert-Butoxycarbonyl)piperazin-1-ylphenyl)-4-cyanobenzenesulfonamide The compound 26A (3.0 g, 10.81 mmol), in solution in dichloromethane (80 ml) in the presence of triethylamine (2.21 ml, 11.89 mmol), is treated at 0° C. with 4-cyanobenzenesulfonyl chloride (2.18 g, 10.81 mmol). After stirring for 4 h from 0° C. to room temperature, 4-cyanobenzenesulfonyl chloride (0.64 g, 3.24 mmol) is again added. After 2 h 00, the reaction mixture is diluted with dichloromethane, washed with water, dried over sodium sulfate, filtered and evaporated to dryness. The dark green syrup obtained is chromatographed on a column of silica gel, eluted with a dichloromethane/acetone (25/1, v/v) mixture. The pure product is isolated in the form of a yellow syrup (3.28 g, 69%).

Elemental analysis ($C_{22}H_{26}N_4O_4S_1.0.6H_2O$), % calculated: C 58.29, H 6.07, N 12.36, % found: C 58.17, H 5.76, N 12.03.

1H NMR, d6-DMSO (ppm): 1.37 s, 9H; 2.97 t, 4H; 3.35 m, 4H; 6.83 q, 4H; 7.79 d, 2H; 8.00 d, 2H; 10.08 s, 1H.

64: N-[4-(4-{2-[3-(2-Amino)-1H-indol-5-yloxy]acetyl}-piperazin-1-yl)phenyl]-4-cyanophenylsulfonamide hydrochloride The compound 64 is prepared from the product 64A (3.2 g, 7.23 mmol) under the conditions described for the preparation of Example 26 from 26B.

Purification of the product in the base form is carried out by chromatography on a column of silica gel eluted with a dichloromethane/methanol/aqueous ammonia (85/14/1, v/v) mixture. The pure product is isolated in the form of a syrup which results, after treatment with hydrochloric acid in ether, in the compound 64 (1.1 g).

EXAMPLE 65

N-[4-(4-{2-[3-(2-Amino)-1H-indol-5-yloxy]-acetyl}piperazin-1-yl)phenyl]-4-(trifluoromethane)phenylsulfonamide hydrochloride (2.21 ml, 11.89 mmol), is treated at 0° C. with 4-(trifluoromethane)benzenesulfonyl chloride (2.64 g, 10.81 mmol). After stirring for 4 h from 0° C. to room temperature, 4-cyanobenzenesulfonyl chloride (0.75 g, 3.24 mmol) is again added. After 2 h 00, the reaction mixture is diluted with dichloromethane, washed with water, dried over sodium sulfate, filtered and evaporated to dryness. The syrup obtained is chromatographed on a column of silica gel eluted with a dichloromethane/acetone (30/1, v/v) mixture. The pure product is isolated in the form of a yellow syrup (3.50 g, 67%).

Elemental analysis ($C_{22}H_{26}N_3O_4S_1F_3.0.4H_2O$), % calculated: C 53.63, H 5.48, N 8.53; % found: C 53.61, H 5.61, N 8.40.

1H NMR, d6-DMSO (ppm): 1.41 s, 9H; 3.00 t, 4H; 3.38 m, 4H; 6.87 q, 4H; 7.91 q, 4H; 10.13 broad s, 1H.

65: N-[4-(4-{2-[3-(2-Amino)-1H-indol-5-yloxy]acetyl}-piperazin-1-yl)phenyl]-4-(trifluoromethane)phenylsulfonamide hydrochloride The compound 65 is prepared from the product 65A (3.5 g, 7.20 mmol) under the conditions described for the preparation of Example 26 from 26B.

Purification of the product in the base form is carried out by chromatography on a column of silica gel eluted with a dichloromethane/methanol/aqueous ammonia (85/14/1, v/v) mixture. The pure product is isolated in the form of a syrup which results, after treatment with hydrochloric acid in ether, in the compound 65 (0.97 g).

EXAMPLE 66

N-[4-(4-{2-[3-(2-Amino)-1H-indol-5-yloxy]-acetyl}piperazin-1-yl)phenyl]-4-methoxyphenylsulfonamide hydrochloride

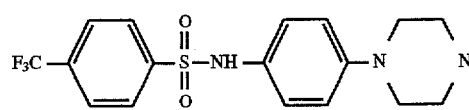

65A: N-[4-(4-(tert-Butoxycarbonyl)piperazin-1-ylphenyl)-4-(trifluoromethane)benzenesulfonamide The compound 26A (3.0 g, 10.81 mmol), in solution in dichloromethane (80 ml) in the presence of triethylamine

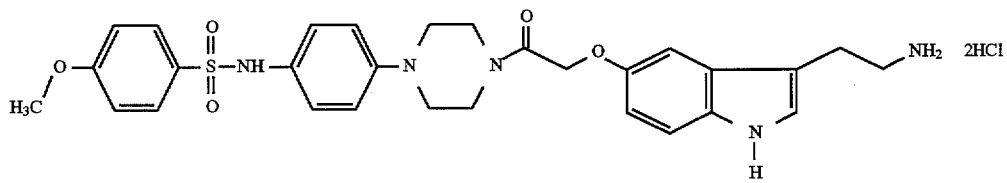

66A: N-[4-(4-(tert-Butoxycarbonyl)piperazin-1-ylphenyl)-4-methoxybenzenesulfonamide The compound 26A (3.0 g, 10.81 mmol), in solution in dichloromethane (80 ml) in the presence of triethylamine (2.21 ml, 11.89 mmol), is treated at 0° C. with 4-methoxybenzenesulfonyl chloride (2.23 g, 10.81 mmol). After stirring for 4 h from 0° C. to room temperature, 4-methoxybenzenesulfonyl chloride (0.67 g, 3.24 mmol) is again added. After 2 h 00, the reaction mixture is diluted with dichloromethane, washed with water, dried over sodium sulfate, filtered and evaporated to dryness. The syrup obtained is chromatographed on a column of silica gel eluted with a dichloromethane/acetone (30/1, v/v) mixture. The pure product is isolated in the form of a yellow syrup (4.1 g, 84%).

Elemental analysis ($C_{22}H_{29}N_3O_5S_1.0.3H_2O$), % calculated: C 58.34, H 6.59, N 9.28; % found: C 58.38, H 6.49, N 9.08.

1H NMR, d6-DMSO (ppm): 1.38 s, 9H; 2.96 t, 4H; 3.38 t, 4H; 3.77 s, 3H; 6.83 q, 4H; 7.01 d, 2H; 7.58 d, 2H; 9.69 s, 1H.

66: N-[4-(4-{2-[3-(2-Amino)-1H-indol-5-yloxy]acetyl}-piperazin-1-yl)phenyl]-4-methoxyphenylsulfonamide hydrochloride The compound 66 is prepared from the product 66A (4.1 g, 9.1 mmol) under the conditions described for the preparation of Example 26 from 26B.

Purification of the product in the base form is carried out by chromatography on a column of silica gel eluted with a dichloromethane/methanol/aqueous ammonia (85/14/1, v/v) mixture. The pure product is isolated in the form of a syrup which results, after treatment with hydrochloric acid in ether, in the compound 66 (1.6 g).

EXAMPLE 67

N-[4-(4-{2-[3-(2-Amino)-1H-indol-5-yloxy]-acetyl}piperazin-1-yl)phenyl]-4-fluorophenylsulfonamide hydrochloride sodium sulfate, filtered and evaporated to dryness. The syrup obtained is chromatographed on a column of silica gel, eluted with a dichloromethane/acetone (30/1, v/v) mixture. The pure product is isolated in the form of a yellow foam (3.6 g, 76%).

Elemental analysis ($C_{21}H_{26}N_3O_4S_1F_1.0.3H_2O$), % calculated: C 57.21, H 6.08, N 9.53; % found: C 57.36, H 6.01, N 9.45.

1H NMR, d6-DMSO (ppm): 1.39 s, 9H; 2.98 t, 4H; 3.39 t, 4H; 6.84 q, 4H; 7.36 m, 2H; 7.71 m, 2H; 9.86 s, 1H.

67: N-[4-(4-{2-[3-(2-Amino)-1H-indol-5-yloxy]acetyl}-piperazin-1-yl)phenyl]-4-fluorophenylsulfonamide hydrochloride The compound 67 is prepared from the product 67A (3.6 g, 8.26 mmol) under the conditions described for the preparation of Example 26 from 26B.

Purification of the product in the base form is carried out by chromatography on a column of silica gel eluted with a dichloromethane/methanol/aqueous ammonia (85/14/1, v/v) mixture. The pure product is isolated in the form of a syrup which results, after treatment with hydrochloric acid in ether, in the compound 67 (1.2 g).

EXAMPLE 68

N-[4-(4-{2-[3-(2-Amino)-1H-indol-5-yloxy]-acetyl}piperazin-1-yl)phenyl]-4-acetamidophenylsulfonamide hydrochloride

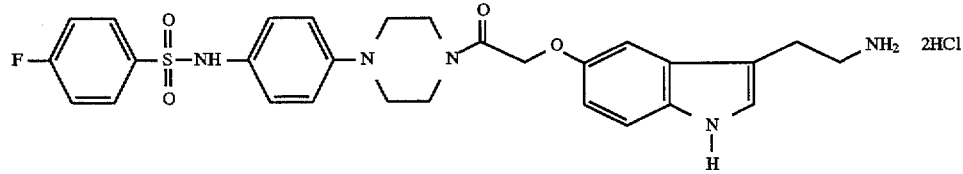

67A: N-[4-(4-(tert-Butoxycarbonyl)piperazin-1-ylphenyl)-4-fluorobenzenesulfonamide The compound 26A (3.0 g, 10.81 mmol), in solution in dichloromethane (80 ml) in the presence of triethylamine (2.21 ml, 11.89 mmol), is treated at 0° C. with 4-fluorobenzenesulfonyl chloride (2.1 g, 10.81 mmol). After stirring for 4 h from 0° C. to room temperature, 4-fluorobenzenesulfonyl chloride (0.63 g, 3.24 mmol) is again added. After 2 h 00, the reaction mixture is diluted with dichloromethane, washed with water, dried over

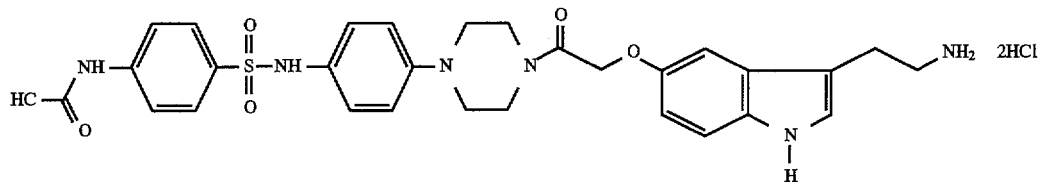

68

68A: N-[4-(4-(tert-Butoxycarbonyl)piperazin-1-ylphenyl)-4-acetamidobenzenesulfonamide The compound 26A (3.0 g, 10.81 mmol), in solution in dichloromethane (80 ml) in the presence of triethylamine (2.21 ml, 11.89 mmol), is treated at 0° C. with 4-acetamidobenzenesulfonyl chloride (2.5 g, 10.81 mmol). After stirring for 4 h from 0° to room temperature, 4-acetamidobenzenesulfonyl chloride (0.76 g, 3.24 mmol) is again added. After 1 h 00, the reaction mixture is diluted with dichloromethane, washed with water, dried over sodium sulfate, filtered and evaporated to dryness. The syrup obtained is chromatographed on a column of silica gel eluted with a dichloromethane/acetone (6/1, v/v) mixture. The pure product is isolated in the form of a purple foam (3.5 g, 69%).

Elemental analysis ($C_{23}H_{30}N_4O_5S_1.1H_2O$), % calculated: C 56.08, H 6.55, N 11.37; % found: C 56.16, H 6.29, N 11.00.

1H NMR, d6-DMSO (ppm): 1.38 s, 9H; 2.03 s, 3H; 2.95 t, 4H; 3.37 t, 4H; 6.82 q, 4H; 7.60 q, 4H; 9.70 s, 1H; 10.26 s, 1H.

68: N-[4-(4-{2-[3-(2-Amino)-1H-indol-5-yloxy]acetyl}-piperazin-1-yl)phenyl]-4-acetamidophenylsulfonamide hydrochloride The compound 68 is prepared from the product 68A (3.6 g, 8.26 mmol) under the conditions described for the preparation of Example 26 from 26B.

Purification of the product in the base form is carried out by chromatography on a column of silica gel eluted with a dichloromethane/methanol/aqueous ammonia (80/18/2, v/v) mixture. The pure product is isolated in the form of a syrup which results, after treatment with hydrochloric acid in ether, in the compound 68 (1.1 g).

EXAMPLE 69

N-[4-(4-{2-[3-(2-Amino)-1H-indol-5-yloxy]-acetyl}piperazin-1-yl)phenyl]-4-aminophenylsulfonamide hydrochloride 1H NMR, d6-DMSO (ppm): 1.37 s, 9H; 2.73 t, 2H; 3.03–3.16 m, 6H; 3.60 broad s, 4H; 4.77 s, 2H; 5.91 s, 2H; 6.50 d, 2H; 6.74–6.93 m, 6H; 7.06 dd, 2H; 7.20–7.33 m, 4H, 9.41 s, 1H; 10.66 s, 1H.

69: N-[4-(4-{2-[3-(2-Amino)-1H-indol-5-yloxy]acetyl}-piperazin-1-yl)phenyl]-4-aminophenylsulfonamide hydrochloride The compound 69A (560 mg, 0.86 mmol) is then deprotected under the conditions described for the preparation of Example 1 from 1C.

Purification of the product in the base form is carried out by chromatography on a column of silica gel eluted with a dichloromethane/methanol/aqueous ammonia (80/18/2, v/v) mixture. The pure product is isolated in the form of a colorless syrup which results, after treatment with hydrochloric acid in ether, in the compound 69 in the form of a white powder (407 mg, 72%).

Elemental analysis ($C_{28}H_{35}Cl_3N_6O_4.3.2H_2O$), % calculated: C 46.99, H 5.83, N 11.74, Cl 14.86; % found: C 46.95, H 5.82, N 11.42, Cl 14.37.

1HNMR, d6-DMSO (ppm) 2.96 broad s, 4H; 3.23 broad d, 4H; 3.71 m, 4H; 4.79 s, 2H; 6.56 d, 2H; 6.75 dd, 1H; 6.92–7.38 m, 9H; 8.01 broad s, 3H; 9.75 s, 1H; 10.82 s, 1H.

Melting point: 186° C.

EXAMPLE 70

N-[4-(4-{2-[3-(2-Amino)-1H-indol-5-yloxy]-acetyl}piperazin-1-yl)phenyl]-4-(methanesulfonylamino)phenylsulfonamide hydrochloride

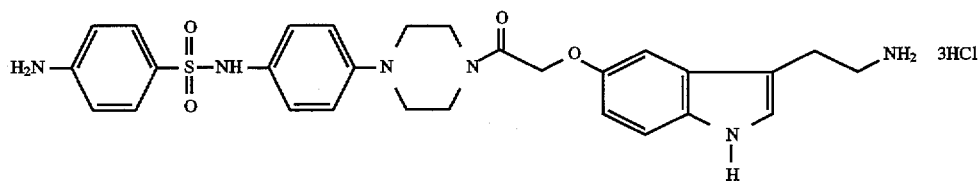

69

69A: N-[4-(4-{2-[3-(2-{N-tert-Butoxycarbonyl}amino)-1H-indol-5-yloxy]acetyl}piperazin-1-yl)phenyl]-4-aminophenylsulfonamide hydrochloride The compound 69A is prepared from the compound 26C (1.3 g, 1.96 mmol) according to the method described for the preparation of Example 2A from 1C.

The syrup obtained is chromatographed on a column of silica gel eluted with a dichloromethane/methanol/aqueous ammonia (95/4/1, v/v) mixture. The pure product is isolated in the form of an orange foam (1.2 g, 95%).

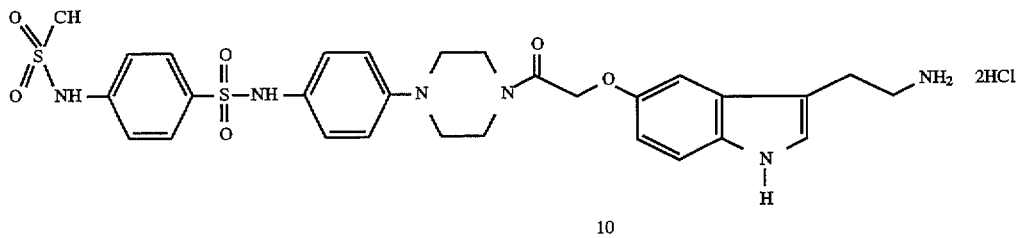

The compound 70 is prepared from the compound 69A (300 mg, 0.46 mmol) and methanesulfonyl chloride (36 μl, 1.46 mmol) according to the method described for the preparation of Example 3.

The syrup obtained is chromatographed on a column of silica gel eluted with a dichloromethane/methanol/aqueous ammonia (80/18/2, v/v) mixture. The pure product is isolated in the form of a syrup which results, after treatment with hydrochloric acid in ether, in the compound 70 (30 mg, 10%).

The specific compounds of the present invention, then, may be identified as follows:

A compound selected from the group consisting of:

2-[3-(2-Aminoethyl)-1-H-indol-5-yloxy]-1-[4-(4-nitrophenyl)piperazin-1-yl]ethanone.
2-[3-(2-Aminoethyl)-1H-indol-5-yloxy]-1-[4-(aminophenyl)piperazin-1-yl]ethanone.
N-[4-(4-{2-[3-(2-Aminoethyl)-1H-indol-5-yloxy]acetyl}-piperazin-1-yl)phenyl]acetamide.
N-[4-(4-{2-[3-(2-Aminoethyl)-1H-indol-5-yloxy]acetyl}-piperazin-1-yl)phenyl]benzamide.
N-[4-(4-{2-[3-(2-Aminoethyl)-1H-indol-5-yloxy]acetyl}-piperazin-1-yl)phenyl]methethanesulfonamide.
N-[4-(4-{2-[3-(2-Aminoethyl)-1-methylsulfonyl-1H-indol-5-yloxy]acetyl}piperazin-1-yl)phenyl]methanesulfonamide.
N-[4-(4-{2-[3-(2-Aminoethyl)-1H-indol-5-yloxy]acetyl}-piperazin-1-yl)phenyl]ethanesulfonamide.
Thiophene-2-{N-[4-(4-{2-[3-(2-aminoethyl)-1H-indol-5-yloxy]acetyl}piperazin-1-yl)phenyl]sulfonamide.
Thiophene-2-{N-[4-(4-{2-[3-(2-aminoethyl)-1-(thiophene-2-sulfonyl)-1H-indol-5-yloxy]acetyl}piperazin-1-yl)phenyl]sulfonamide.
3,5-Dimethylisoxazole-4-{N-[4-(4-{2-[3-(2-aminoethyl)-1H-indol-5-yloxy]acetyl}piperazin-1-yl)phenyl]sulfonamide.
2-[3-(2-Aminoethyl)-1H-indol-5-yloxy]-1-[4-(4-N-{ethoxycarbonyl}aminophenyl)piperazin-1-yl]ethanone.
2,2,2-Trifluoroethane [4-(4-{2-[3-(2-aminoethyl)-1H-indol-5-yloxy]acetyl}piperazin-1-yl)phenyl]sulfonamide.
N-[4-(4-{2-[3-(2-Aminoethyl)-1H-indol-5-yloxy]acetyl}piperazin-1-yl)phenyl]isopropanesulfonamide.
2-[3-(2-Aminoethyl)-1H-indol-5-yloxy]-1-[4-(2-nitrophenyl)piperazin-1-yl]ethanone.
2-[3-(2-Aminoethyl)-1H-indol-5-yloxy]-1-[4-(4-nitrophenyl)piperazin-1-yl]ethanethione.
2-[3-(2-Aminoethyl)-1H-indol-5-yloxy]-1-[4-(4-(hydroxyamino)phenyl)piperazin-1-yl]ethanone.
2-{5-[4-(4-Nitrophenylpiperazine -1-sulfonylmethoxy]-1H-indol-3-yl}ethylamine.
2-[3-(2-Aminoethyl)-1H-indol-5-yloxy]-1-[4-(4-nitrophenyl)piperazin-1-yl]propane-1-one.
2-[3-(2-(Dimethylamino)ethyl)-1H-indol-5-yloxy]-1-[4-(4-nitrophenyl)piperazin-1-yl]ethanone.
2-[3-(2-Aminoethyl)-1H-indol-5-yloxy]-1-[4-(4-(dimethylamino)phenyl)piperazin-1-yl]ethanone.
N-[4-(4-{2-[3-(2-Aminoethyl)-1H-indol-5-yloxy]acetyl}-piperazin-1-yl)phenyl]benzenesulfonamide.
2-[3-(2-Aminoethyl)-1H-indol-5-yloxy]-1-[4-(2-methoxy-4-nitrophenyl)piperazin-1-yl]ethanone.
2-(5-{2-[4-(4-Nitrophenyl)piperazin-1-yl]ethoxy}-1H-indol-3-yl)ethylamine.
3-[3-(2-Aminoethyl)-1H-indol-5-yl]-1-[4-(4-nitrophenyl)piperazin-1-yl]prop-2-en-1-one.
3-[3-(2-Aminoethyl)-1H-indol-5-yl]-1-[4-(4-nitrophenyl)piperazin-1-yl]propan-1-one.
N-[4-(4-{2-[3-(2-Aminoethyl)-1H-indol-5-yloxy]acetyl}piperazin-1-yl)phenyl]-4-nitrophenylsulfonamide.
N-[4-(4-{2-[3-(2-Aminoethyl)-1H-indol-5-yloxy]acetyl}-piperazin-1-yl)phenyl]-2-phenylacetamide.
N-[4-(4-{2-[3-(2-Aminoethyl)-1H-indol-5-yloxy]acetyl}-piperazin-1-yl)phenyl]-2-methoxybenzamide.
N-[4-(4-{2-[3-(2-Aminoethyl)-1H-indol-5-yloxy]acetyl}-piperazin-1-yl)phenyl]-2,2,2-trifluoroacetamide.
3-[4-(4-{2-[3-(2-Aminoethyl)-1H-indol-5-yloxy]acetyl}-piperazin-1-yl)phenyl]-1,1-dimethylsulfonurea.
Thiophene-2-carboxylic acid [4-(4-{2-[3-2-aminoethyl)indol-5-yloxy]acetyl}piperazin-1-yl)phenyl]amide.
N-[4-(4-{2-[3-(2-Aminoethyl)-1H-indol-5-yloxy]acetyl}-piperazin-1-yl)phenyl]phenylcarbamate.
N-[4-(4-{2-[3-(2-Aminoethyl)-1H-indol-5-yloxy]acetyl}-piperazin-1-yl)phenyl]-4-nitrobenzamide.
N-[4-(4-{2-[3-(2-Aminoethyl)-1H-indol-5-yloxy]acetyl}-piperazin-1-yl)phenyl]methylcarbamate.
3-[3-(2-Aminoethyl)-1H-indol-5-yl]-1-[4-(4-aminophenyl)-piperazin-1-yl]propan-1-one.
N-[4-(4-{3-[3-(2-Aminoethyl)-1H-indol-5-yl]propionyl}-piperazin-1-yl)phenyl]methanesulfonamide.
N-[4-(4-{3-[3-(2-Aminoethyl)-1H-indol-5-yl]propionyl}-piperazin-1-yl)phenyl]-N-dimethylsulfonylurea.
N-[4-(4-{3-[3-(2-Aminoethyl)-1H-indol-5-yl]propionyl}-piperazin-1-yl)phenyl]-4-nitrobenzenesulfonamide.
N-[4-(4-{3-[3-(2-Aminoethyl)-1H-indol-5-yl]propionyl}-piperazin-1-yl)phenyl]benzamide.
4-(4-{2-[3-(2-Aminoethyl)-1H-indol-5-yloxy]-ethyl}piperazin-1-yl)phenylamine.
N-[4-(4-{2-[3-(2-Aminoethyl)-1H-indol-5-yloxy]ethyl}piperazin-1-yl)phenyl]methanesulfonamide.
N-[4-(4-{2-[3-(2-Aminoethyl)-1H-indol-5-yloxy]acetyl}-piperazin-1-yl)phenyl]methylcarbamate.
2-(5-{2-[4-(2-Methoxy-4-nitrophenyl)piperazin-1-yl)-ethoxy}-1-H-indol-3-yl)ethylamine.
4-(4-{2-[3-(2-Aminoethyl)-1H-indol-5-yloxy]ethyl}-piperazin-1-yl)benzonitrile.
[2-(5-{2-[4-(4-(Aminomethyl)phenyl)piperazin-1-yl]ethoxy}-1H-indol-3-yl)ethyl]methylamine.
2-(4-{2-[3-(2-Aminoethyl)-1H-indol-5-yloxy]-acetyl}piperazin-1-yl)benzonitrile.
2-[3-(2-Aminoethyl)-1H-indol-5-yloxy]-1-[4-(2-aminomethylphenyl)piperazin-1-yl]ethanone.
N-[2-[4-{2-[3-(2-Aminoethyl)-1H-indol-5-yloxy]acetyl}-piperazin-1-yl)benzylmethanesulfonamide.
N-[2-[4-{2-[3-(2-Aminoethyl)-1H-indol-5-yloxy]acetyl}-piperazin-1-yl]benzenesulfonamide.
4-(4-{2-[3-(2-Aminoethyl)-1H-indol-5-yloxy]acetyl}-piperazin-1-yl)benzonitrile.

2-[3-(2-Aminoethyl)-1H-indol-5-yloxy]-1-[4-(4-(aminomethyl)phenyl)piperazin-1-yl]ethanone.

N-[4-(4-{2-[3-(2-Aminoethyl)-1H-indol-5-yloxy]acetyl}-piperazin-1-yl)benzyl]methane sulfonamide.

2-[3-(2-Aminoethyl)-1H-indol-5-yloxy]-1-[4-(4-amino-2-methoxyphenyl)piperazin-1-yl]ethanone.

N-[4-(4-{2-[3-(2-Aminoethyl)-1H-indol-5-yloxy]acetyl}-piperazin-1-yl)-3-methoxyphenyl]methanesulfonamide.

2-[3-(2-Aminoethyl)-1H-indol-5-yloxy]-1-[4-(4-nitronaphth-1-yl)piperazin-1-yl]ethanone.

4-(4-{2-[3-(2-Aminoethyl)-1H-indol-5-yloxy]acetyl}-piperazin-1-yl)phenyl methanesulfonate.

6-[3-(2-Aminoethyl)-1H-indol-5-yloxy]-1-[4-(4-nitrophenyl)piperazin-1-yl]hexan-1-one.

6-[3-(2-Aminoethyl)-1H-indol-5-yloxy]-1-[4-(4-aminophenyl)piperazin-1-yl]hexan-1-one.

N-[4-(4-{6-[3-(2-Aminoethyl)-1H-indol-5-yloxy]hexanoyl}-piperazin-1-yl)phenyl]methanesulfonamide.

N-[4-(4-{6-[3-(2-Aminoethyl)-1H-indol-5-yloxy]hexanoyl}-piperazin-1-yl)benzyl]benzenesulfonamide.

5-[3-(2-Aminoethyl)-1H-indol-5-yloxy]-1-[4-(4-nitrophenyl)piperazin-1-yl]pentan-1-one.

5-[3-(2-Aminoethyl)-1H-indol-5-yloxy]-1-[4-(4-(aminophenyl)-piperazin-1-yl]-pentan-1-one.

4-[3-(2-Aminoethyl)-1H-indol-5-yloxy]-1-[4-(4-nitrophenyl)piperazin-1-yl]butan-1-one.

N-[4-(4-{2-[3-(2-Amino)-1H-indol-5-yloxy]acetyl}-piperazin-1-yl)phenyl]-4-cyanophenylsulfonamide.

N-[4-(4-{2-[3-(2-Amino)-1H-indol-5-yloxy]acetyl}-piperazin-1-yl)phenyl]-4-(trifluoromethane)phenyl sulfonamide.

N-[4-(4-{2-[3-(2-Amino)-1H-indol-5-yloxy]acetyl}-piperazin-1-yl)phenyl]-4-methoxyphenylsulfonamide.

N-[4-(4-{2-[3-(2-Amino)-1H-indol-5-yloxy]acetyl}-piperazin-1-yl)phenyl]-4-fluorophenylsulfonamide.

N-[4-(4-{2-[3-(2-Amino)-1H-indol-5-yloxy]acetyl}-piperazin-1-yl)phenyl]-4-acetamidophenylsulfonamide.

N-[4-(4-{2-[3-(2-Amino)-1H-indol-5-yloxy]acetyl}-piperazin-1-yl)phenyl]-4-aminophenylsulfonamide.

N-[4-(4-{2-[3-(2-Amino)-1H-indol-5-yloxy]acetyl}-piperazin-1-yl)phenyl]-4-(methanesulfonylamino)phenylsulfonamide, and their salts which are acceptable for therapeutic use.

STUDY OF THE AFFINITY FOR 5-HT$_{1D}$ RECEPTORS

This study is carried out according to the technique described by Pauwells et al. (Biochem. Pharmacol, 46, 535–538, 1993).

Preparation of the membranes

Sheep brains are removed in the local abattoir and transported in ice. The caudate nuclei are removed, weighed and homogenized with a Polytron for 20 sec (speed 6–7) in 20 volumes of Tris-HCl 50 mM, pH 7.7. The homogenate is centrifuged for 10 min at 48,000 g with an L5 50E centrifuge (Beckman).

The pellet, taken up in 20 volumes of Tris-HCl 50 mm, pH 7.7, is placed in a water bath at 37° C. for 10 min and then recentrifuged for 10 min at 48,000 g. The pellet then obtained is immediately frozen in fractions containing 0.5g of tissue.

Affinities

The pellet is defrosted and homogenized with a Dounce in 80 volumes of Tris-HCl 50 mM, pH 7.7, containing 4 mM CaCl$_2$, 10 μM of pargyline and 0.1% of ascorbic acid.

Affinity is produced at 25° C. by incubating for 30 min: 0.1 ml of buffer or 10 μM, as final concentration, of sumatriptan, in order to obtain the non-specific binding 0.8 ml of membrane 0.1 ml of 3H–5HT (15 to 30 Ci:mM, New England Nuclear France).

The incubation is brought to an end by rapid filtration through GF/B filters and rinsing with 3 times 3 [illegible] ice-cold buffer, using a harvester manufactured by Brandel which makes it possible [illegible] to filter [illegible] samples. The filters are introduced into vials containing [illegible]ml of [illegible] [illegible] scintillant (Packard) and the radioactivity measured with a Tri-carb 4640 counter (Packard). The IC$_{50}$ (concentration which inhibits the specific affinity by 50%) is determined graphically.

The affinities of the various products which form part of this invention for 5HT$_{1A}$ and 5HT$_{1B}$ receptors were measured according to the techniques described in:

Peroutka S. J. Pharmacological differentiation and characterization of 5HT$_{1A}$, 5HT$_{1B}$ and 5HT$_{1C}$ binding sites in rat frontal cortex. J. Neurochem., 45, 529–540, 1986.

Examples of the affinity profile of several molecules (IC$_{50}$ × 10–9M)

| Example* | 5-HT$_{1D}$ mean | 5-HT$_{1A}$ mean | Ratio# 1A/1D |
|---|---|---|---|
| 4 | 1 | 75 | 75 |
| 6 | 4.3 | 79 | 18 |
| 7 | 1.6 | 44 | 28 |
| 8 | 1.2 | 26 | 22 |
| 9 | 5 | 38 | 8 |
| 10 | 1 | 20 | 20 |
| 11 | 2.4 | 105 | 44 |
| 14 | 1 | 9.5 | 10 |

*The examples are the ones described in the text in order to illustrate the invention
Ratio of the IC$_{50}$ values of each product for the 5-HT$_{1A}$ and 5-HT$_{1D}$ receptors

STUDY OF THE AGONIST ACTIVITY WITH RESPECT TO THE 5-HT$_{1B}$ RECEPTORS

The measurements were carried out with respect to the inhibition of the formation of cAMP stimulated by forskolin, mediated by a 5-HT$_{1B}$ receptor, in an OK kidney epithelial cell line as described elsewhere (P. J. Pauwels and C. Palmier, Neuropharmacology, awaiting publication).

The studies carried out show that the majority of the products of the invention, like serotonin, are capable of effectively blocking the formation of cAMP in this test. Thus, Examples 1, 2, 3 and 5 have an EC$_{50}$ of between 0.3 and 1.2 nM.

Study of the affinity and of the agonist activity with respect to human receptors Human 5HT$_{1Da}$ and 5HT$_{1Db}$ receptors were cloned according to the sequences published by M. Hamblin and M. Metcalf, Mol. Pharmacol., 40, 143 (1991) and Weinshenk et al., Proc. Natl. Acad. Sci., 89, 3630 (1992).

The transient transfection and the stable transfection of the genes of these receptors was carried out in Cos-7 and CHO-K$_1$ cell lines by using an electroporator.

The HeLa HA7 cell line expressing the 5HT$_{1A}$ human receptor was obtained from Tulco (Duke Univ., Durham, N.C., USA) and cultured according to the method of Fargin et al., J. Biol. Chem., 264, 14848 (1989).

The binding of the derivatives of the present invention with human 5HT$_{1Da}$, 5HT$_{1Db}$ and 5HT$_{1A}$ receptors was studied according to the method described by P. Pauwels and C. Palmier (Neuropharmacology, 33, 67, 1994).

The incubation media for these binding measurements comprise 0.4 ml of cell membrane preparation, 0.05 ml of a tritiated ligand [[3H]-SCT (final concentration: 2 nM) for the $5HT_{1Da}$ and $5HT_{1Db}$ receptors and [3H]-80H-DPAT (final concentration: 1 nM) for the $5HT_{1A}$ receptor] and 0.05 ml of the molecule to be tested (final concentrations from 0.1 nM to 1000 nM) or 10 µM (final concentration) of serotonin ($5HT_{1Da}$ and $5HT_{1Db}$) or 1 µM (final concentration) of spiroxatrin ($5HT_{1A}$).

The inhibition of the formation of cyclic AMP (stimulated by forskolin) mediated by the human $5HT_{1Db}$ receptor was studied in CHO-K1 cells transfected by the receptor according to the technique described previously for the $5HT_{1B}$ receptor (P. Pauwels and C. Palmier, Neuropharmacology, 33, 67, 1994).

Illustration of the profile of several molecules of the present invention

| Example | Ki (nM) | | | $EC_{50}$* (nM) |
| --- | --- | --- | --- | --- |
| | $5HT_{1Da}$ | $5HT_{1Db}$ | $5HT_{1A}$ | |
| 1 | 0.5 | 1 | 25 | 1.2 |
| 3 | 1.7 | 3.3 | 78.6 | 20 |
| 5 | 0.7 | 3.2 | 73 | 6.5 |
| 26 | 0.25 | 0.5 | 16.5 | 6.5 |
| 33 | 2.8 | 2 | 39 | 9 |
| 41 | 1.1 | 0.7 | 28 | 2.6 |
| 59 | 1.3 | 1.3 | 9.3 | 0.52 |

*Inhibition of the $5HT_{1Db}$ cyclase stimulated by forskolin

The several examples described above clearly show that the products of the present invention are excellent ligands for human $5HT_{1Da}$ and $5HT_{1Db}$ receptors and are excellent agonists with respect to the human $5HT_{1Db}$ receptor.

The new arylpiperazine-derived indole compounds which form part of this invention are ligands having an exceptional affinity for the $5-HT_{1D}$ and $5-HT_{1B}$ receptors, as is demonstrated by the examples described above. Many compounds which are an integral part of the present invention have the additional advantage of being particularly selective for the 5 $HT_{1D}$ receptor with respect to the 5 $HT_{1A}$, 5 $HT_{1C}$, 5 $HT_2$, $\alpha_1$, $\alpha_2$ and $D_2$ receptors. The selectivity of the compounds of the present invention and in particular their preferential affinity for the 5 $HT_{1D}$ receptor with respect to the 5 $HT_{1A}$ receptor represents a very important advantage with respect to the ligands of the 5 $HT_{1D}$ receptor known to date (cf. Annual Reports in Medicinal Chemistry, vol. 27, chapter 3, p. 25; Academic Press, 1992).

In human therapeutics, the compounds of general formula (I) according to the invention are particularly useful in the treatment and prevention of disorders related to serotonin in the central nervous system and in the vascular system. These compounds can therefore be used in the treatment and prevention of depression, compulsive obsessional disorders, eating disorders, such as bulimia and anorexia, aggressiveness, alcoholism, nicotine addiction, hypertension, nausea, sexual dysfunctioning, asocial behavior, anxiety, migraine, Alzheimer's disease and memory disorders.

The present invention also relates to the medicaments comprising at least one compound of formula (I) in the pure state or in the form of a composition in which it is combined with any other pharmaceutically compatible product, which can be inert or physiologically active. The medicaments according to the invention can be employed orally, parenterally, rectally or topically.

Tablets, pills, powders (gelatin capsules or cachets) or granules can be used as solid compositions for oral administration. In these compositions, the active principle according to the invention is mixed with one or a number of inert diluents, such as starch, cellulose, sucrose, lactose or silica, under an argon stream. These compositions can also comprise substances other than the diluents, for example one or a number of lubricating agents such as magnesium stearate or talc, a coloring agent, a coating agent (dragées) or a varnish.

Pharmaceutically acceptable solutions, suspensions, emulsions, syrups and elixirs containing inert diluents such as water, ethanol, glycerol, vegetable oils or paraffin oil can be used as liquid compositions for oral administration. These compositions can comprise substances other than the diluents, for example wetting, sweetening, thickening, flavoring or stabilizing substances.

The sterile compositions for parenteral administration can preferably be suspensions, emulsions or nonaqueous or aqueous solutions. Water, propylene glycol, a polyethylene glycol, vegetable oils, in particular olive oil, injectable organic esters, for example ethyl oleate, or other suitable organic solvents can be used as solvent or vehicle. These compositions can also contain adjuvants, in particular wetting, isotonizing, emulsifying, dispersing and stabilizing agents. Sterilization can be carried out in several ways, for example by aseptic filtration, by incorporating sterilizing agents in the composition, by irradiation or by heating. They can also be prepared in the form of solid sterile compositions which can be dissolved at the time of use in sterile water or any other injectable sterile medium.

The compositions for rectal administration are suppositories or rectal capsules which contain, besides the active product, excipients such as cocoa butter, semi-synthetic glycerides or poly(ethylene glycol)s.

The compositions for topical administration can be, for example, creams, lotions, eyedrops, mouthwashes, nosedrops or aerosols.

The doses depend on the desired effect, on the duration of treatment and on the administration route used; they are generally between 0.001 g and 1 g (preferably between 0.005 g and 0.25 g) per day, preferably orally, for an adult with unit doses ranging from 0.1 mg to 500 mg of active substance and preferably from 1 mg to 50 mg.

Generally, the doctor will determine the appropriate dosage depending on the age, weight and all the other factors specific to the subject to be treated. The following examples illustrate compositions according to the invention [in these examples, the term "active component" denotes one or a number (generally one) of the compounds of formula (I) according to the present invention]:

Tablets

They can be prepared by direct compression or by passing through a wet granulation. The procedure by direct compression is preferred but it may not be suitable in all cases, depending on the doses and the physical properties of the active component.

A—By direct compression

| | mg for 1 tablet |
| --- | --- |
| Active component | 10.0 |
| Microcrystalline cellulose, B.P.C. | 89.5 |
| Magnesium stearate | 0.5 |
| | 100.0 |

The active component is passed through a sieve with a mesh size of 250 µm per side, mixing is carried out with the excipients and compression is carried out using 6.0 mm dies. Tablets having other mechanical strengths can be prepared by modifying the compressive weight with use of appropriate dies.

B—Wet granulation

|  | mg for one tablet |
| --- | --- |
| Active component | 10.0 |
| Lactose, pharmaceutical grade | 74.5 |
| Starch, pharmaceutical grade | 10.0 |
| Pregelatinized maize starch, pharmaceutical grade | 5.0 |
| Magnesium stearate | 0.5 |
| Weight at compression | 100.0 |

The active component is passed through a sieve with a mesh size of 250 µm and mixing is carried out with the lactose, the starch and the pregelatinized starch. The mixed powders are moistened-with purified water, granulation is carried out, drying is carried out, sieving is carried out and mixing with magnesium stearate is carried out. The lubricated granules are compressed as in the direct compression formulae. A thin coating layer can also be applied to the tablets by means of appropriate film-forming materials, for example methylcellulose or hydroxypropylmethylcellulose, according to conventional techniques. The tablets can also be coated with sugar.

Capsules

|  | mg for one capsule |
| --- | --- |
| Active component | 10.0 |
| *Starch 1500 | 89.5 |
| Magnesium stearate, pharmaceutical grade | 0.5 |
| Filling weight | 100.0 |

*a form of directly compressible starch supplied by the firm Colorcon Ltd, Orpington, Kent, United Kingdom.

The active component is passed through a sieve with a mesh size of 250 µm and mixing with the other substances is carried out. The mixture is introduced into hard gelatin No. 2 capsules on a suitable filling machine. Other dosage units can be prepared by modifying the filling weight and, when necessary, by changing the size of the capsule.

Syrup

|  | mg per dose of 5 ml |
| --- | --- |
| Active component | 10.0 |
| Sucrose, pharmaceutical grade | 2750.0 |
| Glycerol, pharmaceutical grade | 500.0 |
| Buffer Flavor Colorant Preservative | q.s. |
| Distilled water | 5.0 |

The active component, the buffer, the flavor, the colorant and the preservative are dissolved in part of the water and the glycerol is added. The remainder of the water is heated to 80° C. and the sucrose is dissolved therein and the solution is then cooled. The two solutions are combined, the volume is adjusted and mixing is carried out. The syrup obtained is clarified by filtration.

Suppositories

| Active component |  | 10.0 mg |
| --- | --- | --- |
| *Witepsol H15 | remainder to | 1.0 g |

*Tradename for Adeps Solidus from the European Pharmacopeia.

A suspension of the active component in Witepsol H15 is prepared and it is introduced into an appropriate machine with 1 g suppository molds.

Liquid for administration by intravenous injection

|  | g/l |
| --- | --- |
| Active component | 2.0 |
| Water for Injection, pharmaceutical grade remainder to | 1000.0 |

It is possible to add sodium chloride in order to adjust the tonicity of the solution and to adjust the pH to the maximum stability and/or in order to facilitate dissolution of the active component by means of a dilute alkali or acid or by adding appropriate buffer salts. The solution is prepared, is clarified and is introduced into phials of appropriate size which are sealed by melting the glass. It is also possible to sterilize the liquid for injection by heating in an autoclave according to one of the acceptable cycles. It is also possible to sterilize the solution by filtration and to introduce into a sterile phial under aseptic conditions. The solution can be introduced into the phials under a gaseous atmosphere.

Cartridges for inhalation

|  | g/cartridge |
| --- | --- |
| Mironized active component | 1.0 |
| Lactose, pharmaceutical grade | 39.0 |

The active component is micronized in a fluid-energy mill and converted to the form of fine particles before mixing with lactose for tablets in a high energy mixer. The pulverulent mixture is introduced into hard gelatin No. 3 capsules on an appropriate encapsulating machine. The contents of the cartridges are administered using a powder inhaler.

Pressurized aerosol with a metering valve

|  | mg/dose | per 1 container |
| --- | --- | --- |
| Micronized active component | 0.500 | 120 mg |
| Oleic acid, pharmaceutical grade | 0.050 | 12 mg |
| Trichloroofluoromethane for pharmaceutical use | 22.25 | 5.34 g |
| Dichlorodifluoromethane for pharmaceutical use | 60.90 | 14.62 g |

The active component is micronized in a fluid-energy mill and reduced to the form of fine particles. The oleic acid is mixed with the trochlorofluoromethane at a temperature of 10°–15° C. and the micronized medicament is introduced into the solution using a mixer with a high shearing effect. The suspension is introduced in a measured amount into aluminum aerosol containers to which are attached appropriate metering valves delivering a dose of 85 mg of the suspension; the dichlorodifluoromethane is introduced into the containers by injection through the valves.

We claim:
1. A compound selected from those corresponding to the formula

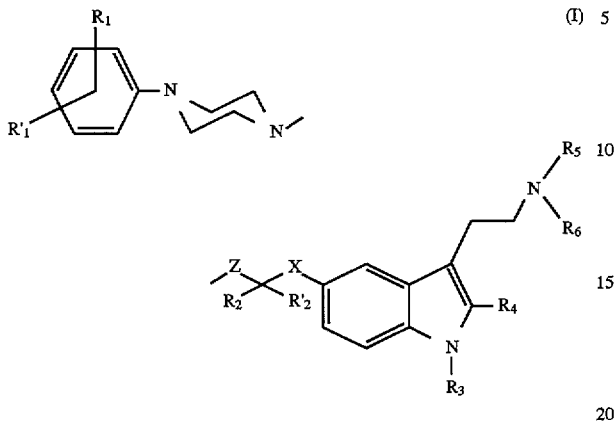

(I)

in which:

$R_1$ represents an $NH_2$, $NO_2$, $NH-NH_2$, $NH-OH$, $NCOR_7(OH)$, $NR_5R_6$, $NHCOR_7$, $NHCONR_5R_7$, $NHSO_2R_7$, $NHCO_2R_7$, $SO_2R_7$, $SO_2NHR_7$, $NHCH_2SR_7$, $NHCH_2S(O)R_7$, $NHCH_2SO_2R_7$, CN, $NHCONH_2$, $SO_2NH_2$, $N(SO_2R_6)$, $CH_2NHCOR_7$, $CH_2NHCONR_5R_6$, $CH_2NHSO_2R_7$, $CH_2NHCO_2R_7$, or $OSO_2R_7$ radical which can be in the o, m, or p position on the aromatic ring, $R'_1$ represents a substituent which can be in various positions on the aromatic ring, selected from H, methyl, ethyl, propyl, isopropyl, n-butyl, s-butyl, t-butyl, trifluoromethyl, 2,2,2-trifluoroethyl, phenyl, benzyl, phenethyl, cycloalkyl, OH, $SR_5$, $OR_5$, chlorine, fluorine, bromine, and iodine or alternatively R' can be identical to $R_1$, Z represents C=O, C=S, $SO_2$, $(CH_2)_n$, or $-CO(CH_2)_n-$ in which n is 1 to 5, inclusive, $R_2$ and $R'_2$, which are identical or different, each represent a hydrogen atom, a linear or branched alkyl radical, or a phenyl, benzyl, cycloalkyl, or phenyl-alkyl radical which is optionally substituted by a substituent chosen from halogen alkyl, phenyl, carbonyl-derived $C_1$-$C_6$ acyl, alkoxy, and alkylthio radicals, X represents $CH_2$ or O; the $-C(R_2R'_2)-X$ group can also represent a C=C double bond, $R_3$ represents a hydrogen atom, a linear or branched alkyl radical, or a phenyl, $COR_7$, $CO_2$, $CO_2R_7$, $CONHR_7$, or $SO_2R_7$ radical.

$R_4$ represents a hydrogen, chlorine, fluorine, or bromine atom, or a linear or branched alkyl radical, $R_5$ and $R_6$, which are identical or different, each represent a hydrogen atom, a linear or branched alkyl radical selected from methyl, ethyl, n-propyl, isopropyl, n-butyl, s-butyl, and t-butyl, or an arylalkyl radical selected from benzyl and phenethyl, $R_7$ represents a linear or branched alkyl radical having 1 to 5 carbon atoms inclusive, trifluoromethyl, 2,2,2-trifluoroethyl, phenyl, a heterocycle selected from thiophene and isoxazole, or arylalkyl selected from benzyl and phenethyl in which the aromatic ring may be variously substituted in various positions by methyl, ethyl, propyl or butyl, trifluoromethyl, 2,2,2-trifluoroethyl, hydroxyl, thiol, $OCH_3$, $OC_2H_5$ or $OCH(Me)_2$, $SCH_3$ or $SC_2H_5$, chlorine, fluorine, bromine, or iodine, nitrile, $COR_5$, $CO_2R_5$, $NO_2$, $NR_5R_6$, $NHSO_2R_5$, $NHCO_2R_5$, $NHCOR_5$, $NHCONR_5R_6$ or $NHSO_2NR_5R_6$, and its salts which are acceptable in therapeutic use.

2. A compound selected from the group consisting of:

2-[3-(2-Aminoethyl)-1-H-indol-5-yloxy]-1-(4-nitrophenyl)piperazin-1-yl]ethanone, 2-[3-(2-Aminoethyl)-1H-indol-5-yloxy]1-[4-(aminophenyl)piperazin-1-yl]ethanone, N-[4-(4-{2-[3-(2-Aminoethyl)-1H-indol-5-yloxy]acetyl}-piperazin-1-yl)phenyl]acetamide, N-[4-(4-{2-[3-(2-Aminoethyl)-1H-indol-5-yloxy]acetyl}-piperazin-1-yl)phenyl]benzamide, N-[4-(4-{2-[3-(2-Aminoethyl)-1H-indol-5-yloxy]acetyl}-piperazin-1-yl)phenyl]methanesulfonamide, N-[4-(4-{2-[3-(2-Aminoethyl)-1-methylsulfonyl-1H-indol-5-yloxy]acetyl}piperazin-1-yl)phenyl]methanesulfonamide, N-[4-(4-{2-[3-(2-Aminoethyl)-1H-indol-5-yloxy]acetyl}-piperazin-1-yl)phenyl]ethanesulfonamide, Thiophene-2-{N-[4-(4-{2-[3-(2-aminoethyl)-1H-indol-5-yloxy]acetyl}piperazin-1-yl)phenyl]sulfonamide, Thiophene-2-{N-[4-(4-{2-[3-(2-aminoethyl)-1-(thiophene-2-sulfonyl)-1H-indol-5-yloxy]acetyl}piperazin-1-yl)phenyl]sulfonamide, 3,5-Dimethylisoxazole-4-{N-[4-(4-{2-[3-(2-aminoethyl)-1H-indol-5 -yloxy]acetyl}piperazin-1-yl)phenyl]sulfonamide, 2-[3-(2-Aminoethyl)-1H -indol-5-yloxy]-1-[4-(4-N-{ethoxycarbonyl}aminophenyl)piperazin-1-yl]ethanone, 2,2,2-Trifluoroethane [4-(4-{2-[3-(2-aminoethyl)-1H-indol-5-yloxy]acetyl}piperazin-1-yl)phenyl]sulfonamide, N-[4-(4-{2-[3-(2-Aminoethyl)-1H-indol-5-yloxy]acetyl}-piperazin-1-yl)phenyl]isopropanesulfonamide, 2-[3-(2-Aminoethyl)-1H-indol-5-yloxy]-1-[4-(2-nitrophenyl)piperazin-1-yl)ethanone, 2-[3-(2-Aminoethyl)-1H-indol-5-yloxy]-1-[4-(4-nitrophenyl)piperazin-1-yl)ethanethione, 2-[3-(2-Aminoethyl)-1H-indol-5-yloxy]-1-[4-(4-(hydroxysunino)phenyl)piperazin-1-yl)ethanone, 2-{5-[4-(4-Nitrophenylpiperazine-1-sulfonylmethoxy]-1H-indol-3-yl}ethylamine, 2-[3-(2-Aminoethyl)-1H-indol-5-yloxy]-1-[4-(4-nitrophenyl)piperazin-1-yl]propane-1-one, 2-[3-(2-(Dimethylamino)ethyl)-1H-indol-5-yloxy]-1-[4-(4-nitrophenyl)piperazin-1-yl]ethanone, 2-[3-(2-Aminoethyl)-1H-indol-5-yloxy]-1-[4-(4-(dimethylamino)phenyl)piperazin-1-yl]ethanone, N-[4-(4-{2-[3-(2-Aminoethyl)-1H-indol-5-yloxy]acetyl}-piperazin-1-yl)phenyl]benzenesulfonamide, 2-[3-(2-Aminoethyl)-1H-indol-5-yloxy]-1-[4-(2-methoxy-4-nitrophenyl)piperazin-1-yl]ethanone, 2-(5-{2-[4-(4-Nitrophenyl)piperazin-1-yl]ethoxy}-1H-indol-3-yl)ethylamine, 3-[3-(2-Aminoethyl)-1H-indol-5-yl]-1-[4-(4-nitrophenyl) piperazin-1-yl]prop-2-en-1-one, 3-[3-(2-Aminoethyl)-1H-indol-5-yl]-1-[4-(4-nitrophenyl) piperazin-1-yl]propan-1-one, N-[4-(4-{2-[3-(2-Aminoethyl)-1H-indol-5-yloxy] acetyl}piperazin-1-yl)phenyl]-4-nitrophenylsulfonamide, N-[4-(4-{2-[3-(2-Aminoethyl)-1H-indol-5-yloxy] acetyl}-piperazin-1-yl)phenyl]-2-phenylacetamide, N-[4-(4-{2-[3-(2-Aminoethyl)-1H-indol-5-yloxy] acetyl}-piperazin-1-yl)phenyl]-2-methoxybenzamide, N-[4-(4-{2-[3-(2-Aminoethyl)-1H-indol-5-yloxy] acetyl}-piperazin-1-yl)phenyl]-2,2,2-trifluoroacetamide, 3-[4-(4-{2-[3-(2-Aminoethyl)-1H-indol-5-yloxy]acetyl}-piperazin-1-yl)phenyl]-1,1-dimethylsulfonurea, Thiophene-2-carboxylic acid [4-(4-{2-[3-2-aminoethyl)-1H-indol-5-yloxy]acetyl}piperazin-1-yl)phenyl]amide, N-[4-(4-{2-[3-(2-Aminoethyl)-1H-indol-5-yloxy] acetyl}-piperazin-1-yl)phenyl]phenylcarbamate, N-[4-(4-{2-[3-(2-Aminoethyl)-1H-indol-5-yloxy] acetyl}-piperazin-1-yl)phenyl]-4-nitrobenzamide, N-[4-(4-{2-[3-(2-Aminoethyl)-1H-indol-5-yloxy] acetyl}-piperazin-1-yl)phenyl]methylcarbamate, 3-[3-(2-Aminoethyl)-1H-indol-5-yl]-1-[4-(4-aminophenyl)-piperazin-1-yl]propan-1-one, N-[4-(4-{3-[3-(2-Aminoethyl)-1H-indol-5-yl] propionyl}-piperazin-1-yl)phenyl] methanesulfonamide, N-[4-(4-{3-[3-(2-Aminoethyl)-1H-indol-5-yl] propionyl}-piperazin-1-yl)phenyl]-N-dimethylsulfonylurea, N-[4-(4-{3-[3-(2-Aminoethyl)-1H-indol-5-yl] propionyl}-piperazin-1-yl)phenyl]-4-nitrobenzenesulfonamide, N-[4-(4-{3-[3-(2-Aminoethyl)-1H-indol-5-yl] propionyl}-piperazin-1-yl)phenyl]benzamide, 4-(4-{2-[3-(2-Aminoethyl)-1H-indol-5-yloxy]-ethyl}piperazin-1-yl)phenylamine, N-[4-(4-{2-[3-(2-Aminoethyl)-1H-indol-5-yloxy] ethyl}piperazin-1-yl)phenyl]methanesulfonamide, N-[4-(4-{2-[3-(2-Aminoethyl)-1H-indol-5-yloxy] acetyl}-piperazin-1-yl)phenyl]methylcarbamate, 2-(5-{2-[4-(2-Methoxy-4-nitrophenyl)piperazin-1-yl)-ethoxy}-1-H-indol-3-yl)ethylamine, 4-(4-{2-[3-(2-Aminoethyl)-1H-indol-5-yloxy]ethyl}-piperazin-1-yl)benzonitrile,

[2-(5-{2-[4-(4-(Aminomethyl)phenyl)piperazin-1-yl] ethoxy}-1H-indol-3-yl)ethyl]methylamine, 2-(4-{2-[3-(2-Aminoethyl)-1H-indol-5-yloxy]-acetyl}piperazin-1-yl)benzonitrile, 2-[3-(2-Aminoethyl)-1H-indol-5-yloxy]-1-[4-(2-aminomethylphenyl)piperazin-1-yl]ethanone, N-[2-[4-{2-[3-(2-Aminoethyl)-1H-indol-5-yloxy] acetyl}-piperazin-1-yl)benzylmethanesulfonamide, N-[2-(4-{2-[3-(2-Aminoethyl)-1H-indol-5-yloxy] acetyl}-piperazin-1-yl]benzenesulfonamide, 4-(4-{2-[3-(2-Aminoethyl)-1H-indol-5-yloxy]acetyl}-piperazin-1-yl)benzonitrile, 2-[3-(2-Aminoethyl)-1H-indol-5-yloxy]-1-[4-(4-(aminomethyl)phenyl)piperazin-1-yl]ethanone, N-[4-(4-{2-[3-(2-Aminoethyl)-1H-indol-5-yloxy] acetyl}-piperazin-1-yl)benzyl]methane sulfonamide, 2-[3-(2-Aminoethyl)-1H-indol-5-yloxy]-1-[4-(4-amino-2-methoxyphenyl)piperazin-1-yl]ethanone, N-[4-(4-{2-[3-(2-Aminoethyl)-1H-indol-5-yloxy] acetyl}-piperazin-1-yl)-3-methoxyphenyl] methanesulfonamide, 2-[3-(2-Aminoethyl)-1H-indol-5-yloxy]-1-[4-(4-nitronaphth-1-yl)piperazin-1-yl]ethanone, 4-(4-{2-[3-(2-Aminoethyl)-1H-indol-5-yloxy]acetyl}-piperazin-1-yl)phenyl methanesulfonate, 6-[3-(2-Aminoethyl)-1H-indol-5-yloxy]-1-[4-(4-nitrophenyl)piperazin-1-yl]hexan-1-one, 6-[3-(2-Aminoethyl)-1H-indol-5-yloxy]-1-[4-(4-aminophenyl)piperazin-1-yl]hexan-1-one, N-[4-(4-{6 -[3-(2-Aminoethyl)-1H-indol-5-yloxy] hexanoyl}-piperazin-1-yl)phenyl] methanesulfonamide, N-[4-(4-{6-[3-(2-Aminoethyl)-1H-indol-5-yloxy] hexanol}-piperazin-1-yl)benzyl]benzenesulfonamide, 5-[3-(2-Aminoethyl)-1H-indol-5-yloxy]-1-[4-(4-nitrophenyl)piperazin-1-yl]pentan-1-one, 5-[3-(2-Aminoethyl)-1H-indol-5-yloxy]-1-[4-(aminophenyl)-piperazin-1-yl]-pentan-1-one, 4-[3-(2-Aminoethyl)-1H-indol-5-yloxy]-1-[4-(4-nitrophenyl)piperazin-1-yl]butan-1-one, N-[4-(4-{2-[3-(2-Amino)-1H-indol-5-yloxy]acetyl}-piperazin-1-yl)phenyl]-4-cyanophenylsulfonamide, N-[4-(4-{2-[3-(2-Amino)-1H-indol-5-yloxy]acetyl}-piperazin-1-yl)phenyl]-4-(trifluoromethane) phenylsulfonamide, N-[4-(4-{2-[3-(2-Amino)-1H-indol-5-yloxy]acetyl}-piperazin-1-yl)phenyl]-4-methoxyphenyl sulfonamide, N-[4-(4-{2-[3-(2-Amino)-1H-indol-5-yloxy]acetyl}-piperazin-1-yl)phenyl]-4-fluorophenylsulfonamide, N-[4-(4-{2-[3-(2-Amino)-1H-indol-5-yloxy]acetyl}-piperazin-1-yl)phenyl]-4-acetamidophenylsulfonamide, N-[4-(4-{2-[3-(2-Amino)-1H-indol-5-yloxy]acetyl}-piperazin-1-yl)phenyl]-4-aminophenyl sulfonamide, N-[4-(4-{2-[3-(2-Amino)-1H-indol-5-yloxy]acetyl}-piperazin-1-yl)phenyl]-4-(methanesulfonylamino) phenylsulfonamide, its salts, which are acceptable for therapeutic use.

3. Pharmaceutical composition containing, as active ingredient an effective amount of a compound according to claim 1 in combination with an acceptable pharmaceutical vehicle.

4. Pharmaceutical composition containing, as active ingredient an effective amount of a compound according to claim 2 in combination with an acceptable pharmaceutical vehicle.

5. A method of treating anxiety, depression, migraine attacks, facial vascular pain, and chronic vascular cephalagias in a patient in need of such treatment, comprising the step of administering to the patient an effective amount of at least one compound according to claim 1.

6. A method of treating anxiety, depression, migraine attacks, facial vascular pain, and chronic vascular cephalagias in a patient in need of such treatment, comprising the step of administering to the patient an effective amount of at least one compound according to claim 2.

7. Process for the preparation of a compound of formula (I)

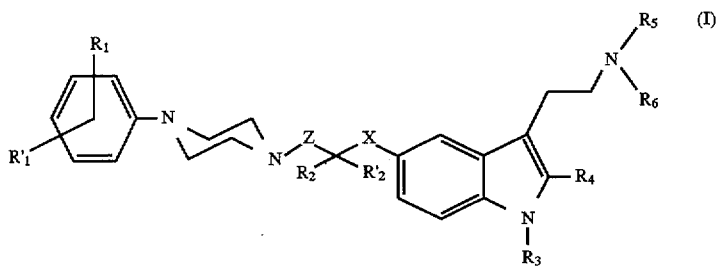

in which:

- $R_1$ represents an $NH_2$, $NO_2$, $NH-NH_2$, $NH-OH$, $NCOR_7(OH)$, $NR_5R_6$, $NHCOR_7$, $NHCONR_5R_7$, $NHSO_2R_7$, $NHCO_2R_7$, $SO_2R_7$, $SO_2NHR_7$, $NHCH_2SR_7$, $NHCH_2S(O)R_7$, $NHCH_2SO_2R_7$, CN, $NHCONH_2$, $SO_2NH_2$, $N(SO_2R_7)_2$, $CH_2NR_5R_6$, $CH_2NHCOR_7$, $CH_2NHCONR_5R_6$, $CH_2NHSO_2R_7$, $CH_2NHCO_7$, or $OSO_2R_7$ radical which can be in the o, m, or p position on the aromatic ring,

- $R'_1$ represents a substituent which can be in various positions on the aromatic ring, selected from H, methyl, ethyl, propyl, isopropyl, n-butyl, s-butyl, t-butyl, trifluoromethyl, 2,2,2-trifluoroethyl, phenyl, benzyl, phenethyl, cycloalkyl, OH, $SR_5$, $OR_5$, chlorine, fluorine, bromine, and iodine, or alternatively $R'_1$ can be identical to $R_1$,

- Z represents C=O, C=S, $SO_2$, $(CH_2)_n$, or $-CO(CH_2)_n-$ in which n is 1 to 5, inclusive,

- $R_2$ and $R'_2$, which are identical or different, each represent a hydrogen atom, a linear or branched alkyl radical, or a phenyl, benzyl, cycloalkyl, or phenyl-alkyl radical which is optionally substituted by a substituent chosen from halogen, alkyl, phenyl, carbonyl-derived $C_1-C_6$ acyl, alkoxy, and alkylthio radicals,

- X represents $CH_2$ or O; the $-C(R_2R'_2)-X$ group can also represent a C=C double bond,

- $R_3$ represents a hydrogen atom, a linear or branched alkyl radical, or a phenyl, $COR_7$, $CO_2$, $CO_2R_7$, $CONHR_7$, or $SO_2R_7$ radical,

- $R_4$ represents a hydrogen, chlorine, fluorine, or bromine atom, or a linear or branched alkyl radical,

- $R_5$ and $R_6$, which are identical or different, each represent a hydrogen atom, a linear or branched alkyl radical selected from methyl, ethyl, n-propyl, isopropyl, n-butyl, s-butyl, and t-butyl, or an arylalkyl radical selected from benzyl and phenethyl,

- $R_7$ represents a linear or branched alkyl radical having 1 to 5 carbon atoms inclusive, trifluoromethyl, 2,2,2-trifluoroethyl, phenyl, a heterocycle selected from thiophene, isoxazole, or arylalkyl selected from benzyl and phenethyl in which the aromatic ring may be variously substituted in various positions by methyl, ethyl, propyl or butyl, trifluoromethyl, 2,2,2-trifluoroethyl, hydroxyl, thiol, $OCH_3$, $OC_2H_5$ or $OCH(Me)_2$, $SCH_3$ or $SC_2H_5$, chlorine, fluorine, bromine, or iodine, nitrile, $(COR_5)$, $CO_2R_5$, $NO_2$, $NR_5R_6$, $NHSO_2R_5$, $NHCO_2R_5$, $NHCOR_5$, $NHCONR_5R_6$ or $NHSO_2NR_5R_6$, and $R_6$ represents a hydrogen, and its salts which are acceptable in therapeutic use, characterized in that a carbonate of formula

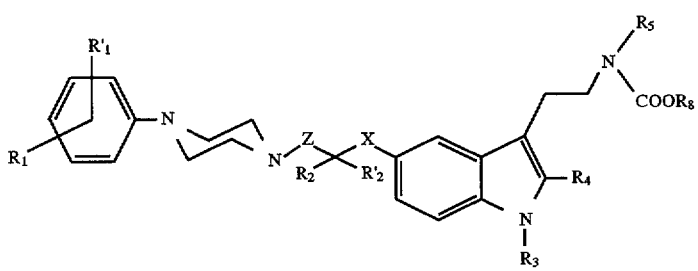

in which all of the symbols have the same meaning as given in the foregoing and $R_8$ represents a $^t$butyl or benzyl radical, is converted by acid hydrolysis when $R_8$ represents $^t$Bu or by catalytic hydrogenation over palladium when $R_8$ represents a benzyl.

* * * * *

UNITED STATES PATENT AND TRADEMARK OFFICE
CERTIFICATE OF CORRECTION

PATENT NO. : 5,726,177
DATED : March 10,1998
INVENTOR(S) : Serge Halazy, Michel Perez, Michael Briley, Peter Pauwels Page 1 of 4

It is certified that error appears in the above-indentified patent and that said Letters Patent is hereby corrected as shown below:

Column 2, line 62: At the end of the line, "$N(SO_2R_7)$" should read -- $N(SO_2R_7)_2$, --. Page 3, line 25

Column 2, line 63: Delete "$_2$," at the beginning of the line.

Column 3, line 11: The word "acycl" should read -- acyl --. Page 1 of Response and Amendment After Final Rejection, dtd 7/23/97, IN THE SPECIFICATION, page 4, line 14.

Column 3, line 50: "$(NRSR_6)$," should read -- $(NR_5R_6)$, -- Page 5, line 3

Column 3, line 52: "solyates" should read -- solvates -- Page 5, line 5

Column 4, line 11: "solyates" should read -- solvates -- page 5, line 18

Column 4, line 19: "maleares," should read -- maleates, --. Page 5, line 26

Column 4, line 45: "solyates" should read -- solvates -- Page 6, line 3

Column 4, line 49: "solyates" should read -- solvates -- Page 6, line 7

UNITED STATES PATENT AND TRADEMARK OFFICE
CERTIFICATE OF CORRECTION

PATENT NO. : 5,726,177

DATED : March 10, 1998

INVENTOR(S) : Serge Halazy, Michel Perez, Michael Briley, Peter Pauwels

Page 2 of 4

It is certified that error appears in the above-indentified patent and that said Letters Patent is hereby corrected as shown below:

Column 7, line 4: "anintermediate" should read
    -- an intermediate --.  Page 10, line 28

Column 14, line 8 (approx.): "-([4-" should read
    -- [4-(4- --.  Response and Amendment dtd 7/23/97,
    IN THE SPECIFICATION, page 22, line 6

Column 20, line 41: "mg, 1.62=mmol)" should read
    -- mg, 1.62 mmol) --.  Page 30, line 2

Column 21, line 28: "(80/6.5/15, v/v)" should read
    -- (80/16.5/15, v/v) --.  Page 31, line 6

Column 21, line 33: At the beginning of the line,
    "7.49," should read -- 47.49, --.  Page 32, line 11

Column 21, line 33: At the end of the line, "H"
    should read -- 1H --.  Page 31, line 12

Column 48, line 50: "7.43-7.58 m, H;" should read:
    -- 7.43-7.58 m, 2H; --.  Page 60, line 15

Column 49, line 24: "piperazin1-yl)" should read
    -- piperazin-1yl) --.  Page 61, line 9

Column 49, line 55: "piperazin1yl]" should read
    -- piperazin-1yl] --.  Page 61, line 27

UNITED STATES PATENT AND TRADEMARK OFFICE
CERTIFICATE OF CORRECTION

PATENT NO. : 5,726,177
DATED : March 10, 1998
INVENTOR(S) : Serge Halazy, Michel Perez, Michael Briley, Peter Pauwels It is certified that error appears in the above-indentified patent and that said Letters Patent is hereby corrected as shown below:

Column 52, line 30: "Example 1" should read -- Example 2 --. Pae 64, line 21

Column 72, line 28: At the end of the line, "aminoethyl)" should read -- aminoethyl)-1H- --. Page 4 of Response and Amendment after Final Rejection, dtd 7/23/97, 10th line down.

Column 75, line 1: "SCT" should read -- 5CT --. Page 87, line 26

Column 79, line 26: Delete "N(SO$_2$R$_6$," and replace with -- N(SO$_2$R$_7$)$_2$, CH$_2$NR$_5$R$_6$, --. Page 2 of Response and Amendment dtd 2/24/97, Claim 1, line 7.

Column 80, line 9: "(4-" at the end of the line, should read -- [4-(4- --. Page 96, line 26

Column 82, line 6: 'methane sulfonamide" should read -- methanesulfonamide". Page 99, line 14

Column 82, line 55: After the word "phenylsulfonamide.", delete the "." (period) and insert -- , and --. Page 3 of Preliminary Amendment dtd 5/17/96, Claim 2, (on page 100), line 13.

UNITED STATES PATENT AND TRADEMARK OFFICE
CERTIFICATE OF CORRECTION

PATENT NO. : 5,726,177

DATED : March 10, 1998

INVENTOR(S) : Serge Halazy, Michel Perez, Michael Briley, Peter Pauwels

It is certified that error appears in the above-indentified patent and that said Letters Patent is hereby corrected as shown below:

Column 83, line 32: "$CH_2NHCO_7$" should read: -- $CH_2NHCO_2R_7$ --. Page 4 of "Response and Amendment dtd 2/24/97, Claim 16, line 7.

Signed and Sealed this

Twenty-fifth Day of August, 1998

Attest:

Attesting Officer

BRUCE LEHMAN

Commissioner of Patents and Trademarks